US005776981A

United States Patent [19]
Potter et al.

[11] Patent Number: 5,776,981
[45] Date of Patent: Jul. 7, 1998

[54] USE OF ACYL UREA COMPOUNDS FOR CONTROLLING ENDOPARASITES AND ECTOPARASITES OF WARM-BLOODED ANIMALS

[75] Inventors: Michael Fred Potter; George Lorton Rotramel, both of Raleigh; Andrew James Caruso, Durham; David Teh-Wei Chou, Raleigh; Paul Alfred Cain, Cary, all of N.C.

[73] Assignee: Novartis Corporation, Summit, N.J.

[21] Appl. No.: 426,092

[22] Filed: Apr. 21, 1995

Related U.S. Application Data

[62] Division of Ser. No. 924,089, Aug. 3, 1992, Pat. No. 5,420,163, which is a division of Ser. No. 804,638, Dec. 6, 1985, Pat. No. 5,135,953, which is a continuation-in-part of Ser. No. 723,588, Apr. 15, 1985, abandoned, which is a continuation-in-part of Ser. No. 687,249, Dec. 28, 1984, abandoned.

[51] Int. Cl.$^6$ ..................................................... A01N 47/28
[52] U.S. Cl. .................. 514/594; 514/220; 514/249; 514/304; 514/305; 514/546; 514/547; 514/596; 514/724
[58] Field of Search ........................... 514/594, 596, 514/220, 249, 304, 305, 546, 547, 724

[56] References Cited

U.S. PATENT DOCUMENTS

| 5,135,953 | 8/1992 | Potter et al. | 514/594 |
| 5,420,163 | 5/1995 | Potter et al. | 514/594 |

OTHER PUBLICATIONS

Chemical Abstracts (99: 88061y), 1983.
*The Merck Index*, ab. No. 3125, 1983.

*Primary Examiner*—Kevin E. Weddington
*Attorney, Agent, or Firm*—Michael P. Morris

[57] ABSTRACT

A method of systemically controlling endoparasites and ectoparasites of warm-blooded animals by orally or percutaneously administering to the animal a parasiticidally effective amount of an acyl urea compound.

56 Claims, No Drawings

USE OF ACYL UREA COMPOUNDS FOR CONTROLLING ENDOPARASITES AND ECTOPARASITES OF WARM-BLOODED ANIMALS

This is a divisional of application Ser. No. 07/924,089 filed Aug. 3, 1992 now U.S. Pat. No. 5,420,168, which is a divisional of 06/804,638 filed Dec. 6, 1985, now U.S. Pat. No. 5,135,953 which is a CIP of 06/723,588 filed on Apr. 15, 1985, now abandoned which is a CIP of 06/687,249 filed on Dec. 28, 1984 now abandoned.

BRIEF SUMMARY OF THE INVENTION

1. Technical Field

This invention relates to the use of acyl urea compounds for the systemic control of endoparasites and ectoparasites of warm-blooded animals.

2. Background of the Invention

Animal parasites, such as mites, lice, ticks, grubs, biting flies, coccidia, flukes, tapeworms, hookworms and other helminths, cause severe economic losses to livestock producers. Infestations may result in reduced feed efficiency, weight loss, decreased production of milk or eggs, and increased incidence of disease or death. The control of animal parasites is therefore one of the most important problems in the field of animal husbandry.

Certain insecticides, such as coumaphos, carbaryl and lindane, are currently available for control of some of these parasites. Insect growth regulators, such as methoprene (juvenile hormone mimic) and diflubenzuron, have been used as feed additives to control fly larvae in livestock and chicken manure. See, for example, Breeden et al. *J. Econ. Entomol.* 68 (4), 451–452 (1975) and Barker and Newton, *J. Ga. Entomol. Soc.* 11 (1), 71–75 (1976). Additionally, Barrett et al. *Southwest Entomol.* 3 (3), 232–236 (1978) and Prasert et al. *J. Econ. Entomol.* 68 (5), 639–640 (1975) report that oral administration of methoprene to cattle and sheep will help control cattle grubs and sheep bot fly respectively. Devaney and Kubena, *Insecticide and Acaricide Tests* 7, 247 (1982) concluded that diflubenzuron,on the other hand, was not effective for systemic control of northern fowl mite on poultry.

Systemic control of animal parasites is accomplished by absorbing a parasiticide in the bloodstream or other tissues of the host animal. Parasites which eat or come into contact with the parasiticide-containing blood or.tissue are killed, either by ingestion or contact. Only a very few insecticides have been found to be sufficiently nontoxic to be used systemically in animals.

Accordingly, the object of this invention is to provide a method for the use of certain acyl urea compounds to systemically control animal parasites. This and other objects will readily become apparent to those skilled in the art in light of the teachings herein set forth.

DISCLOSURE OF THE INVENTION

This invention relates to a method for controlling parasites of warm-blooded animals which comprises administering to the animal a parasiticidally effective amount of a compound having the formula:

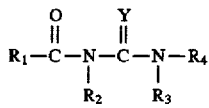

wherein $R_1$, $R_2$, $R_3$, $R_4$ and Y are as defined hereinafter.

DETAILED DESCRIPTION

As indicated above, this invention relates to a method of controlling parasites of warm-blooded animals by administration of certain acyl urea compounds. More particularly, this invention involves a method for controlling endoparasites and ectoparasites of warm-blooded animals by orally or percutaneously administering to the animal a parasiticidally effective amount of a compound having the formula:

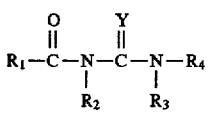

(I)

wherein:

$R_1$ and $R_4$ are independently a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents (Z) are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfiny, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, $-X$, $=X$, $-X=R_5$, $=X-R_5$, $-X-R_5$, -continued

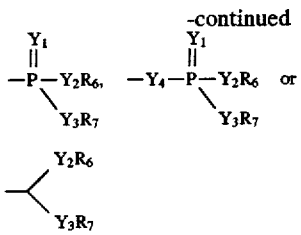

wherein R₅ is a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents (Z) are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

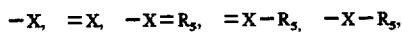

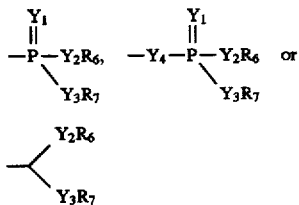

Y₁ and Y₄ are independently oxygen or sulfur, Y₂ and Y₃ are independently oxygen, sulfur, amino or a covalent bond, R₆ and R₇ are independently hydrogen or substituted or unsubstituted alkyl, polyhaloalkyl, phenyl or benzyl in which the permissible substituents (Z) are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide.

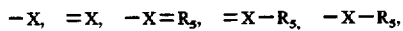

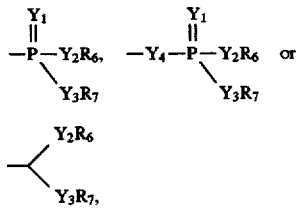

X is a covalent single bond or double bond, a substituted or unsubstituted heteroatom or substituted carbon atom, or a substituted or unsubstituted, branched or straight chain containing two or more carbon atoms or heteroatoms in any combination in which the permissible substituents (Z) are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide.

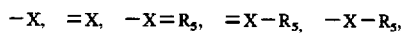

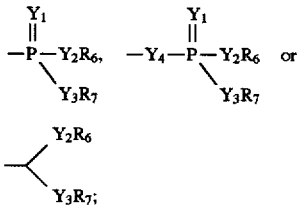

or $R_4$ is hydrogen;

Y is oxygen or sulfur; and $R_2$ and $R_3$ are independently hydrogen, alkyl, substituted alkyl in which the permissible substituents are the same or different and are one or more halogen, alkoxy, alkylthio, or cyano; cycloalkyl, cycloalkenyl, substituted benzyl in which the permissible substituents are the same or different and are one or more halogen, hydroxy, nitro, cyano, alkyl, polyhaloalkyl, alkoxy or polyhaloalkoxy; hydroxy, alkoxy, polyhaloalkoxy, alkylthio, polyhaloalkylthio, acyl, alkoxycarbonyl, alkoxythiocarbonyl, alkylsulfonyl, substituted phenylsulfonyl in which the permissible substituents are the same or different and are one or more halogen, nitro, cyano or polyhaloalkyl; substituted phenylthio in which the permissible substituents are the same or different and are one or more halogen, alkyl, nitro, cyano, polyhaloalkyl, or substituted or unsubstituted alkoxycarbonyl, alkenoxycarbonyl, alkynoxycarbonyl, cycloalkoxycarbonyl, phenoxycarbonyl, hydroxycarbonyl or the alkali metal salt or ammonium salt thereof, alkyl, alkoxy, alkylthio, cycloalkyl, cycloalkyloxy, cycloalkylthio, alkenyl, alkenylthio, alkanoyl, alkylsulfonyl, alkynyl, phenyl, phenoxy, phenylthio or amino: N-(alkylcarbonyl)-N-alkylaminothio, alkoxycarbonylthio, trialkylsilyl, dialkylarylsilyl, thiarylsilyl,

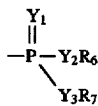

or $R_2$ and $R_3$ are independently

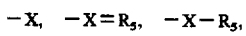

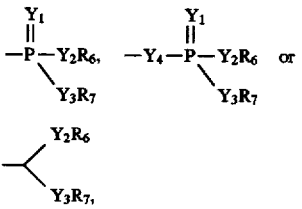

or $R_2$ and $R_3$ may be linked together to form a substituted or unsubstituted, heterocyclic ring system which may be saturated or unsaturated and in which the permissible substitutents (Z) are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide.

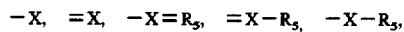

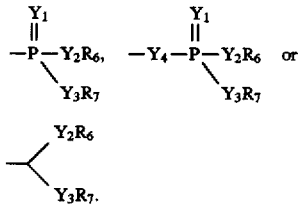

Certain Z groups which may be substituted or unsubstituted include aryloxyiminomethyl and arylhydrazonomethyl. Other groups within the definition of $R_2$ and $R_3$ which may be substituted or unsubstituted include alkoxycarbonyl, alkenoxycarbonyl, alkynoxycarbonyl, cycloalkoxycarbonyl, phenoxycarbonyl, hydroxycarbonyl or the alkali metal salt or ammonium salt thereof, alkyl, alkoxy, alkylthio, cycloalkyl, cycloalkyloxy, cycloalkylthio, alkenyl, alkenylthio, alkanoyl, alkylsulfonyl, alkynyl, phenyl, phenoxy, phenylthio and amino. Permissible substituents for these groups include independently one or more halogen, alkyl, alkoxy, polyhaloalkyl, polyhaloalkoxy, cyano, nitro, alkylthio, alkylsulfinyl, alkylsulfonyl, polyhaloalkylthio, polyhaloalkylsulfonyl, trialkylsilyl and aryldialkylsilyl in any combination.

The alkyl-containing moieties above may contain from about 1 to about 100 carbon atoms or greater, preferably from about 1 to about 30 carbon atoms, and more preferably from about 1 to about 20 carbon atoms. The polysaccharide moiety may contain up to about 50 carbon atoms.

Monocyclic ring systems emcompassed by $R_1$, $R_4$ and $R_5$ in formula 1 may be represented by generalized formula 2 as follows:

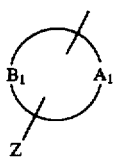

wherein $B_1$ represents a saturated or unsaturated carbon atom and $A_1$ represents a ring-forming chain of atoms which together with $B_1$ forms a cyclic system containing from 0 to 3 double bonds or from 0 to 2 triple bonds. $A_1$ may contain entirely from 2 to 12 carbon atoms, may contain a combination of from 1 to 11 carbon atoms and from 1 to 4 heteroatoms which may be selected independently from N, O, S, P or other heteroatoms, or may contain 4 ring-forming heteroatoms alone.

Ring-forming heteroatoms may in some cases bear oxygen atoms as in aromatic N-oxides and ring systems containing the sulfinyl, sulfonyl, selenoxide and phosphono moieties.

Selected carbon atoms contained in cycles formed by $B_1$ and $A_1$ containing more than 3 ring-forming atoms may bear carbonyl, thiocarbonyl, substituted or unsubstituted imino groups or substituted or unsubstituted methylidene groups.

The group designated as Z represents one or more substituents selected independently from among the group of substituents defined for Z herein. When the cycle formed by $B_1$ and $A_1$ contains fewer than 4 ring forming members, it should be a saturated carbocycle, i.e. cyclopropyl. When the cycle formed by $B_1$ and A1 contains fewer than 5 ring-forming members, it should contain no more than 1 heteroatom.

Representative illustrations of $A_1$ include the following:

(1) A chain of from 2–12 carbon atoms which together with B contains 0 double bonds;

(2) A chain of from 4–12 carbon atoms which together with B contains 1 double bond;

(3) A chain of from 4–12 carbon atoms which together with B contains 2 double bonds:

(4) A chain of from 5–12 carbon atoms which together with B contains 3 double bonds:

(5) A chain containing 1 heteratom and from 2 to 11 carbon atoms which together with $B_1$ contains 0 double bonds:

(6) A chain containing 1 heteroatom and from 3–11 carbon atoms which together with $B_1$ contains 1 double bond;

(7) A chain containing 1 heteroatom and from 3–11 carbon atoms which together with $B_1$ contains 2 double bonds;

(8) A chain containing 1 heteroatom and from 4–11 carbon atoms which together with $B_1$ contains 3 double bonds:

(9) A chain containing 2 heteroatoms and from 2–10 carbon atoms which together with $B_1$ contains 0 double bonds;

(10) A chain containing 2 heteroatoms and from 2–10 carbon atoms which together with $B_1$ contains 1 double bond;

(11) A chain containing 2 heteroatoms and from 2–10 carbon atoms which together with $B_1$ contains 2 double bonds;

(12) A chain containing 2 heteroatoms and from 3–10 carbon atoms which together with $B_1$ contains 3 double bonds;

(13) A chain containing 3 heteroatoms and from 1–9 carbon atoms which together with $B_1$ contains 0 double bonds:

(14) A chain containing 3 heteroatoms and from 1–9 carbon atoms which together with $B_1$ contains 1 double bond;

(15) A chain containing 3 heteroatoms and from 1–9 carbon atoms which together with $B_1$ contains 2 double bonds;

(16) A chain containing 3 heteroatoms and from 2–9 carbon atoms which together with $B_1$ contains 3 double bonds;

(17) A chain containing 4 heteroatoms and from 0–8 carbon atoms which together with $B_1$ contains 0 double bonds;

(18) A chain containing 4 heteroatoms and from 0–8 carbon atoms which together with $B_1$ contains 1 double bond;

(19) A chain containing 4 heteroatoms and from 0–8 carbon atoms which together with $B_1$ contains 2 double bonds; and

(20) A chain containing 4 heteroatoms and from 1–8 carbon atoms which together with $B_1$ contains 3 double bonds.

Illustrative monocyclic ring structures which are encompassed by $R_1$, $R_4$ and $R_5$ in formula 1 include the following:

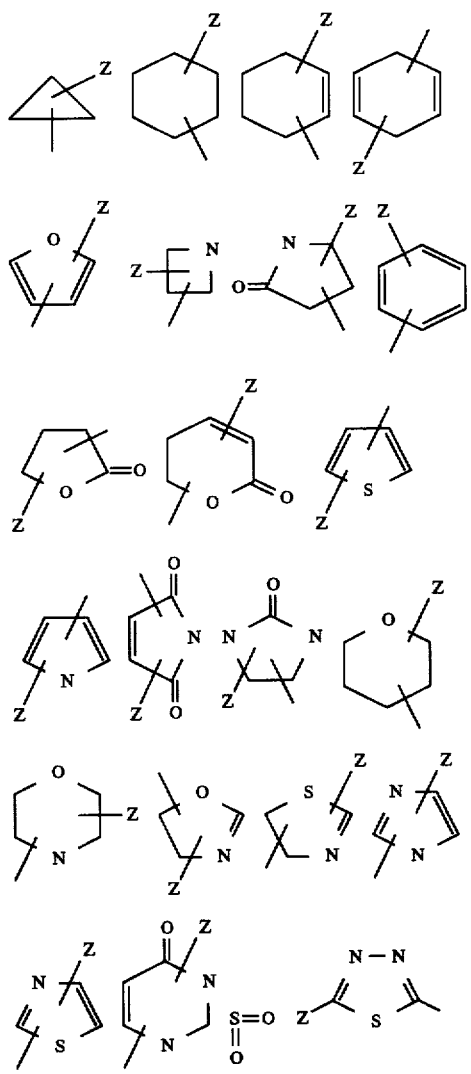

-continued

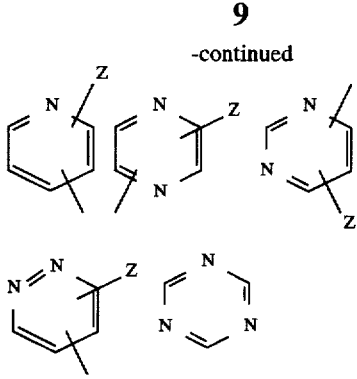

wherein Z is as defined herein.

Bicyclic ring systems encompassed by $R_1$, $R_4$ and $R_5$ in formula 1 may be represented by generalized formulae 3 and 4 as follows:

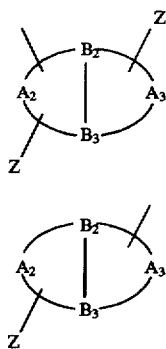

wherein $B_2$ and $B_3$ may be independently a saturated or unsaturated carbon atom or a saturated nitrogen atom, $A_2$ and $A_3$ independently represent the ring-forming chains of atoms described below and Z represents one or more substituents selected independently from among the group of substituents defined for Z herein. Combinations of $A_2$ and $A_3$ may be selected from among the arrays of atoms listed below in items (21) through (98) and may contain in combination with either $B_1$ or $B_2$, but not both, from 0 to 2 double bonds. $A_2$ and $A_3$, independent of $B_2$ and $B_3$, may contain enitirely from 1 to 11 carbon atoms, may contain a combination of 1 to 3 heteroatoms which may be selected independently from among N, O, S, P or other heteroatoms together with from 1 to 10 carbon atoms or may contain from 1–3 ring-forming heteroatoms alone.

Ring-forming heteroatoms may in some cases bear oxygen atoms, as in aromatic N-oxides and ring systems containing the sulfinyl, sulfonyl, selenoxide and phosphono groups. Selected carbon atoms contained in $A_2$ and $A_3$ may bear carbonyl, thiocarbonyl, substituted or unsubstituted imino groups or substituted or unsubstituted methylidene groups.

In regard to structures encompassed within formulae 3 and 4, it is noted as follows:

(a) When $B_2$ and $B_3$ are both nitrogen, the groups $A_2$ and $A_3$ should each contain no fewer than three ring atoms;

(b) When $B_2$ but not $B_3$ is nitrogen, either of $A_2$ or $A_3$ should contain at least three ring atoms and the other at least two ring atoms:

(c) When either of groups $A_2$ or $A_3$ contains fewer than three ring atoms, the other should contain at least three ring atoms and the bridgehead atoms should be saturated;

(d) When the group $A_2$ or $A_3$ contains a carbon atom bearing a carbonyl, thiocarbonyl, imino or methylidene group, it should together with $B_2$ and $B_3$ form a cycle having at least four members;

(e) When a annular double bond is exocyclic to either of the two rings represented in structures 3 and 4, it should be contained in a ring containing at least five members and be exocyclic to a ring containing at least five members; and (f) When a group $A_2$ or $A_3$ is joined to the bridgehead atoms $B_1$ and $B_2$ double bonds, the group $A_2$ or $A_3$ is understood to contain one double bond and the bridgehead atoms are considered to be unsaturated.

It is recognized that bycyclic ring systems defined for $R_1$, $R_4$ and $R_5$ may be spirocyclic ring systems and are not limited to the fused bicyclic structures of formulae 3 and 4. spirocyclic ring systems may be saturated or unsaturated carbocyclic or heterocyclic and may be independently substituted by one or more substituents Z as defined herein.

Illustrative combinations of $A_2$ and $A_3$ which are encompassed within generalized formulae 3 and 4 are listed below as follows:

(21) $A_2$ is a chain containing from 1–11 carbon atoms which together with $B_2$ or $B_3$ contains 0 double bonds and $A_3$ is a chain containing 3–11 carbon atoms which together with $B_2$ or $B_3$ contains 0 double bonds;

(22) $A_2$ is a chain containing from 3–11 carbon atoms which together with $B_2$ or $B_3$ contains 1 double bond and $A_3$ is a chain containing 3–11 carbon atoms which together with $B_2$ or $B_3$ contains 0 double bonds;

(23) $A_2$ is a chain containing from 3–11 carbon atoms which together with $B_2$ or $B_3$ contains 1 double bond and $A_3$ is a chain containing 3–11 carbon atoms which together with $B_2$ or $B_3$ contains 1 double bond;

(24) $A_2$ is a chain containing from 3–11 carbon atoms which together with $B_2$ or $B_3$ contains 2 double bonds and $A_3$ is a chain containing 3–11 carbon atoms which together with $B_2$ or $B_3$ contains 0 double bonds;

(25) $A^2$ is a chain containing from 3–11 carbon atoms which together with $B_2$ or $B_3$ contains 2 double bonds and $A_3$ is a chain containing 3–11 carbon atoms which together with $B_2$ or $B_3$ contains I double bond;

(26) $A_2$ is a chain containing from 3–11 carbon atoms which together with $B_2$ or $B_3$ contains 2 double bonds and $A_3$ is a chain containing 4–11 carbon atoms which together with $B_2$ or $B_3$ contains 2 double bonds:

(27) $A_2$ is a chain containing 1 heteroatom and from 0–10 carbon atoms which together with $B_2$ or $B_3$ contains 0 double bonds and $A_3$ is a chain containing 1–11 carbon atoms which together with $B_2$ or $B_3$ contains 0 double bonds;

(28) $A_2$ is a chain containing 1 heteroatom and from 2–10 carbon atoms which together with $B_2$ or $B_3$ contains 1 double bond and $A_3$ is a chain containing 1–11 carbon atoms which together with $B_2$ or $B_3$ contains 0 double bonds;

(29) $A_2$ is a chain containing 1 heteroatom and from 2–10 carbon atoms which together with $B_2$ or $B_3$ contains 2 double bonds and $A_3$ is a chain containing from 3–11 carbon atoms which together with $B_2$ or $B_3$ contains 0 double bonds;

(30) $A_2$ is a chain containing 1 heteroatom and from 2–10 carbon atoms which together with $B_2$ or $B_3$ contains 2 double bonds and $A_3$ is a chain containing from 3–11 carbon atoms which together with $B_2$ or $B_3$ contains 1 double bond;

(31) $A_2$ is a chain containing 1 heteroatom and from 2–10 carbon atoms which together with $B_2$ or $B_3$ contains 2 double bonds and $A_3$ is a chain containing from 4–11 carbon atoms which together with $B_2$ or $B_3$ contains 2 double bonds;

(32) $A_2$ is a chain containing 1 heteroatom and from 0–10 carbon atoms which together with $B_2$ or $B_3$ contains 0 double bonds and $A_3$ is a chain containing from 3–11 carbon atoms which together with $B_2$ or $B_3$ contains 1 double bond;

(33) $A_2$ is a chain containing 1 heteroatom and from 2–10 carbon atoms which together with $B_2$ or $B_3$ contains 0 double bonds and $A_3$ is a chain containing from 3–11 carbon atoms which together with $B_2$ or $B_3$ contains 2 double bonds;

(34) $A_2$ is a chain containing 1 heteroatom and from 2–10 carbon atoms which together with $B_2$ or $B_3$ contains 1 double bond and $A_3$ is a chain containing from 4–11 carbon atoms which together with $B_2$ or $B_3$ contains 2 double bonds;

(35) $A_2$ is a chain containing 1 heteroatom and from 2–10 carbon atoms which together with $B_2$ or $B_3$ contains I double bond and $A_3$ is a chain containing from 3–11 carbon ato..s which together with $B_2$ or $B_3$ contains 1 double bond;

(36) $A_2$ is a chain containing 2 heteroatoms and from 1–9 carbon atoms which together with $B_2$ or $B_3$ contains 0 double bonds and $A_3$ is a chain containing from 3–11 carbon atoms which together with $B_2$ or $B_3$ contains 0 double bonds;

(37) $A_2$ is a chain containing 2 heteroatoms and from 1–9 carbon atoms which together with $B_2$ or $B_3$ contains I double bond and $A_3$ is a chain containing from 3–11 carbon atoms which together with $B_2$ or $B_3$ contains 0 double bonds;

(38) $A_2$ is a chain containing 2 heteroatoms and from 1–9 carbon atoms which together with $B_2$ or $B_3$ contains 2 double bonds and $A_3$ is a chain containing from 3–11 carbon atoms which together with $B_2$ or $B_3$ contains 0 double bonds;

(39) $A_2$ is a chain containing 2 heteroatoms and from 1–9 carbon atoms which together with $B_2$ or $B_3$ contains 1 double bond and $A_3$ is a chain containing from 3–11 carbon atoms which together with $B_2$ or $B_3$ contains 1 double bond;

(40) $A_2$ ic a chain containing 2 heteroatoms and from 2–9 carbon atoms which together with $B_2$ or $B_3$ contains 2 double bonds and $A_3$ is a chain containing from 3–11 carbon atoms which together with $B_2$ or $B_3$ contains 1 double bond;

(41) $A_2$ is a chain containing 2 heteroatoms and from 2–9 carbon atoms which together with $B_2$ or $B_3$ contains 2 double bonds and $A_3$ is a chain containing from 3–11 carbon atoms which together with $B_2$ or $B_3$ contains 2 double bonds;

(42) $A_2$ is a chain containing 2 heteroatoms and from 1–9 carbon atoms which together with $B_2$ or $B_3$ contains 0 double bonds and $A_3$ is a chain containing from 3–11 carbon atoms which together with $B_2$ or $B_3$ contains 1 double bond:

(43) $A_2$ is a chain containing 2 heteroatoms and from 1–9 carbon atoms which together with $B_2$ or $B_3$ contains 0 double bonds and $A_3$ is a chain containing from 3–11 carbon atoms which together with $B_2$ or $B_3$ contains 2 double bonds;

(44) $A_2$ is a chain containing 2 heteroatoms and from 1–9 carbon atoms which together with $B_2$ or $B_3$ contains 1 double bond and $A_3$ is a chain containing from 3–11 carbon atoms which together with $B_2$ or $B_3$ contains 2 double bonds;

(45) $A_2$ is a chain containing 3 heteroatoms and from 0–8 carbon atoms which together with $B_2$ or $B_3$ contains 0 double bonds and $A_3$ is a chain containing from 2–11 carbon atoms which together with $B_2$ or $B_3$ contains 0 double bonds;

(46) $A_2$ is a chain containing 3 heteroatoms and from 1–8 carbon atoms which together with $B_2$ or $B_3$ contains 1 double bond and $A_3$ is a chain containing from 3–11 carbon atoms which together with $B_2$ or $B_3$ contains 0 double bonds;

(47) $A_2$ is a chain containing 3 heteroatoms and from 1–8 carbon atoms which together with $B_2$ or $B_3$ contains 2 double bonds and $A_3$ is a chain containing from 3–11 carbon atoms which together with $B_2$ or $B_3$ contains 0 double bonds;

(48) $A_2$ is a chain containing 3 heteroatoms and from 0–8 carbon atoms which together with $B_2$ or $B_3$ contains 0 double bonds and $A_3$ is a chain containing from 3–11 carbon atoms which together with $B_2$ or $B_3$ contains 1 double bond;

(49) $A_2$ is a chain containing 3 heteroatoms and from 0–8 carbon atoms which together with $B_2$ or $B_3$ contains 1 double bond and $A_3$ is a chain containing from 3–11 carbon atoms which together with $B_2$ or $B_3$ contains 1 double bond;

(50) $A_2$ is a chain containing 3 heteroatoms and from 2–8 carbon atoms which together with $B_2$ or $B_3$ contains 2 double bonds and $A_3$ is a chain containing from 3–11 carbon atoms which together with $B_2$ or $B_3$ contains 1 double bond;

(51) $A_2$ is a chain containing 3 heteroatoms and from 0–8 carbon atoms which together with $B_2$ or $B_3$ contains 0 double bonds and $A_3$ is a chain containing from 3–11 carbon atoms which together with $B_2$ or $B_3$ contains 2 double bonds:

(52) $A_2$ is a chain containing 3 heteroatoms and from 2–8 carbon atoms which together with $B_2$ or $B_3$ contains 1 double bond and $A_3$ is a chain containing from 3–11 carbon atoms which together with $B_2$or $B_3$ contains 2 double bonds;

(53) $A_2$ is a chain containing 3 heteroatoms and from 0–8 carbon atoms which together with $B_2$ or $B_3$ contains 2 double bonds and $A_3$ is a chain containing from 3–11 carbon atoms which together with $B_2$ or $B_3$ contains 2 double bonds;

(54) $A_2$ is a chain containing 1 heteroatom and from 2–10 carbon atoms which together with $B_2$ or $B_3$ contains 0 double bonds and $A_3$ is a chain containing 1 heteroatom and from 2–10 carbon atoms which together with $B_2$ and $B_3$ contains 0 double bonds;

(55) $A_2$ is a chain containing 1 heteroatom and from 2–10 carbon atoms which together with $B_2$ or $B_3$ contains 1 double bond and $A_3$ is a chain containing 1 heteroatom and from 2–10 carbon atoms which together with $B_2$ and $B_3$ contains 0 double bonds;

(56) $A_2$ is a chain containing 1 heteroatom and from 2–10 carbon atoms which together with $B_2$ or $B_3$ contains 2 double bonds and $A_3$ is a chain containing 1 heteroatom and from 2–10 carbon atoms which together with $B_2$ and $B_3$ contains 0 double bonds;

(57) $A_2$ is a chain containing 1 heteroatom and from 2–10 carbon atoms which together with $B_2$ or $B_3$ contains 1 double bond and $A_3$ is a chain containing 1 heteroatom and from 2–10 carbon atoms which together with $B_2$ and $B_3$ contains 1 double bond:

(58) $A_2$ is a chain containing 1 heteroatom and from 2–10 carbon atoms which together with $B_2$ or $B_3$ contains 2 double bonds and $A_3$ is a chain containing 1 heteroatom and from 2–10 carbon atoms which together with $B_2$ and $B_3$ contains 1 double bond;

(59) $A_2$ is a chain containing 1 heteroatom and from 2–10 carbon atoms which together with $B_2$ or $B_3$ contains 2 double bonds and $A_3$ is a chain containing 1 heteroatom and from 2–10 carbon atoms which together with $B_2$ and $B_3$ contains 2 double bonds;

(60) $A_2$ is a chain containing 2 heteroatoms and from 1–9 carbon atoms which together with $B_2$ or $B_3$ contains 0 double bonds and $A_3$ is a chain containing 1 heteroatom and from 2–10 carbon atoms which together with $B_2$ and $B_3$ contains 0 double bonds;

(61) $A_2$ is a chain containing 2 heteroatoms and from 1–9 carbon atoms which together with $B_2$ or $B_3$ contains 1 double bond and $A_3$ is a chain containing I heteroatom and from 2–10 carbon atoms which together with $B_2$ and $B_3$ contains 0 double bonds;

(62) $A_2$ is a chain containing 2 heteroatoms and from 1–9 carbon atoms which together with $B_2$ or $B_3$ contains 2 double bonds and $A_3$ is a chain containing 1 heteroatom and from 2–10 carbon atoms which together with $B_2$ and $B_3$ contains 0 double bonds;

(63) $A_2$ is a chain containing 2 heteroatoms and from 1–9 carbon atoms which together with $B_2$ or $B_3$ contains 0 double bonds and $A_3$ is a chain containing 1 heteroatom and from 2–10 carbon atoms which together with $B_2$ and $B_3$ contains 1 double bond;

(64) A is a chain containing 2 heteroatoms and from 1–9 carbon atoms which together with $B_2$ or $B_3$ contains 1 double bond and $A_3$ is a chain containing 1 heteroatom and from 2–10 carbon atoms which together with $B_2$ and $B_3$ contains 1 double bond;

(65) $A_2$ is a chain containing 2 heteroatoms and from 1–9 carbon atoms which together with $B_2$ or $B_3$ contains 2 double bonds and $A_3$ is a chain containing 1 heteroatom and from 2–10 carbon atoms which together with $B_2$ and $B_3$ contains 1 double bond;

(66) $A_2$ is a chain containing 2 heteroatoms and from 1–9 carbon atoms which together with $B_2$ or $B_3$ contains 0 double bonds and $A_3$ is a chain containing 1 heteroatom and from 2–10 carbon atoms which together with $B_2$ and $B_3$ contains 2 double bonds;

(67) $A_2$ is a chain containing 2 heteroatoms and from 1–9 carbon atoms which together with $B_2$ or $B_3$ contains 1 double bond and $A_3$ is a chain containing 1 heteroatom and from 2–10 carbon atoms which together with $B_2$ and $B_3$ contains 2 double bonds;

(68) $A_2$ is a chain containing 2 heteroatoms and from 1–9 carbon atoms which together with $B_2$ or $B_3$ contains 2 double bonds and $A_3$ is a chain containing 1 heteroatom and from 2–10 carbon atoms which together with $B_2$ or $B_3$ contains 2 double bonds:

(69) $A_2$ is a chain containing 3 heteroatoms and from 0–8 carbon atoms which together with $B_2$ or $B_3$ contains 0 double bonds and $A_3$ is a chain containing 1 heteroatom and from 2–10 carbon atoms which together with $B_2$ or $B_3$ contains 0 double bonds;

(70) $A_2$ is a chain containing 3 heteroatoms and from 1–8 carbon atoms which together with $B_2$ or $B_3$ contains 1 double bond and $A_3$ is a chain containing 1 heteroatom and from 2–10 carbon atoms which together with $B_2$ or $B_3$ contains 0 double bonds;

(71) $A_2$ is a chain containing 3 heteroatoms and from 1–8 carbon atoms which together with $B_2$ or $B_3$ contains 2 double bonds and $A_3$ is a chain containing 1 heteroatom and from 2–10 carbon atoms which together with $B_2$ or $B_3$ contains 0 double bonds;

(72) A is a chain containing 3 heteroatoms and from 0–8 carbon atoms which together with $B_2$ or $B_3$ contains 0 double bonds and $A_3$ is a chain containing 1 heteroatom and from 2–10 carbon atoms which together with $B_2$ or $B_3$ contains 1 double bond;

(73) $A_2$ is a chain containing 3 heteroatoms and from 1–8 carbon atoms which together with $B_2$ or $B_3$ contains 1 double bond and $A_3$ is a chain containing 1 heteroatom and from 2–10 carbon atoms which together with $B_2$ or $B_3$ contains 1 double bond;

(74) $A_2$ is a chain containing 3 heteroatoms and from 1–8 carbon atoms which together with $B_2$ or $B_3$ contains 2 double bonds and $A_3$ is a chain containing 1 heteroatom and from 2–10 carbon atoms which together with $B_2$ or $B_3$ contains 1 double bond:

(75) $A_2$ is a chain containing 3 heteroatoms and from 0–8 carbon atoms which together with $B_2$ or $B_3$ contains 0 double bonds and $A_3$ is a chain containing 1 heteroatom and from 2–10 carbon atoms which together with $B_2$ or $B_3$ contains 2 double bonds;

(76) $A_2$ is a chain containing 3 heteroatoms and from 1–8 carbon atoms which together with $B_2$ or $B_3$ contains 1 double bond and $A_3$ is a chain containing 1 heteroatom and from 2–10 carbon atoms which together with $B_2$ or $B_3$ contains 2 double bonds;

(77) $A_2$ is a chain containing 3 heteroatoms and from 1–8 carbon atoms which together with $B_2$ or $B_3$ contains 2 double bonds and $A_3$ is a chain containing 1 heteroatom and from 2–10 carbon atoms which together with $B_2$ or $B_3$ contains 2 double bonds;

(78) $A_2$ is a chain containing 2 heteroatoms and from 1–9 carbon atoms which together with $B_2$ or $B_3$ contains 0 double bonds and $A_3$ is a chain containing 2 heteroatoms and from 1–9 carbon atoms which together with $B_2$ or $B_3$ contains 0 double bonds;

(79) $A_2$ is a chain containing 2 heteroatoms and from 1–9 carbon atoms which together with $B_2$ or $B_3$ contains 1 double bond and $A_3$ is a chain containing 2 heteroatoms and from 2–9 carbon atoms which together with $B_2$ or $B_3$ contains 0 double bonds;

(80) $A_2$ is a chain containing 2 heteroatoms and from 1–9 carbon atoms which together with $B_2$ or $B_3$ contains 2 double bonds and $A_3$ is a chain containing 2 heteroatoms and from 1–9 carbon atoms which together with $B_2$ or $B_3$ contains 0 double bonds;

(81) $A_2$ is a chain containing 2 heteroatoms and from 1–9 carbon atoms which together with $B_2$ or $B_3$ contains 1 double bond and $A_3$ is a chain containing 2 heteroatoms and from 1–9 carbon atoms which together with $B_2$ or $B_3$ contains 1 double bond;

(82) $A_2$ is a chain containing 2 heteroatoms and from 1–9 carbon atoms which together with $B_2$ or $B_3$ contains 2 double bonds and $A_3$ is a chain containing 2 heteroatoms and from 1–9 carbon atoms which together with $B_2$ or $B_3$ contains 1 double bond:

(83) $A_2$ is a chain containing 2 heteroatoms and from 1–9 carbon atoms which together with $B_2$ or $B_3$ contains 2 double bonds and $A_3$ is a chain containing 2 heteroatoms and from 2–9 carbon atoms which together with $B_2$ or $B_3$ contains 2 double bonds;

(84) $A_2$ is a chain containing 3 heteroatoms and from 0–8 carbon atoms which together with $B_2$ or $B_3$ contains 0 double bonds and $A_3$ is a chain containing 2 heteroatoms and from 1–9 carbon atoms which together with $B_2$ or $B_3$ contains 0 double bonds;

(85) $A_2$ is a chain containing 3 heteroatoms and from 1–8 carbon atoms which together with $B_2$ or $B_3$ contains 1 double bond and $A_3$ is a chain containing 2 heteroatoms and from 1–9 carbon atoms which together with $B_2$ or $B_3$ contains 0 double bonds;

(86) $A_2$ is a chain containing 3 heteroatoms and from 1–8 carbon atoms which together with $B_2$ or $B_3$ contains 2 double bonds and $A_3$ is a chain containing 2 heteroatoms and from 1–9 carbon atoms which together with $B_2$ or $B_3$ contains 0 double bonds;

(87) $A_2$ is a chain containing 3 heteroatoms and from 0–8 carbon atoms which together with $B_2$ or $B_3$ contains 0 double bonds and $A_3$ is a chain containing 2 heteroatoms and from 1–9 carbon atoms which together with $B_2$ or $B_3$ contains 1 double bond; (88) $A_2$ is a chain containing 3 heteroatoms and from 0–8 carbon atoms which together with $B_2$ or $B_3$ contains 1 double bond and $A_3$ is a chain containing 2 heteroatoms and from 1–9 carbon atoms which together with $B_2$ or $B_3$ contains 1 double bond:

(89) $A_2$ is a chain containing 3 heteroatoms and from 0–8 carbon atoms which together with $B_2$ or $B_3$ contains 2 double bonds and $A_3$ is a chain containing 2 heteroatoms and from 1–9 carbon atoms which together with $B_2$ or $B_3$ contains 1 double bond;

(90) $A_2$ is a chain containing 3 heteroatoms and from 0–8 carbon atoms which together with $B_2$ or $B_3$ contains 0 double bonds and $A_3$ is a chain containing 2 heteroatoms and from 1–9 carbon atoms which together with $B_2$ or $B_3$ contains 2 double bonds:

(91) $A_2$ is a chain containing 3 heteroatoms and from 1–8 carbon atoms which together with $B_2$ or $B_3$ contains 1 double bond and $A_3$ is a chain containing 2 heteroatoms and from 2–9 carbon atoms which together with $B_2$ or $B_3$ contains 2 double bonds:

(92) $A_2$ is a chain containing 3 heteroatoms and from 1–8 carbon atoms which together with $B_2$ or $B_3$ contains 2 double bonds and $A_3$ is a chain containing 2 heteroatoms and from 2–9 carbon atoms which together with $B_2$ or $B_3$ contains 2 double bonds;

(93) $A_2$ is a chain containing 3 heteroatoms and from 1–8 carbon atoms which together with $B_2$ or $B_3$ contains 0 double bonds and $A_3$ is a chain containing 3 heteroatoms and from 1–8 carbon atoms which together with $B_2$ or $B_3$ contains 0 double bonds;

(94) $A_2$ is a chain containing 3 heteroatoms and from 2–8 carbon atoms which together with $B_2$ or $B_3$ contains 1 double bond and $A_3$ is a chain containing 3 heteroatoms and from 2–8 carbon atoms which together with $B_2$ or $B_3$ contains 0 double bonds;

(95) $A_2$ is a chain containing 3 heteroatoms and from 1–8 carbon atoms which together with $B_2$ or $B_3$ contains 2 double bonds and $A_3$ is a chain containing 3 heteroatoms and from 0–8 carbon atoms which together with $B_2$ or $B_3$ contains 0 double bonds;

(96) $A_2$ is a chain containing 3 heteroatoms and from 1–8 carbon atoms which together with $B_2$ or $B_3$ contains 1 double bond and $A_3$ is a chain containing 3 heteroatoms and from 1–8 carbon atoms which together with $B_2$ or $B_3$ contains 1 double bond;

(97) $A_2$ is a chain containing 3 heteroatoms and from 1–8 carbon atoms which together with $B_2$ or $B_3$ contains 2 double bonds and $A_3$ is a chain containing 3 heteroatoms and from 1–8 carbon atoms which together with $B_2$ or $B_3$ contains 1 double bond: and

(98) $A_2$ is a chain containing 3 heteroatoms and from 1–8 carbon atoms which together with $B_2$ or $B_3$ contains 2 double bonds and $A_3$ is a chain containing 3 heteroatoms and from 1–8 carbon atoms which together with $B_2$ or $B_3$ contains 2 double bonds.

Illustrative bicyclic ring structures which are encompassed by $R_1$, $R_4$ and $R_5$ in formula 1 included the following:

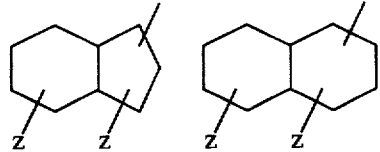

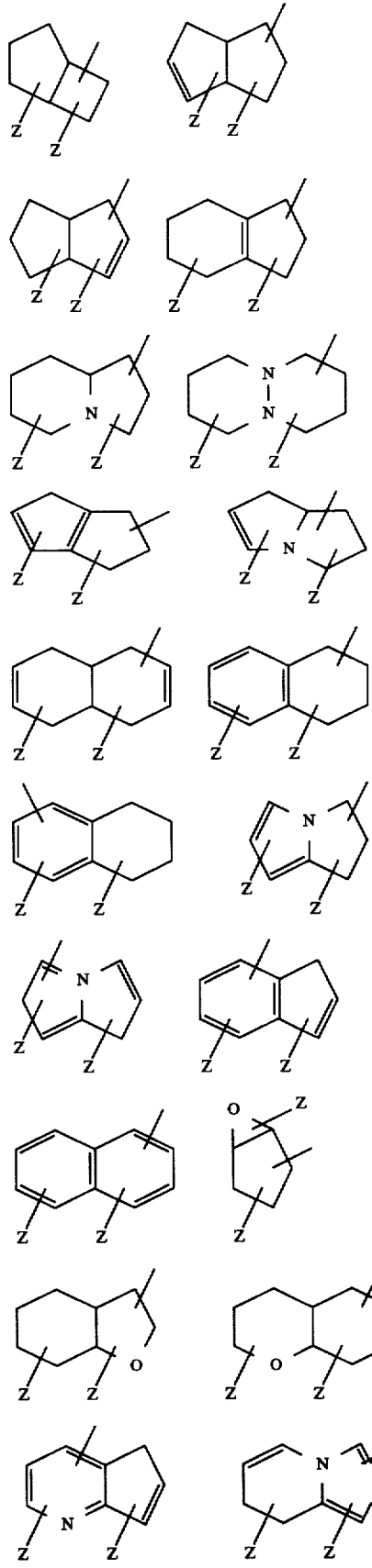

17
-continued
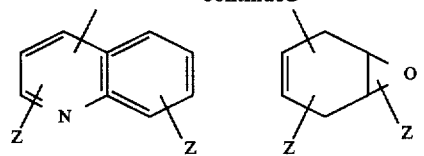
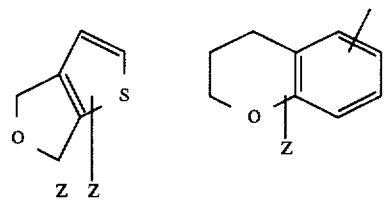
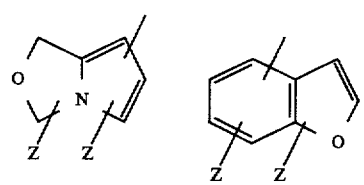
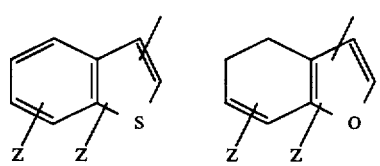
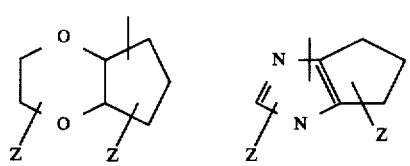
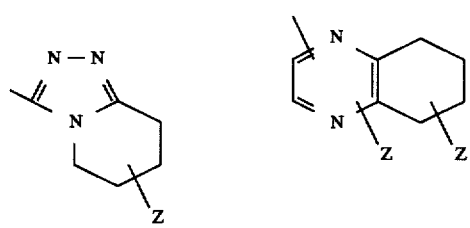
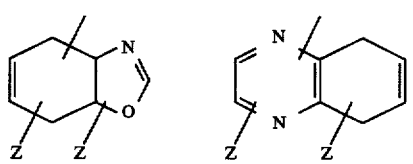
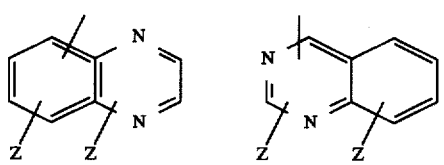
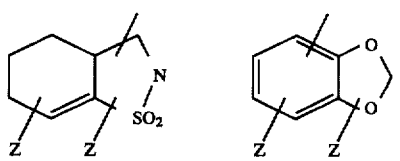
18
-continued
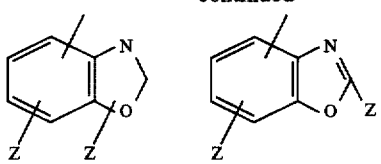
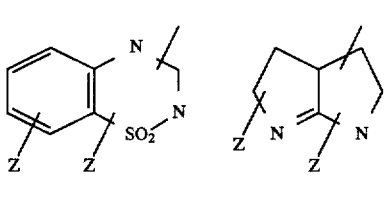
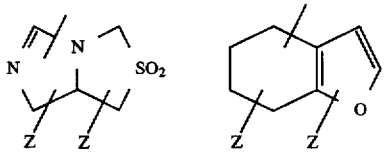
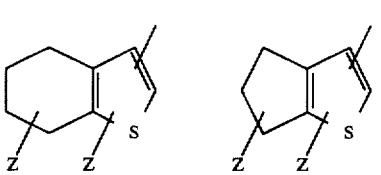
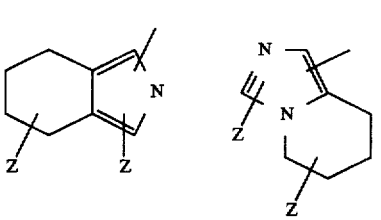
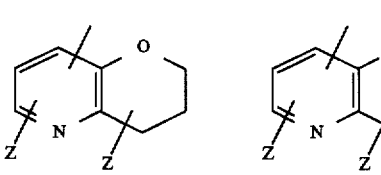
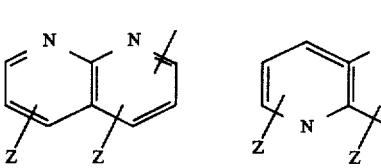
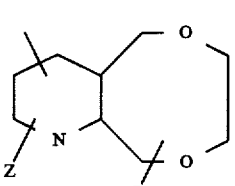
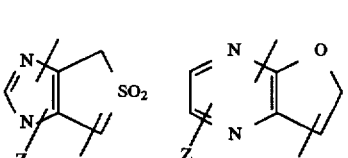

-continued

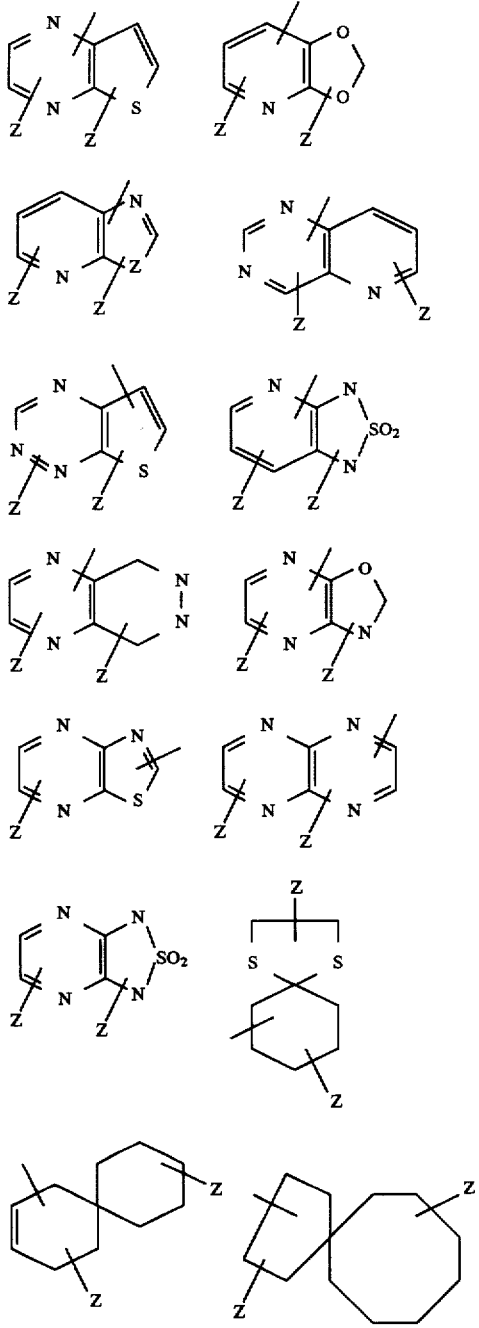

Polycyclic ring systems, i.e., greater than 2 rings, encompassed by $R_1$, $R_4$ and $R_5$ in formula 1 may be represented by generalized formulae 5, 6, 7 and 8 as follows:

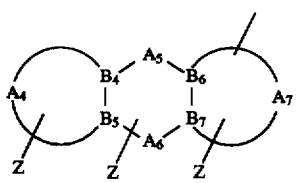

-continued

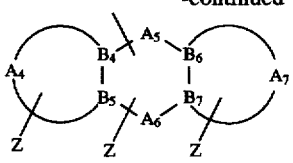

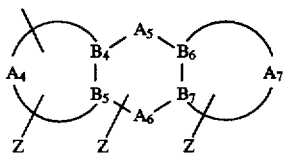

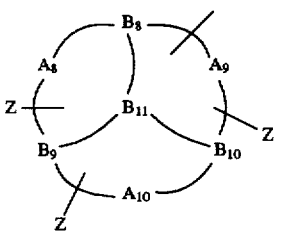

wherein $B_4$, $B_5$, $B_6$ and $B_7$ may be independently a saturated or unsaturated carbon atom or a saturated nitrogen atom, and $A_4$, $A_5$, $A_6$ and $A_7$ independently represent ring forming chains of atoms which may contain together with one or the other (but not both) of their two associated bridgehead atoms, from 0–2 double bonds. The groups Z represent one or more substituents selected independently from among the group of substituents defined for Z herein.

The ring-forming elements of $A_4$, $A_5$, $A_6$ and $A_7$ independent of $B_4$, $B_5$, $B_6$ and $B_7$ may contain entirely from 1–11 carbon atoms, may contain a combination of from 1–10 carbon atoms and from 1–3 heteroatoms which may be selected independently from among N, O, S, P or other heteroatoms, or may contain from 1–3 heteroatoms alone. Ring-forming heteroatoms may in some cases bear oxygen atoms as in aromatic N-oxides and ring systems containing the sulfinyl, sulfonyl, selenoxide and phosphono groups. The group $A_6$ may at times be defined as a bond. Selected carbon atoms contained in $A_4$, $A_5$, $A_6$ and $A_7$ may bear one or more carbonyl, thiocarbonyl or substituted or unsubstituted imino groups.

On structure 8 the groups $B_8$, $B_9$ and $B_{10}$ represent independently a saturated or unsaturated carbon atom or a saturated nitrogen atom. The group $B_{11}$ may represent a saturated or unsaturated carbon atom or a nitrogen or phosphorous atom. The groups $A_8$, $A_9$ and $A_{10}$ represent ring-forming chains of atoms which may contain together with 1 of the groups $B_8$, $B_9$, $B_{10}$ and $B_{11}$ from 0–2 double bonds.

The ring-forming elements of groups $A_8$, $A_9$ and $A_{10}$ independent of groups $B_8$, $B_9$, $B_{10}$ and $B_{11}$ may contain entirely from 2–10 carbon atoms, may contain from 1–10 carbon atoms in combination with 1–3 heteroatoms which may be selected independently from among N, O, S, P or other heteroatoms. or may contain from 2–3 heteroatoms alone. Ring-forming heteroatoms may in some cases bear oxygen atoms as in aromatic N-oxides and in ring systems containing the sulfinyl, sulfonyl, selenoxide and phosphono groups. Selected carbon atoms contained in groups $A_8$, $A_9$ and $A_{10}$ may bear one or more carbonyl, thiocarbonyl or substituted or unsubstituted imino groups.

It is recognized that polycyclic ring systems defined for $R_1$, $R_4$ and $R_5$ may be spirocyclic ring systems and are not limited to the fused polycyclic structures of formulae 5, 6, 7 and 8. Spirocyclic ring systems may be saturated or unsaturated, carbocyclic or heterocyclic and may be independently substituted by one or more substituents Z as defined herein.
Illustrative polycyclic ring structures which are encompassed by $R_1$, $R_4$ and $R_5$ in formula 1 include the following:
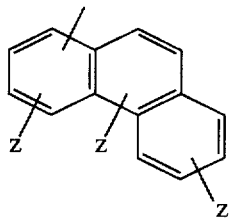
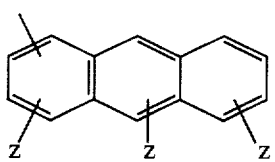
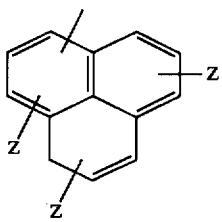
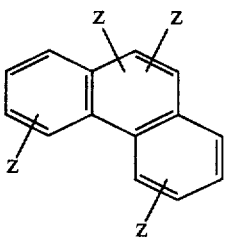
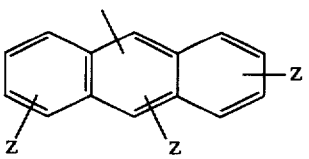
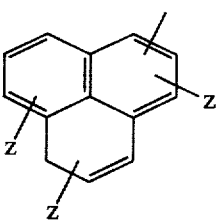
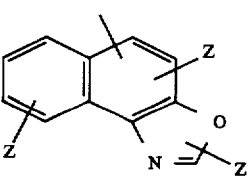
-continued
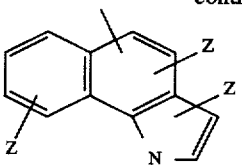
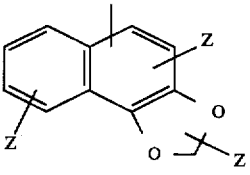
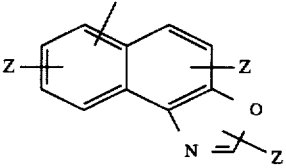
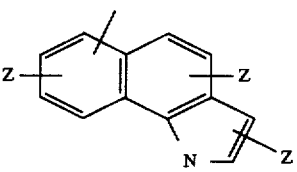
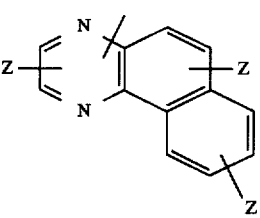
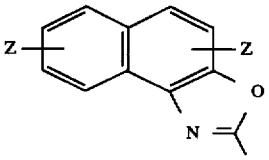
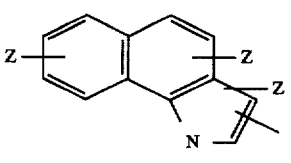
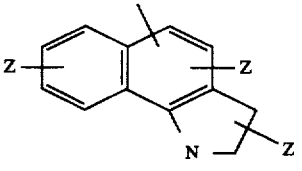
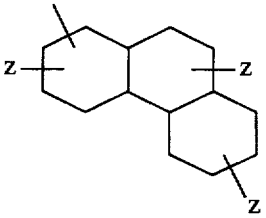

-continued

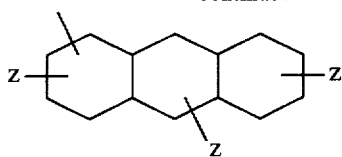
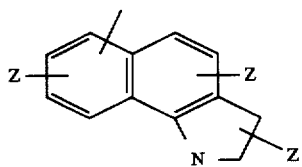
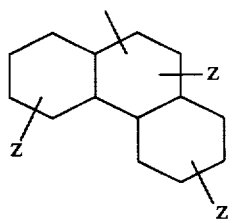
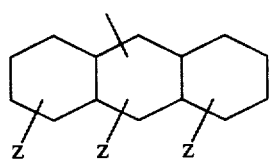
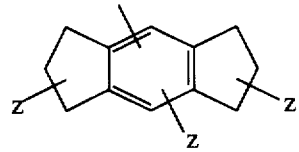
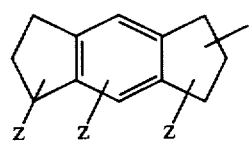
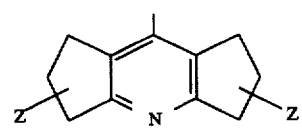
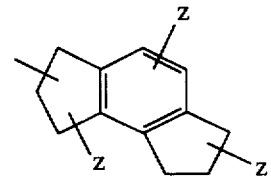
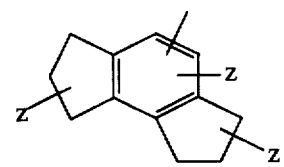

-continued

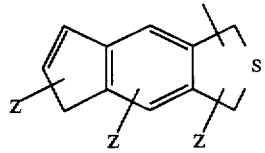
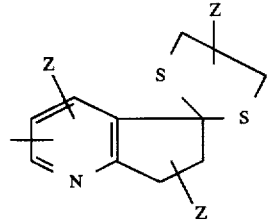
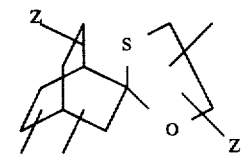
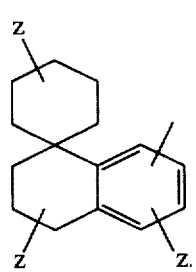

Bridged bycyclic structures encompassed by $R_1$, $R_4$ and $R_5$ in formula 1 may be represented by generalized formulae 9, 10, and 11 as follows:

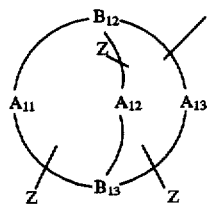

9

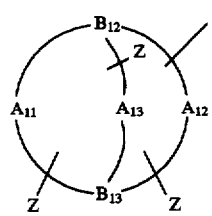

10

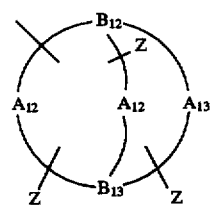

11 wherein $B_{12}$ and $B_{13}$ may be independently a saturated carbon atom optionally substituted by Z or a nitrogen atom, and the groups $A_{11}$, $A_{12}$ and $A_{13}$ independently represent ring-forming chains of atoms which may contain, independently of $B_{12}$ and $B_{13}$, from 0–2 double bonds. The groups Z represent one or more substituents selected independently from among the groups of substituents defined for Z herein.

The ring-forming elements of $A_{11}$, $A_{12}$ and $A_{13}$, independent of $B_{12}$ and $B_{13}$, may contain entirely from 1–11 carbon atoms, may contain a combination of from 1–10 carbon atoms and from 1–3 heteroatoms which may be selected independently from among N, O, S, P or other heteroatoms, or may contain from 1–3 heteroatoms alone with the proviso that when one of the groups $A_{11}$, $A_{12}$ and $A_{13}$ is a single heteroatom, the other two groups should contain two or more ring-forming atoms. A second proviso is that when one or both of the groups $B_{12}$ and $B_{13}$ is nitrogen, the groups $A_{11}$, $A_{12}$ and $A_{13}$ should contain at least two saturated ring-forming atoms.

Ring-forming heteroatoms may in some cases bear oxygen atoms as in the sulfinyl, sulfonyl, selenoxide and phosphono moieties. Selected carbon atoms contaned in $A_{11}$, $A_{12}$ and $A_{13}$ may bear one or more carbonyl, thiocarbonyl or substituted or unsubstituted imino groups.

Illustrative bridged bicyclic structures which are encompassed by $R_1$, $R_4$ and $R_5$ in formula 1 include the following:

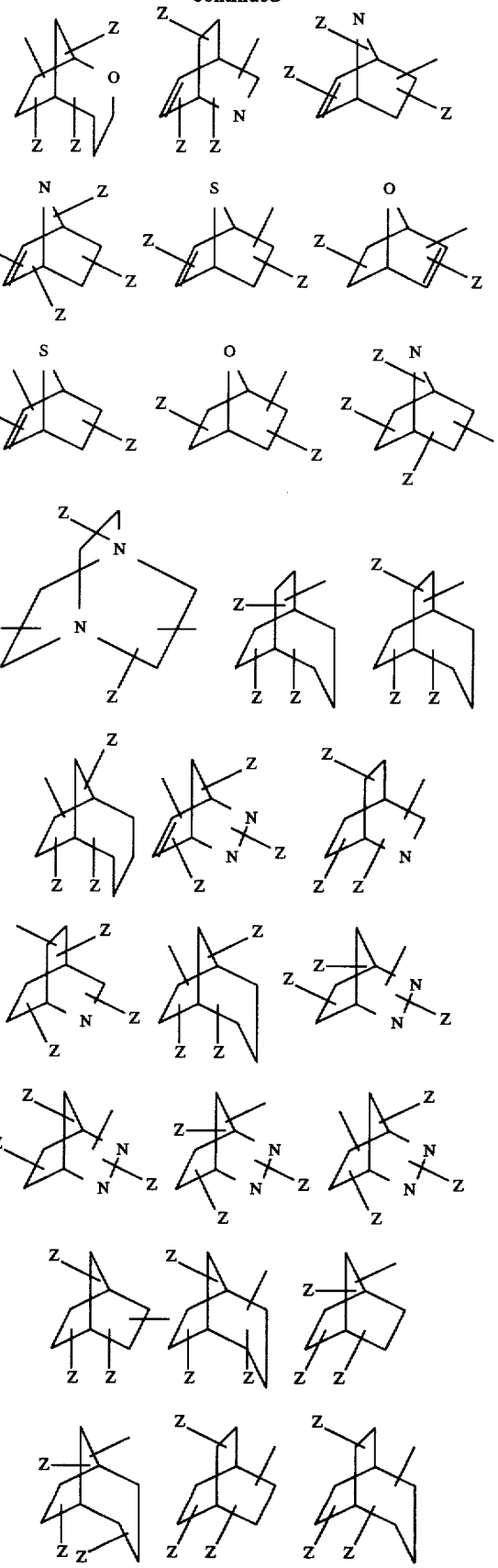

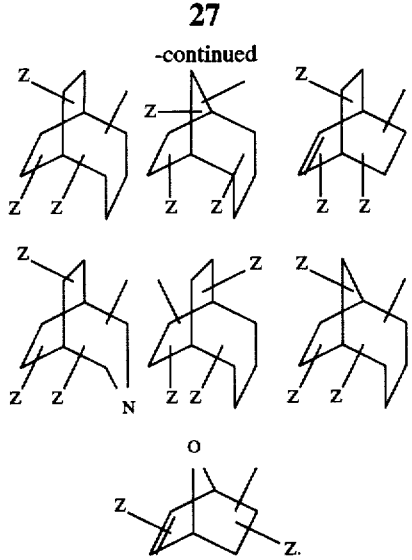

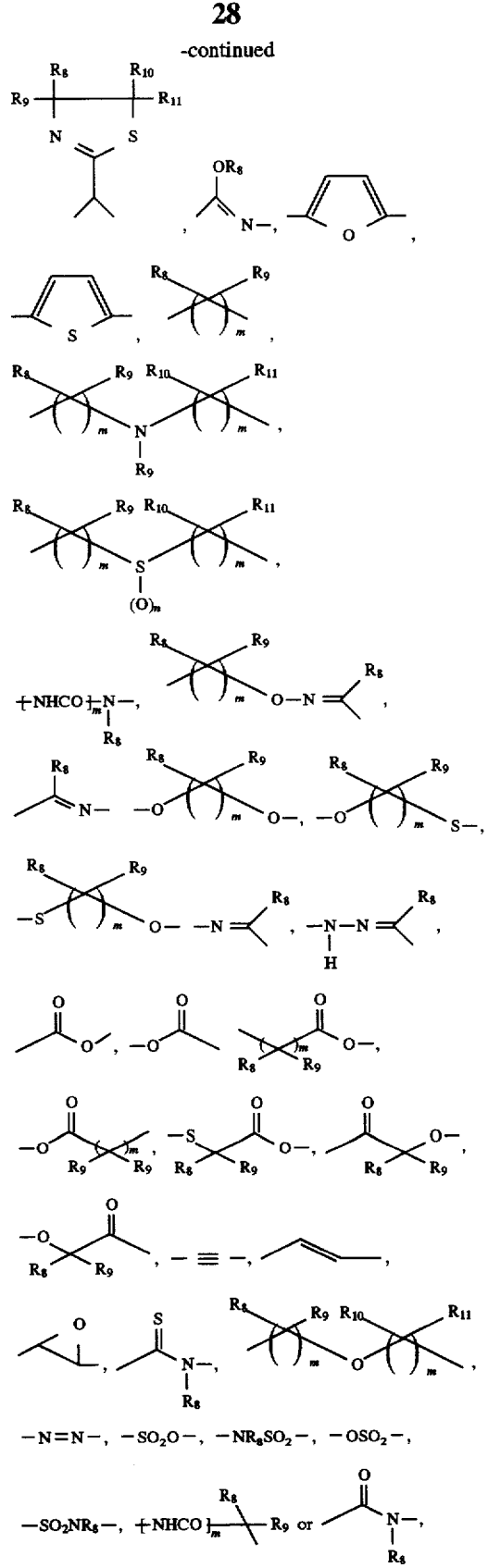

The substituent X may be an unsubstituted heteroatom such as an oxygen or sulfur, as in carbonyl and thiocarbonyl systems, or may be a substituted heteroatom or carbon atom. X may also be a covalent single or double bond, or an array of atoms serving to join the ring system $R_5$ to the remainder of the acyl urea molecule. The group X may be joined to the ring system $R_5$ by means of a single or double bond. Likewise, X may be attached to the remainder of the acyl urea molecule by means of a double or single bond. X may be a saturated or unsaturated, branched or straight chain of carbon atoms; a branched or straight, saturated or unsaturated chain of atoms consisting of both carbon atoms and heteroatoms; or may be a branched or straight, saturated or unsaturated chain consisting entirely of heteroatoms. Selected heteroatomic components of X may bear oxygen atoms as in the case of groups containing the sulfonyl, sulfinyl, N-oxide and phosphono moieties. Selected heteroatomic components of X may bear one or more substituents Z as defined herein. Selected carbon atoms participating in X may bear carbonyl, thiocarbonyl, substituted or unsubstituted imino, substituted or unsubstituted alkylidene or one or more substituents Z as defined herein.

Illustrative structures which are encompassed by substituent X include the following:

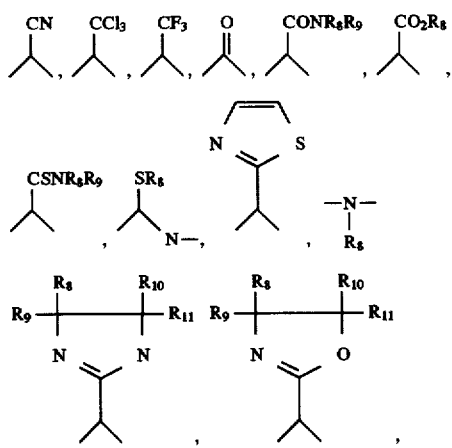

wherein m is a value of from 0 to 8, n is a value of from 0 to 2, and $R_8$, $R_9$, $R_{10}$ and $R_{11}$ are independently hydrogen or substituted or unsubstituted alkyl, polyhaloalkyl, phenyl or benzyl in which the permissible substituents are as defined for Z herein.

$R_2$ and $R_3$ may be linked together to form a heterocyclic saturated or unsaturated ring system. This ring system may be part of a saturated or unsaturated, aromatic or nonaromatic, carbo- or hetero-, bicyclic or polycyclic ring system. Illustrative of suitable heteroatoms include oxygen, sulfur, nitrogen, silicon and phosphorous. The ring system can be optionally substituted with one or more of the substituents Z as defined herein.

Illustrative linking structures which are encompassed by $R_2$ and $R_3$ of formula 1 include the following:

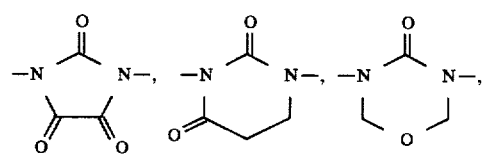

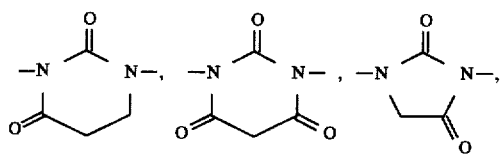

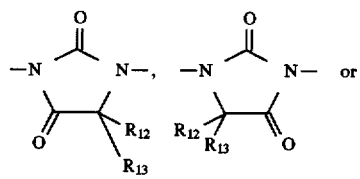

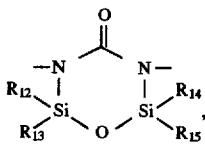

wherein $R_{12}$, $R_{13}$, $R_{14}$ and $R_{15}$ are independently hydrogen, halogen, or substituted or ubstituted alkyl polyhaloalkyl, phenyl or benzyl which the permissible substituents are as defined Z herein.

It is recognized that the acyl urea linkage formula 1 may be converted to different forms including the following:

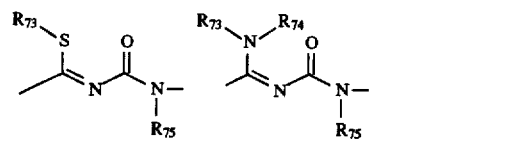

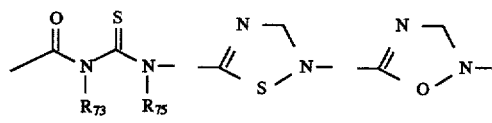

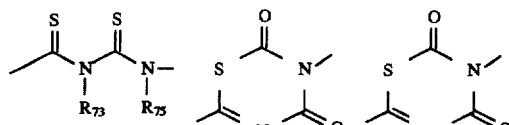

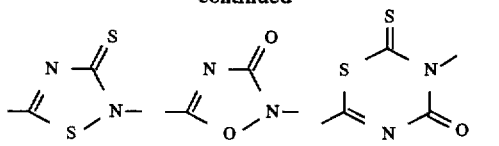

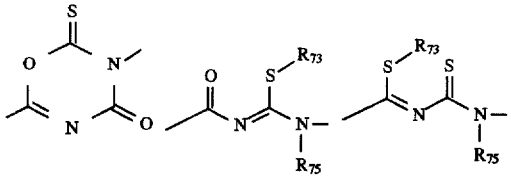

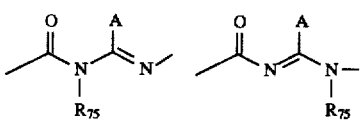

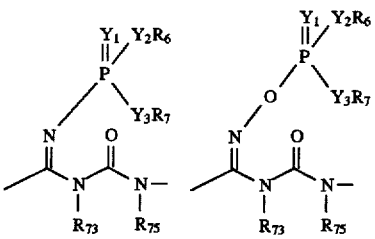

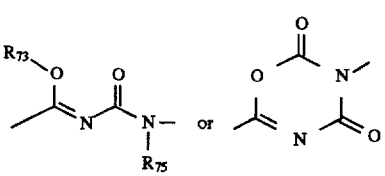

wherein $R_{73}$, $R_7$ and $R_7$ are independently hydrogen, alkyl, substituted alkyl in which the permissible substituents are the same or different and are one or more halogen, alkoxy, alkylthio or cyano; cycloalkyl, cycloalkenyl, substituted benzyl in which the permissible substituents are the same or different and are one or more halogen, hydroxy, nitro, cyano, alkyl, polyhaloalkyl, alkoxy or polyhaloalkoxy; hydroxy, alkoxy, polyhaloalkoxy, alkylthio, polyhaloalkylthio; acyl, alkoxycarbonyl, alkoxythiocarbonyl, alkylsulfonyl, substituted phenylsulfonyl in which the permissible substituents are the same or different and are one or more halogen, nitro, cyano or alkyl; substituted phenylthio in which the permissible substitutents are the same or different and are one or more halogen, alkyl, nitro, cyano, polyhaloalkyl, or substituted or unsubstituted alkoxycarbonyl, alkenoxycarbonyl, alkynoxycarbonyl, cycloalkoxycarbonyl, phenoxycarbonyl, hydroxycarbonyl or the alkali metal salt or ammonium salt thereof, alkyl, alkoxy, alkylthio, cycloalkyl, cycloalkyloxy, cycloalkylthio, alkenyl, alkenylthio, alkanoyl, alkylsulfonyl, alkynyl, phenyl, phenoxy, phenylthio or amino; N-(alkylcarbonyl)-N-alkylaminothio, alkoxycarbonylthio, trialkylsilyl, dialkylarylsilyl, triarylsilyl and

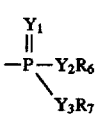

wherein $Y_1$, $Y_2$, $Y_3$, $R_6$ and $R_7$ are as defined herein; and A can be —$SSR_7$, 1-benzimidazolyl, 1-benztriazolyl and 1-pyrazolyl which can be substituted with one or more substituents Z defined herein. A can also be 1-diazolyl or 1-imidazolyl optionally substituted with alkyl. Such modifications and embodiments can be made without departing from the spirit and scope of this invention.

It is readily apparent that formula 1 encompasses a wide variety of urea compounds as more particularly described hereinbelow. For example, U.S. Pat. No. 4,426,385, incorporated herein by reference, discloses and claims bicyclooxyphenyl urea compounds which are encompassed by the above formula 1 and which may be used in the method of this invention. Such bicyclooxyphenyl urea compounds can be prepared by the methods described in U.S. Pat. No. 4,426,385, and are available from Union Carbide Agricultural Products Company, Inc., Research Triangle Park, N.C. Illustrative of the bicyclooxyphenyl urea compounds of U.S. Pat. No. 4,426,385 which may be useful in the method of this invention include the following:

1-[4-(4-chloro-1-naphthoxy)-3,5-dichlorophenyl]-3-(2,6-difluorobenzoyl)urea;
1-[4-(4-chloro-1-naphthoxy)-3,5-dichlorophenyl]-3-(2-chlorobenzoyl)urea:
1-[4-(4-chloro-1-naphthoxy)-3,5-dichlorophenyl]-3-(2-chloro-6-fluorobenzoyl)urea;
1-[4-(4-chloro-1-naphthoxy)-3-methylphenyl]-3-(2,6-difluorobenzoyl)urea:
1-[4-(4-chloro-1-naphthoxy)-3-methylphenyl]-3-(2-chlorobenzoyl)urea;
1-[4-(4-chloro-1-naphthoxy)-3-methylphenyl]-3-(2-chloro-6-fluorobenzoyl)urea;
1-[4-(4-chloro-5,6,7,8-tetrahydro-1-naphthoxy)-2-methyl-5-chlorophenyl]-3-(2,6-difluorobenzoyl)urea:
1-[4-(4-chloro-5,6,7,8-tetrahydro-1-naphthoxy)-2-methyl-5-chlorophenyl]-3-(2-chlorobenzoyl)urea;
1-[4-(4-chloro-5,6,7,8-tetrahydro-1-naphthoxy)-2-methyl-5-chlorophenyl]-3-(2-fluorobenzoyl)urea:
1-[4-(4-chloro-1-naphthoxy)-2,5-dimethyl-3-chlorophenyl]-3-(2,6-difluorobenzoyl)urea:
1-[4-(4-chloro-1-naphthoxy)-2,5-dimethyl-3-chlorophenyl]-3-(2-chlorobenzoyl)urea;
1-[4-(4-chloro-1-naphthoxy)-2,5-dimethyl-3-chlorophenyl]-3-(2-fluorobenzoyl)urea;
1-[4-(4-chloro-1-naphthoxy)-2,5-dimethyl-3-chlorophenyl]-3-(2-chloro-6-fluorobenzoyl)urea;
1-[4-(4-dimethylamino-5,6,7,8-tetrahydro-1-naphthoxy)-2,5-dimethyl-3-chlorophenyl]-3-(2,6-difluorobenzoyl) urea;
1-[4-(4-dimethylamino-5,6,7a8-tetrahydro-1-naphthoxy)-2,5-dimethyl-3-chlorophenyl]-3-(2-chlorobenzoyl)urea;
1-[4-(4-dimethylamino-5,6,7,8-tetrahydro-1-naphthoxy)-2,5-diemthyl-3-chlorophenyl)-3-(2-fluorobenzoyl)urea;
1-[2,3,5-trichloro-4-[4-chloro-1-naphthoxy]phenyl]-3-(2-chlorobenzoyl)urea;
1-[2,3,5-trichloro-4-(4-chloro-1-naphthoxy)phenyl]-3-(2-fluorobenzoyl)urea;
1-[3,5-dimethyl-4-(4-chloro-1-naphthoxy)phenyl]-3-(2,6-difluorobenzoyl)urea:
1-[3,5-dimethyl-4-(4-chloro-1-naphthoxy)phenyl]-3-(2-chlorobenzoyl)urea;
1-[3,5-dimethyl-4-(4-chloro-1-naphthoxy)phenyl]-3-(2-fluorobenzoyl)urea;
1-(3,5-dimethyl-4-(4-chloro-1-naphthoxy)phenyl]-3-(2-chloro-6-fluorobenzoyl)urea;
1-(2a5-dimethyl-3-chloro-4-(4-chloro-5,6,7,8-tetrahydro-1-naphthoxy)-3-(2,6-difluorobenzoyl)urea:
1-(2,5-dimethyl-3-chloro-4-(4-chloro-5,6,7,8-tetrahydro-1-naphthoxy)-3-(2-chlorobenzoyl)urea;
1-(2,5-dimethyl-3-chloro-4-(4-chloro-5,6,7,8-tetra-hydro-1-naphthoxy)-(2-chloro-6-fluorobenzoyl)urea;
1-[3-methyl-4-(4-chloro-1-naphthoxy)phenyl]-3-(2,6-difluorobenzoyl)urea:

1-(3-methyl-4-(4-chloro-1-naphthoxy)phenyl]-3-(2-chloro-6-fluorobenzoyl)urea;
1-(3-methyl-4-(4-chloro-1-naphthoxy)phenyl]-3-(2-chlorobenzoyl)urea;
1-(3,5-dichloro-4-[4-nitro-1-naphthoxyjphenyl)-3-(2-chloro-6-fluorobenzoyl)urea;
1-(3,5-dichloro-4-[4-cyano-1-naphthoxylphenyl)-3-(2-chloro-6-fluorobenzoyl)urea;
1-(3,5-dichloro-4-[4-trifluoromethyl-1-naphthoxy] phenyl)-3-(2-chloro-6-fluorobenzoyl)urea;
1-(3,5-dichloro-4-[2,2-dimethyl-2,3-dihydro-4-trifluoromethyl-7-benzofuranyloxy]phenyl)-3-(2-chloro-6-fluorobenzoyl)urea;
1-(3,5-dichloro-4-[4-nitro-5,6,7,8-tetrahydro-1-naphthoxy]-phenyl)-3-(2-chloro-6-fluorobenzoyl) urea;
1-(3,5-dichloro-4-[4-benzothienyloxy]phenyl)-3-(2-chloro-6-fluorobenzoyl)urea;
1-(3-chloro-5-n-pentyl-4-[2-trifluoromethyl-7-triflioromethylsulfinyl-4-benzodioxalanyloxy]phenyl)-3-(2,6-dichlorobenzoyl)urea;
1-(4-[2-chloro-4-nitro-5-oxo-5,6,7,8-tetrahydro-1-naphthoxy]-3,5-dibromophenyl)-3-(2,6-dichlorobenzoyl) urea;
1-(3,5-difluoro-4-[4-phenylsulfinyl-1-naphthoxy] phenyl)-3-(2,6-difluorobenzoyl)urea;
1-(3,5-dichloro-4-[2,3-dihydro-2,2-dimethyl-7-benzofuranyloxy]phenyl)-3-(2,6-difluorobenzoyl)urea:
1-(3,5-dichloro-4-[4-chloro-2,3-dihydro-2,2-dimethyl-7-benzofuranyloxy]phenyl)-3-(2-chlorobenzoyl)urea;
1-(4-[4-chloro-1-naphthoxy]-3,5-dichlorophenyl)-3-([2,4-dichloro-3-pyridinyl]carbonyl)urea;
1-(4-[2,4-dichloro-1-naphthoxy]-3,5-dichlorophenyl)-3-([3-trifluoromethyl-2-pyra2inyl]carbonyl)urea;
1-(4-[1,6-dichloro-2-naphthoxyl-3-chlorophenyl)-3-([2-pyrisidinyl]carbonyl)urea;
1-(4-[4-chloro-1-naphthoxy]-3,5-dichlorophenyl)-3-([5-chloro-4-pyrimidinyl]carbonyl)urea:
1-(4-[4-chloro-1-naphthoxy]phenyl)-3-(2,6-difluorobenzoyl)urea:
1-(4-[4-chloro-1-naphthoxy]-3-chlorophenyl)-3-(2,6-difluorobenzoyl)urea;
1-(4-[1-naphthoxy]-3-chlorophenyl)-3-(2,6-dichlorobenzoyl)urea;
1-(4-[2-naphthoxy]-phenyl)-3-(2-chloro-6-fluoro-benzoyl) urea;
1-(3,5-dichloro-4-[4-methoxy-1-naphthoxy]phenyl)-3-(2-chloro-6-fluorobenzoyl)urea;
1-(3-chloro-4-[4-chloro-1-naphthoxy]-2,5-dimethyl-phenyl)-3-(2,6-difluorobenzoyl)urea;
1-(3-chloro-4-[4-chloro-1-naphthoxy]-2,5-dimethyl-phenyl)-3-(2-chlorobenzoyl)urea;
1-(3-chloro-4-[4-chloro-1-naphthoxyl-2,5-dimethyl-phenyl)-3-(2-chloro-6-fluorobenzoyl)urea;
1-(4-[4-chloro-5,6,7,8-tetrahydro-1-naphthoxy]-3,5-dimethylphenyl)-3-(2,6-difluorobenzoyl)urea:
1-(3-chloro-4-[4-chloro-5,6,7,8-tetrahydro-1-naphthoxy]-5-methylphenyl)-3-(2,6-difluorobenzoyl) urea:
1-(4-[4-chloro-5,6,7,8-tetrahydro-1-naphthoxy]-3,5-dichlorophenyl)-3-(2-chlorobenzoyl)urea;
1-(3,5-dichloro-4-[4-dimethylamino-5,6,7,8-tetra-hydro-1-naphthoxy]phenyl)-3-(2-chloro-6-fluorobenzoyl)urea;
D14317-2 8303V
1-(3-chloro-4-[4-chloro-5,6,7,8-tetrahydro-1-naphthoxy]-S-methylphenyl)-3-(2,6-difluorobenzoyl) urea:
1-(3-chloro-4-[4-dimethylamino-5,6,7,8-tetrahydro-1-naphthoxy]-5-methylphenyl)-3-(2-chloro-6-fluorobenzoyl) urea:

1-(3,5-dimethyl-4-[4-dimethylamino-5,6,7,8-tetrahydro-1-naphthoxy[]phenyl)-3-(2-chloro-6-fluorobenzoyl)urea;
1-(3-chloro-5-methyl-4-[4-chloro-1-naphthoxy)phenyl)-3-(2,6-difluorobenzoyl)urea:
1-(3-methyl-4-[4-chloro-1-napthoxy]phenyl)-3-(2,6-difluorobenzoyl)urea;
1-(3,5-dichloro-4-[4-chloro-1-naphthoxy]phenyl)-3-(2,6-difluorobenzoyl)urea;
1-(2-methyl-4-[4-chloro-1-naphthoxy]-5-chlorophenyl)-3-(2,6-difluorobenzoyl)urea:
1-(3-trifluoromethyl-4-[4-chloro-1-naphthoxy]phenyl)-3-(2,6-difluorobenzoyl)urea;
1-(3-chloro-4-[4-chloro-1-naphthoxy]phenyl)-3-(2,6-difluorobenzoyl)urea;
1-(3,5-dimethyl-4-[4-chloro-1-naphthoxy]phenyl)-3-(2,5-difluorobenzoyl)urea;
1-(2,3,5-trichloro-4-[4-chloro-1-naphthoxyaphenyl)-3-(2,6-difluorobenzoyl)urea;
1-(2-methyl-3-chloro-4-[4-chloro-1-naphthoxyl-5-difluoromethyl-phenyl)-3-(2,6-difluorobenzoyl)urea;
1-(2-methyl-3-chloro-4-[4-chloro-1-naphthoxyl-5-carboxyphenyl)-3-(2,6-difluorobenzoyl)urea;
1-(4-[4N-ethyl-N-phenylsulfamido-5,6,7,8-tetrahydro-1-naphthoxy)phenyl)-
1-(2-methoxy-6-methylbenzoyl)urea;
1-(3,5-difluoro-4-[4-phenylsulfinyl-1-naphthoxy] phenyl)-3-(2,6-difluorobenzoyl)urea; D14317–2 8303V
1-(3-dichloromethyl-4-[4-phenylsulfonyl-1-naphthoxy]phenyl)-3-(2-trifluoromethylbenzoyl)urea;
1-(3,5-dichloro-4-[4-chloro-1-naphthoxy]phenyl)-N-methyl-N'-methyl-3-(2,6-dichlorobenzoyl)urea:
1-(4-[4-N-(4-chlorophenyl)sulfamido-1-naphthoxy]-iodo-5-methylphenyl)-3-(2-trichloromethoxybenzoyl) urea:
1-(3,5-dichloro-4-[4-chloro-1-naphthoxy]phenyl-3-(2-chloro-6-nitrobenzoyl)urea:
1-(4-[7–2,4-dichlorophenylsulfenyl-3-isopropoxy-5-benzofuranyloxy]phenyl)-3-(2-ethoxybenzoyl)urea:
1-(3-methoxy-4-[4-chloro-1-naphthoxy]phenyl-3-(2,6-difluorobenzoyl)urea;
1-(3-perfluoroisoproxy-4-[2,2,6-trimethyl-4-benzodioxalanyloxy]phenyl-3-(2-iodobenzoyl)urea;
1-(3-chloro-4-[2-chloro-4-ethylsulfenyl-1-naphthoxy]phenyl)-3-(2-chlorobenzoyl)urea; 1-(3-chlorodifluoromethyl-4-[5,8-dichloro-4-trichloromethylsulfenyl-1-naphthoxy]phenyl)-3-(2-chlorobenzoyl) urea:
1-(3,5-dichloro-4-[4-methylsulfinyl-5,6,7,8-tetrahydro-1-naphthoxy]phenyl)-3-(2,6-dichlorobenzoyl) urea; and
1-(4-[4-N-(4-nitrophenyl)-N-isopropyl-sulfamido-5,6,7,8-tetrahydro-1-naphthoxy]phenyl)-3-(2-chloro-6-methylbenzoyl)urea.

U.S. patent application Ser. No. 495,331, filed May 20, 1983, incorporated herein by reference, abandoned grandparent application to U.S. Pat. No. 4,880,838, discloses and claims 1-(alkylphenoxyaryl)-3-benzoyl urea compounds which may be used in the method of this invention. Such 1-(alkylphenoxyaryl)-3-benzoyl urea compounds can be prepared by the methods described in the application, and are available from Union Carbide Agricultural Products Company, Inc., Research Triangle Park, N.C. Illustrative of the 1-(alkylphenoxyaryl)-3-benzoyl urea compounds of U.S. patent application Ser. No. 495,331, abandoned grandparent application to U.S. Pat. No. 4,880, 838, which may be useful in the method of this invention include the following:
1-(2,5-dimethyl-3-chloro-4-(2,5-dimethyl-4-chlorophenoxy)phenyl3–3-(2-chlorobenzoyl)urea;
1-[2,5-dimethyl-3-chloro-4-(2,5-dimethyl-4-chlorophenoxy)phenyl)-3-(2-fluorobenzoyl)urea:

1-[4-(2,3-dimethyl-4-bromophenoxy)-2,5-dimethyl-3-chlorophenyl]-3-(2,6-difluorobenzoyl)urea;
1-[4-(2,3-dimethyl-4-bromophenoxy)-2,5-dimethyl-3-chlorophenyl]-3-(Z chloro-6-fluorobenzoyl)urea:
1-(4-(2-methyl-3,4-dichlorophenoxy)-3,6-dimethyl-5-chlorophenyl]-3-(2,6-difluorobenzoyl)urea:
1-(4-(2-methyl-3,4-dichlorophenoxy)-3,6-dimethyl-5-chlorophenyl]-3-(2-chlorobenzoyl)urea;
1-[4-(2-methylphenoxy)-3,6-dimethyl-5-chlorophenyl]-3-(2,6-difluorobenzoyl)urea:
1-[4-(2-methylphenoxy)-3,6-dimethyl-5-chlorophenyl]-3-(2,6-dichlorobenzoyl)urea:
1-[4-(2-methylphenoxy)-3,6-dimethyl-5-chlorophenyl]-3-(2-chlorobenzoyl)urea;
1-(4-(2-methylphenoxy)-3,6-dimethyl-5-chlorophenyl]-3-(2-chlorobenzoyl)thiourea;
1-[4-(2-methylphenoxy)-3,6-dimethyl-5-chlorophenyl]-3-(2-methylbenzoyl)thiourea:
1-[4-(2-methylphenoxy)-2,3,5,6-tetramethylphenyl]-3-(2,6-dimethylbenzoyl)urea:
1-[4-(2-methylphenoxy)-2,3,5,6-tetramethylphenyl]-3-(2,6-methylbenzoyl)thiourea:
1-[4-(2-methylphenoxy)-2,3,5,6-tetramethylphenyl]-3-(2,6-difluorobenzoyl)urea;
1-[4-(2-methylphenoxy)-2,3,5,6-tetramethylphenyll-3-(2,6-dichlorobenzoyl)urea;
1-[4-(2-methylphenoxy)-2,3,5-trimethylphenyl]-3-(2,6-dichlorobenzoyl)urea:
1-[4-(2-methylphenoxy)-3,5-dichlorophenyl]-3-(2,6-difluorobenzoyl)urea:
1-(4-(2-methyl-4-bromophenoxy)-3,6-dimethyl-5-chlorophenyll-3-(2,6-difluorobenzoyl)urea;
1-[4-(2-methyl-4-bromophenoxy)-3,6-dimethyl-5-chlorophenyl]-3-(2-chlorobenzoyl)urea:
1-(4-(2-methyl-4-bromophenoxy)-3,6-dimethyl-5-chlorophenyl3–3-(2-chlorobenzoyl)thiourea;
1-(4-(2-methyl-4-bromophenoxy)-3,6-dimethyl-5-chlorophenyll-3-(2-methylbenzoyl)thiourea:
1-[4-(2-methyl-4-bromophenoxy)2,3,5,6-tetramethylphenyl]-3-(2,6-difluorobenzoyl)urea;
1-[4-(2-methyl-4-bromophenoxy)-2,3,5-tetramethylphenyl]-3-(2,6-difluorobenzoyl)urea,
1-(4-(2-methyl-4-bromophenoxy)-3,5-dimethylphenyl]-3-(2,6-difluorobenzoyl)urea;
1-[4-(2-methyl-4-bromophenoxy)-3,5-dichlorophenyll-3-(2-chlorobenzoyl)urea;
1-[4-(2-bromo-4-methylphenoxy)-3U6-dimethyl-5-chlorophenyl]-3-(2,6-difluorobenzoyl)urea;
1-[4-(2-bromo-4-methylphenoxy)-3,6-dimethyl-5-chlorophenyl]-3-(2-chlorobenzoyl)urea;
1-[4-(2-bromo-4-methylphenoxy-2,3,5,6-tetramethylphenyl]-3-(2-chlorobenzoyl)urea;
1-[4-(2-bromo-4-methylphenoxy)-3,5-dichlorophenyl]-3-(2,6-difluorobenzoyl)urea;
1[4-(2-bromo-4-methylphenoxy)-3,5-dimethylphenyl]-3-(2-methylbenzoyl)thiourea:
1-(4-(2-methyl-4-t-butylphenoxy)3,6-dimethyl-5-chlorophenyl]-3-(2,6-difluorobenzoyl)urea;
1-[4-(2-methyl-4-t-butylphenoxy)-2,6-dimethyl-5-chlorophenyl]-3-(2-chlorobenzoyl)urea;
1-[4-(2-methyl-4-t-butylphenoxy)-2,3,5,6-tetramethylphenyl]-3-(2,6-difluorobenzoyl)urea;
1-[4-(2-methyl-4-t-butylphenoxy)-3,5-dichlorophenyl]-3-(2-methylbenzoyl)thiourea:
1-[4-(2-methyl-4-t-butylphenoxy)-2,5-dimethyl-3-chlorophenyll-3-(2,6-difluorobenzoyl)urea;
1-(4-(2-methyl-4-t-butylphenoxy)-2,5-dimethyl-3-chlorophenyll-3-(2-fluorobenzoyl)urea:

1-[4-(2-methyl-4-t-butylphenoxy)-2,5-dimethyl-3-chlorophenyl]-3-(2,6-dichlorobenzoyl)urea;
1-(4-(2-methyl-4-t-butylphenoxy)-2,5-dimethyl-3-chlorophenyl]-3-(2-chlorobenzoyl)urea:
1-[4-(2-methyl-4-chlorophenoxy)-3,6-dimethyl-5-chlorophenyl]-3-(2,6-difluorobenzoyl)urea;
1-[4-(2-methyl-4-chlorophenoxy)-3,5-dichlorophenyl]-3-(2-methylbenzoyl)thiourea:
1-[4-(2-methyl-4-chlorophenoxy)-2,3,5,6-tetramethyl-phenyl]-3-(2,6-difluorobenzoyl)urea;
1-[4-(2-methyl-4-chlorophenoxy)-3,6-dimethyl-5-chlorophenyl]-3-(2,6-dimethoxybenzoyl)urea:
1-[4-(4-nonylphenoxy)-3,6-dimethyl-5-chlorophenyl]-3-(2,6-difluorobenzoyl)urea;
1-[4-(4-nonylphenoxy)-2,3,5,6-tetramethylphenyl]-3-(2-chlorobenzoyl)thiourea;
1-[4-(4-nonylphenoxy)-3,5-dichlorophenyl]-3-(2,6-difluorobenzoyl)urea;
1-[4-(4-nonylphenoxy)-3,5-dimethylphenyl]-3-(2-methylbenzoyl)urea:
1-[4-(2-chloro-4-methylphenoxy)-3,6-dimethyl-5-chlorophenyl]-3-(2,6-difluorobenzoyl)urea;
1-[4-(2-chloro-4-methylphenoxy)-3,6-dimethyl-5-chlorophenyl]-3-(2-chlorobenzoyl)thiourea:
1-[4-(2-chloro-4-methylphenoxy)-3,5-dichlorophenyl]-3-(2,6-difluorobenzoyl)urea:
1-[4-(2-chloro-4-methylphenoxy)2,3,5,6-tetramethyl-phenyl]-3-(2,6-difluorobenzoyl)urea;
1[4-(3,4,5-trimethylphenoxy)-3,6-dimethyl-5-chlorophenyl]-3-(2,6-difluorobenzoyl)urea;
1-[4-(3,4,5-trimethylphenoxy)-3,6-dimethyl-5-chlorophenyl]-3-(2-chlorobenzoyl)thiourea:
1-[4-(3,4,5-trimethylphenoxy)-2,3,5,6-tetramethyl-phenyl]-3-(2-methylbenzoyl)thiourea;
1-[4-(3,4,5-trimethylphenoxy)-3,5-dichlorophenyl]-3-(2,6-difluorobenzoyl)urea:
1-[4-(2,3,5-trimethylphenoxy)-3,6-dimethyl-5-chlorophenyl]-3-(2,6-dimethoxybenzoyl)urea:
1-[4-(2,3,5-trimethylphenoxy)-2,3,5,6-tetramethyl-phenyl]-3-(2,6-difluorobenzoyl)urea;
1-[4-(2,3,5-trimethylphenoxy)-3-i-propylphenyl)-3-(2-methylbenzoyl)thiourea;
1-[4-(2,3,5-trimethylphenoxy)-3-trifluoromethylphenyl]-3-(2,6-difluorobenzoyl)urea;
1-[4-(2-methyl-4-trifluoromethylphenoxy)-3,6-dimethyl-5-chlorophenyl]-3-(2,6-difluorobenzoyl)urea:
1-[4-(2-methyl-4-trifluoromethylphenoxy)-3,6-dimethyl-5-chlorophenyl]-3-(2-chlorobenzoyl)thiourea:
1-[4-(2-methyl-4-trifluoromethylphenoxy)-3,5-dichlorophenyl]-3-(2,6-dimethoxybenzoyl)urea;
1-[4-(2-methyl-4-trifluoromethylphenoxy)-2,3,5-trimethylphenyl]-3-(2-methylbenzoyl)thiourea;
1-[4-(2,4-dimethylphenoxy)2,3,6-trimethylphenyl]-3-(2-chlorobenzoyl)urea;
1-[4-(395-dimethylphenoxy)-2,6-dimethylphenyl]-3-(2,6-difluorobenzoyl)urea:
1-[4-(2-methyl-4-methoxyphenoxy)-3,6-dimethyl-5-chlorophenyl]-3-(2,6-difluorobenzoyl)urea:
1-[4-(2-methyl-4-dimethylaminophenoxy)-3,6-dimethyl-5-chlorophenyl]-3-(2,6-difluorobenzoyl)urea:
1-[4-(2-methyl-4-methylthiophenoxy)-3,6-dimethyl-5-chlorophenyl]-3-(2z6-difluorobenzoyl)urea;
1-[4-(2-methyl-4-methylsulfonylphenoxy)-3,6-dimethyl-5-chlorophenyl]-3-(2,6-difluorobenzoyl)urea;
1-[4-(2-methyl-4-dimethylaminophenoxy)-3,5-dimethylphenyl]-3-(2-methylbenzoyl)urea;
1-[4-(2-methyl-4-methoxyphenoxy)-3-chloro-6-methylphenyl]-3-(2-methylbenzoyl)urea;
1-[4-(2-methyl-4-methoxyphenoxy)-3,6-dimethyl-5-chlorophenyl]-3-(3,4-dichlorobenzoyl)urea;
1-[4-(2,3-dimethyl-4-bromophenoxy)-3,6-dimenthyl-5-chlorophenyl]-3-(2-chlorobenzoyl)urea;
1-[4-(2,5-dimethyl-4-chlorophenoxy)-3,6-dimethyl-5-chlorophenyl]-3-(2,6-difluorobenzoyl)urea:
1-[4-(2,5-dimethylphenoxy)-3,6-dimethyl-5-chloro-phenyl]-3-(2,6-difluorobenzoyl)urea;
1-[4-(2,5-dimethylphenoxy)-3,6-dimethyl-5-chloro-phenyl]-3-(2-chlorobenzoyl)urea:
1-[4-(2,5-dimethyl-4-ethoxycarbonylphenoxy)-3,6-dimethyl-5-chlorophenyl]-3-(2,6-difluorobenzoyl)urea;
1-[4-(2,5-dimethyl-4-ethoxycarbonylphenoxy)-3,6-dimethyl-5-chlorophenyl]-3-(2-chlorobenzoyl)urea:
1-[4-(2-methyl-4-trifluromethylphenoxy)-3,6-dimethyl-5-chlorophenyl]-3-(2-chlorobenzoyl)urea:
1-[4-(2,5-dimethyl-4-trifluoromethylphenoxy)-3,6-dimethyl-5-chlorophenyl]-3-(2,6-difluorobenzoyl)urea:
1-[4-(2,5-dimethyl-4-trifluromethylphenoxy-3,6-dimethyl-5-chlorophenyl]-3-(2-chlorobenzoyl)urea;
1-[4–2,5-dimethyl-4-trifluoromethoxyphenoxy)-3,6-dimethyl-5-chlorophenyl]-3-(2,6-difluorobenzoyl)urea;
1-[4-(2,5-dimethyl-4-trifluoromethoxyphenoxy)-3,6-dimethyl-5-chlorophenyl]-3-(2-chlorobenzoyl)urea;
1-[4-(2,5-dimethyl-4-methoxyphenoxy)-3,6-dimethyl-5-chlorophenyl)-3-(2,6-difluorobenzoyl)urea:
1-[4-(2,5-dimethyl-4-methoxyphenoxy)-3,6-dimethyl-5-chlorophenyl]-3-(2-chlorobenzoyl)urea;
1-[4-(3,S-dimethyl-4-chlorophenoxy)-3,6-dimethyl-5-chlorophenyl]-3-(2,6-difluorobenzoyl)urea;
1-[4-(2,4,5-trimethylphenoxy)-3,6-dimethyl-5-chlorophenyl)-3-(2,6-difluorobenzoyl)urea;
1-[4-(2,4,5-trimethylphenoxy)-3,6-dimethy-1,5-chlorophenyl)-3-(2-chlorobenzoyl)urea;
1-[4-(2,5-dimethyl-4-bromophenxoy)-3,6-dimethyl-5-chlorophenyl]-3-(2,6-difluorobenzoyl)urea;
1-[4-(2,5-dimethyl-4-cyanophenoxy)-3,6-dimethyl-5-chlorophenyl]-3-(2,6-difluorobenzoyl)urea:
1-[4-(2,5-dimethyl-4-cyanophenoxy)-3,6-dimethyl-5-chlorophenyl]-3-(2-chlorobenzoyl)urea;
1-[4-(2-methyl-4-cyanophenoxy)-3,6-dimethyl-5-chlorophenyl]-3-(2,6-difluorobenzoyl)urea:
1-[4-(2-methyl-4-cyanophenoxy)-3,6-dimethyl-5-chloro-phenyl]-3-(2-chlorobenzoyl)urea;
1-[4-(2,4-dimethylphenoxy)-2,6-dimethyl-5-chlorophenyl]-3-(2,6-difluorobenzoyl)urea:
1-[4-(2,4-dimethylphenoxy)-2,6-dimethyl-5-chlorophenyl]-3-(2-chlorobenzoyl)urea;
1-[4-(2,4-dimethylphenoxy)-2a5-dimethyl-3-chlorophenyl]-3-(2,6-difluorobenzoyl)urea:
1-[4-(2,4-dimethylphenoxy)-2,5-dimethyl-3-chlorophenyl]-3-(2-fluorobenzoyl)urea;
1-[4-(2,4-dimethylphenoxy)-2,5-dimethyl-3-chlorophenyl]-3-(2-chlorobenzoyl)urea;
1-[4-(2,4-dimethylphenoxy)-2,5-dimethyl-3-chlorophenyl]-3-(2,6-dichlorobenzoyl)urea;
1-[4-(2,5-dichloro-4-methylphenoxy)-3,6-dimethyl-5-chlorophenyl]-3-(2,6-difluorobenzoyl)urea;
1-[4-(2,5-dichloro-4-methylphenoxy)-3,6-dimethyl-5-chlorophenyl]-3-(2-chlorobenzoyl)urea;
1-[4-(2-methyl-4,5-dichlorophenoxy)-3,6-dimethyl-5-chlorophenyl]-3-(2,6-difluorobenzoyl)urea;
1-[4-(2-methyl-4,5-dichlorophenoxy)-3,6-dimethyl-5-chlorophenyl]-3-(2-chlorobenzoyl)urea; and
1-[4-(2,5-dimethyl-4-chlorophenoxy)-3-methylphenyl]-3-(2,6-difluorobenzoyl)urea.

U.S. patent application Ser. No. (D-13541-2), filed Mar. 29, 1985, incorporated herein by reference which is application Ser. No. 717,785, now abandoned, discloses and claims 1-(phenoxyphenyl)-3- benzoyl urea compounds which may be used in the method of this invention. Such 1-(phenoxyphenyl)-3- benzoyl urea compounds can be prepared by the methods described in the application, and are available from Union Carbide Agricultural Products Company, Inc., Research Triangle Park, N.C. Illustrative of the 1-(phenoxyphenyl)-3-benzoyl urea compounds of U.S. patent application Ser. No. (D-13541-2) which may be useful in the method of this invention include the following:

1-[4-(2,4-dichlorophenoxy)-2,5-dimethyl-3-chlorophenyl]-3-(2,6-difluorobenzoyl)urea;

1-[4-(2,4-dichlorophenoxy)-2,5-dimethyl-3-chlorophenyl]-3-(2-chlorobenzoyl)urea;

1-[4-(2,4-dichlorophenoxy)-2,5-dimethyl-3-chlorophenyl]-3-(2,6-dichlorobenzoyl)urea;

1-[4-(2,4-dichlorophenoxy)-2,5-dimethyl-3-chlorophenyl]-3-(2-bromo-6-chlorobenzoyl)urea;

1-[4-(2,4-dichlorophenoxy)-2,5-dimethyl-3-chlorophenyl]-3-(2-fluoro-6-bromobenzoyl)urea;

1-[4-(2,4-dichlorophenoxy)-2,5-dimethyl-3-chlorophenyl]-3-(2-fluorobenzoyl)thiourea;

1-[4-(2,4-dichlorophenoxy)-2,5-dimethyl-3-chlorophenyl]-3-(2-bromobenzoyl)thiourea;

1-[4-(2,4-dichlorophenoxy)-2,5-dimethyl-3-chlorophenyl]-3-(2-bromobenzoyl)urea;

1-[4-(2-bromo-4-chlorophenoxy)-2,5-dimethyl-3-chlorophenyl]-3-(2,6-difluorobenzoyl)thiourea;

1-[4-(2-bromo-4-chlorophenoxy)-2,5-dimethyl-3-chlorophenyl]-3-(2,6-difluorobenzoyl)urea;

1-[4-(2-bromo-4-chlorophenoxy)-2,5-dimethyl-3-chlorophenyl]-3-(2,6-dichlorobenzoyl)urea;

1-(4-(2-bromo-4-chlorophenoxy)-2,5-dimethyl-3-chlorophenyl]-3-(2-chlorobenzoyl)urea;

1-[4-(2-bromo-4-chlorophenoxy)-2,5-dimethyl-3-chlorophenyl]-3-(2-fluorobenzoyl)urea;

1-[4-(2-bromo-4-chlorophenoxy)-2,5-dimethyl-3-chlorophenyl]-3-(2-chloro-6-fluorobenzoyl)urea;

1-[4-(2,4-dibromophenoxy)-2,5-dimethyl-3-chlorophenyl]-3-(2-chlorobenzoyl)urea;

1-[4-(2,4-dibromophenoxy)-2,5-dimethyl-3-chlorophenyl]-3-(2-fluorobenzoyl)thiourea;

1-[4-(2,4-dibromophenoxy)-2,5-dimethyl-3-chlorophenyl]-3-(2,6-dichlorobenzoyl)thiourea;

1-[4-(2,4-dibromophenoxy)2,5-dimethyl-3-chlorophenyl]-3-(2-fluorobenzoyl)urea;

1-[4-(2,4-dibromophenoxy)-2,5-dimethyl-3-chlorophenyl]-3-(2,6-dichlorobenzoyl)urea;

1-[4-(2,4-dibromophenoxy)-2,5-dimethyl-3-chlorophenyl]-3-(2-chloro-6-fluorobenzoyl)urea;

1-[4-(2,4-dibromophenoxy)-2,5-dimethyl-3-chlorophenyl]-3-(2-chloro-6-bromobenzoyl)urea;

1-[4-(2-fluoro-4-chlorophenoxy)-2,5-dimethyl-3-chlorophenyl]-3-(2,6-difluorobenzoyl)urea;

1-[4-(2,4-difluorophenoxy)-2,5-dimethyl-3-chlorophenyl]-3-(2-fluorobenzoyl)urea;

1-[4-(2,4-difluorophenoxy-2,5-dimethyl-3-chlorophenyl]-3-(2-chlorobenzoyl)urea;

1-[4-(2,4-difluorophenoxy)-2,5-dimethyl-3-chlorophenyl]-3-(2,6-difluorobenzoyl)urea;

1-[4-(2-chloro-4-fluorophenoxy)-2,5-dimethyl-3-chlorophenyl]-3-(2-chlorobenzoyl)thiourea;

1-[4-(2-chloro-4-fluorophenoxy)-2,5-dimethyl-3-chlorophenyl]-3-(2-chlorobenzoyl)urea;

1-[4-(2-chloro-4-fluorophenoxy)-2,5-dimethyl-3-chlorophenyl]-3-(2,6-difluorobenzoyl)urea;

1-[4-(2-fluoro-4-bromophenoxy)-2,5-dimethyl-3-chlorophenyl]-3-(2-chlorobenzoyl)urea;

1-[4-(2-fluoro-4-bromophenoxy)-2,5-dimethyl-3-chlorophenyl]-3-(2,6-difluorobenzoyl)thiourea:

1-[4-(2-fluoro-4-bromophenoxy)-2,5-dimethyl-3-chlorophenyl]-3-(2,6-difluorobenzoyl)urea;

1-[4-(2-bromo-4-fluorophenoxy)-2,5-dimethyl-3-chlorophenyl]-3-(2,6-difluorobenzoyl)urea;

1-[4-(2-bromo-4-fluorophenoxy)-2,5-dimethyl-3-chlorophenyl]-3-(2,6-difluorobenzoyl)urea;

1-[4-(2,5-dichlorophenoxy)-2,5-dimethyl-3-chlorophenyl]-3-(2,6-difluorobenzoyl)urea;

1-[4-(2,5-dichlorophenoxy)-2,5-dimethyl-3-chlorophenyl]-3-(2-chlorobenzoyl)urea;

1-[4-(2,5-dichlorophenoxy)-2,5-dimethyl-3-chlorophenyl]-3-(2-fluorobenzoyl)thiourea;

1-[4-(2,5-dichlorophenoxy)-2,5-dimethyl-3-chlorophenyl]-3-(2-fluorobenzoyl)urea;

1-[4-(2,4,5-trichlorophenoxy)-2,5-dimethyl-3-chlorophenyl]-3-(2-fluorobenzoyl)urea;

1-[4-(2,4,5-trichlorophenoxy)-2,5-dimethyl-3-chlorophenyl]-3-(2,6-difluorobenzoyl)urea;

1-[4-(2,4,5-trichlorophenoxy)-2,5-dimethyl,3-chlorophenyl]-3-(2-chlorobenzoyl)thiourea;

1-[4-(2,4,5-trichlorophenoxy)-2,5-dimethyl-3-chlorophenyl]-3-(2,6-difluorobenzoyl)urea;

1-[4-(2,5-dichloro-4-bromophenoxy)-2,5-dimethylphenyl]-3-(2-chlorobenzoyl)urea;

1-[4-(2,5-dichloro-4-bromophenoxy)-2,5-dimethyl-3-chlorophenyl]-3-(2-fluorobenzoyl)urea;

1-[4-(2,5-dichloro-4-bromophenoxy)-2,5-dimethyl-3-chlorophenyl]-3-(2,6-difluorobenzoyl)thiourea;

1-[4-(2,5-dichloro-4—4-bromophenoxy)-2,5-dimethyl-3-chlorophenyl]-3-(2,6-difluorobenzoyl)thiourea;

1-[4-(2-bromo-4,5-dichlorophenoxy)-2,5-dimethyl-7-chlorophenyl]-3-(2,6-difluorobenzoyl)urea;

1-[4-(2-bromo-4,5-dichlorophenoxy)-2,5-dimethyl-3-chlorophenyl]-3-(2-chlorobenzoyl)urea;

1-[4-(2-bromo-4,5-dichlorophenoxy)-2,5-dimethyl-3-chlorophenyl]-3-(2-chloro-6-fluorobenzoyl)urea;

1-[4-(2-bromo-4,5-dichlorophenoxy)-2,5-dimethyl-3-chlorophenyl]-3-(2-fluorobenzoyl)thiourea;

1-[4-(2-bromo-4,5-dichlorophenoxy)-2,5-dimethyl-3-chlorophenyl]-3-(2-fluorobenzoyl)urea;

1-[4-(2,5-dibrom-4-chlorophenoxy)-2,5-dimethyl-3-chlorophenyl]-3-(2,6-difluorobenzoyl)ure,a;

1-[4-(2,5-dibromo-4-chlorophenoxy)-2,5-dimethyl-3-chlorophenyl]-3-(2-chlorobenzoyl)urea;

1-[4-(2,5-dibromo-4-chlorophenoxy)-2,5-dimethyl-3-chlorophenyl]-3-(2-difluorobenzoyl)urea;

1-[4-(2,5-dichloro-4-fluorophenoxy)-2,5-dimethyl-3-chlorophenyl]-3-(2,6-difluorobenzoyl)urea;

1-[4-(2,4-dichlorophenoxy)-2,3,5-trichlorophenyl]-3-(2-chlorobenzoyl)urea;

1-[4-(2,4-dichlorophenoxy)-2,3,5-trichlorophenyl]-3-(2,6-difluorobenzoyl)urea;

1-[4-(2,4-dichlorophenoxy)-2,3,5-trichloro-phenyl]-3-(2-fluorobenzoyl)urea;

1-[4-(2,4-dichlorophenoxy)-2,3,5-trichlorophenyll-3-(2,6-dichlorobenzoyl)urea;

1-[4-(2-bromo-4-chlorophenoxy)-2,3,5-trichlorophenyl]-3-(2,6-difluorobenzoyl)urea;

1-[4-(2-bromo-4-chlorophenoxy)-2,3,5-trichlorophenyl]-3-(2-chlorobenzoyl)urea;

1-[4-(2-bromo-4-chlorophenoxy)-2,3,5-trichlorophenyl]-3-(2-chloro-6-fluorobenzoyl)urea;

1-[4-(2-bromo-4-chlorophenoxy)-2,3,5-trichlorophenyl]-3-(2-fluorobenzoyl)urea;

1-[4-(2-bromo-4-chlorophenoxy)-2,3,5-trichlorophenyl]-3-(2,6-dichlorobenzoyl)urea;

1-[4-(2,4-dibromophenoxy)-2,3,5-trichlorophenyl]-3-(2,6-difluorobenzoyl)urea;
1-[4-(2,4-dibromophenoxy)-2,3,5-trichlorophenyl]-3-(2-chlorobenzoyl)urea;
1-[4-(2,4-dibromophenoxy)-2,3,5-trichlorophenyl]-3-(2-fluorobenzoyl)urea;
1[4-(2,5-dichlorophenoxy)-2,3,5-trichloro-pheryl]-3-(2-fluorobenzoyl)urea;
1-[4-(2,5-dichlorophenoxy)-2,3,5-trichlorophenyll-3-(2,6-difluorobenzoyl)urea;
1-[4-(2,5-dichlorophenoxy)-2,3,5-trichlorophenyl]-3-(2,6-difluorobenzoyl)urea;
1-[4-(2,5-dichlorophenoxy)-2,3,5-trichlorophenyl]-3-(2-chloro-6-fluorobenzoyl)urea;
1-[4-(2-bromo-5-chlorophenoxy)-2,3,5-trichlorophenyl]-3-(2,6-difluorobenzoyl)urea;
1-[4-(2-bromo-5-chlorophenoxy-2,3,5-trichlorophenyl]-3-(2-fluorobenzoyl)urea;
1-[4-(2-bromo-5-chlorophenoxy)-2,3,5-trichlorophenyl]-3-(2-chlorobenzoyl)urea;
1-[4-(2,4,5-trichlorophenoxy)-2,3,5-trichlorophenyl]-3-(2,6-difluorobenzoyl)urea;
1-[4-(2,4,5-trichlorophenoxy)-2,3,5-trichlorophenyl)-3-(2-chlorobenzoyl)urea;
1-(4-(2,4,5-trichlorophenoxy)-2,3,5-trichlorophenyl]-3-(2-fluorobenzoyl)urea;
1-[4-(2,4-dichlorophenoxy)-3,5-dimethyl-2-chlorophenyl]-3-(2,6-diflurobenzoyl)urea;
1-[4-(2,4-dichlorophenoxy)-3,5-dimethyl-2-chlorophenyl)-3-(2-flurobenzoyl)urea;
1-[4-(2,4-dichlorophenoxy)-3,5-dimethyl-2-chlorophenyl)-3-(2-chlorobenzoyl)urea;
1-[4-(2,4-dichlorophenxoy)-3,5-dimethyl-2-chlorophenyl]-3-(2,6-dichlorobenzoyl)urea;
1-[4-(2-bromo-4-chlorophenoxy)-3,5-dimethyl-2-chlorophenyl]-3-(2,6-diflurobenzoyl)urea;
1-[4-(2,4-dibromophenoxy)-3,5-dimethyl-2-chlorophenyl]-3-(2-chlorobenzoyl)urea;
1-[4-(2,4-dibromophenoxy)-3,5-dimethyl-2-chlorophenyl]-3-(2,6-diflurobenzoyl)urea;
1-[4-(2,4-dichlorophenoxy)-2,3*5-trimethylphenyl]-3-(2-chlorobenzoyl)urea;
1-[4-(2,4-dichlorophenoxy)-2,3,5-trimethylphenyl]-3-(2,6-difluorobenzoyl)urea;
1-[4-(2,4-dichlorophenoxy)-2,3*5-trimethylphenyl]-3-(2-fluorobenzoyl)urea;
1-[4-(2,4-dichlorophenoxy)-2,3,5-trimethylphenyl]-3-(2,6-dichlorobenzoyl)urea;
1-[4-(2-bromo-4-chlorophenoxy)-2,3,5-trimethylphenyl]-3-(2-chlorobenzoyl)urea;
1-[4-(2-bromo-4-chlorophenoxy)-2,3,5-trimethylphenyl]-3-(2,6-difluorobenzoyl)urea;
1-[4-(2-bromo-4-chlorophenoxy)-2,3,5-trimethylphenyl]-3-(2-fluorobenzoyl)urea; and
1-[4-(2,4-dibromophenoxy)-2,3,5-trimethylphenyl]-3-(2,6-difluorobenzoyl)urea, U.S. patent application Ser. No. (D-13541-3), filed Mar. 29, 1985, incorporated herein by reference, discloses and claims 1-(phenoxyphenyl)-3- benzoyl urea compounds which may be used in the method of this invention. Such 1-(phenoxyphenyl)-3- benzoyl urea compounds can be prepared by the methods described in the application, and are available from Union Carbide Agricultural Products Company, Inc., Research Triangle Park, N.C. Illustrative of the 1-(phenoxyphenyl)-3-benzoyl urea compounds of U.S. patent application Ser. No. (D-13541-3) which may be useful in the method of this invention include the following:

1-[4-(2,4-dichlorophenoxy)-2,6-dimethyl-3-chlorophenyl]-3-(2,6-difluorobenzoyl)urea;
1-[4-(2,4-dichlorophenoxy)-2,6-dimethyl-3-chlorophenyl]-3-(2-chlorobenzoyl)urea;
1-[4-(2,4-dichlorophenoxy)-2,6-dimethyl-3-chlorophenyl]-3-(2,6-dichlorobenzoyl)urea;
1-[4-(2,4-dichlorophenoxy)-2,6-dimethyl-3-chlorophenyl]-3-(2-bromo-6-chlorobenzoyl)urea;
1-[4-(2,4-dichlorophenoxy)-2,6-dimethyl-3-chlorophenyl]-3-(2-fluoro-6-bromobenzoyl)urea;
1-[4-(2,4-dichlorophenoxy)-2,6-dimethyl-3-chlorophenyl]-3-(2-fluorobenzoyl)thiourea;
1-(4-(2,4-dichlorophenoxy)-2,6-dimethyl-3-chlorophenyl]-3-(2-bromobenzoyl)thiourea;
1-[4-(2,4-dichlorophenoxy)-2,6-dimethyl-3-chlorophenyl]-3-(2-bromobenzoyl)urea;
1-[4-(2-bromo-4-chlorophenoxy)-2,6-dimethyl-3-chlorophenyl]-3-(2,6-difluorobenzoyl)thiourea;
1-[4-(2-bromo-4-chlorophenoxy)-2,6-dimethyl-3-chlorophenyl]-3-(2,6-difluorobenzoyl)urea;
1-[4-(2-bromo-4-chlorophenoxy)-2,6-dimethyl-3-chlorophenyl]-3-(2,6-dichlorobenzoyl)urea;
1-[4-(2-bromo-4-chlorophenoxy)-2,6-dimethyl-3-chlorophenyl]-3-(2-chlorobenzoyl)urea;
1-[4-(2-bromo-4-chlorophenoxy)-2,6-dimethyl-3-chlorophenyl]-3-(2-fluorobenzoyl)urea;
1-[4-(2-bromo-4-chlorophenoxy)-2,6-dimethyl-3-chlorophenyl]-3-(2-chloro-6-fluorobenzoyl)urea;
1-[4-(2,4-dibromophenoxy)-2,6-dimethyl-3-chlorophenyl]-3-(2-chlorobenzoyl)urea;
1-[4-(2,4-dibromophenoxy)-2,6-dimethyl-3-chlorophenyl]-3-(2-fluorobenzoyl)thiourea;
1-[4-(2,4-dibromophenoxy)-2,6-dimethyl-3-chlorophenyl]-3-(2,6-dichlorobenzoyl)thiourea;
1-[4-(2,4-dibromophenoxy)2,6-dimethyl-3-chlorophenyl]-3-(2-fluorobenzoyl)urea;
1-[4-(2,4-dibromophenoxy)-2,6-dimethyl-3-chlorophenyl]-3-(2,6-dichlorobenzoyl)urea,
1-[4-(2,4-dibromophenoxy)-2,6-dimethyl-3-chlorophenyl]-3-(2-chloro-6-fluorobenzoyl)urea;
1-[4-(2,4-dibromophenoxy)-2,6-dimethyl-3-chlorophenyl]-3-(2-chloro-6-bromobenzoyl)urea;
1-[4-(Z-fluoro-4-chlorophenoxy)-2,6-dimethyl-3-chlorophenyl]-3-(2,6-difluorobenzoyl)urea;
1-[4-(2,4-difluorophenoxy)-2,6-dimethyl-3-chlorophenyl]-3-(2-fluorobenzoyl)urea;
1-[4-(2,4-difluorophenoxy-2,6-dimethyl-3-chlorophenyl]-3-(2-chlorobenzoyl)urea;
1-[4-(2,4-difluorophenoxy)-2,6-dimethyl-3-chlorophenyl]-3-(2,6'-difluorobenzoyl)urea;
1-[4-(2-chloro-4-fluorophenoxy)-2,6-dimethyl-3-chlorophenyl]-3-(2-chlorobenzoyl)thiourea;
1-[4-(2-chloro-4-fluorophenoxy)2,6-dimethyl-3-chlorophenyl]-3-(2-chlorobenzoyl)urea;
1-[4-(2-chloro-4'-fluorophenoxy)-2,6-dimethyl-3-chlorophenyl]-3-(2,6-difluorobenzoyl)urea;
1-[4-(2-fluoro-4-bromophenoxy)-2,6-dimethyl-3-chlorophenyl]-3-(2-chlorobenzoyl)urea;
1-[4-(2-fluoro-4-bromophenoxy)-2,6-dimethyl-3-chlorophenyl]-3-(2,6-difluorobenzoyl)thiourea;
1-(4-(2-fluoro-4-bromophenoxy)-2,6-dimethyl-3-chlorophenyl]-3-(2,6-difluorobenzoyl)urea;
1-[4-(2-bromo-4-fluorophenoxy)-2,6-dimethyl-3-chlorophenyl]-3-(2,6-difluorobenzoyl)urea;
1-[4-(2-bromo-4-fluorophenoxy)-2,6-dimethyl-3-chlorophenyl]-3-(2,6-difluorobenzoyl)urea;
1-[4-(2,5-dichlorophenoxy)-2,6-dimethyl-3-chlorophenyl]-3-(2,6-difluorobenzoyl)urea;

1-[4-(2,5-dichlorophenoxy)-2,6-dimethyl-3-chlorophenyl]-3-(2-chlorobenzoyl)urea;
1-[4-(2,5-dichlorophenoxy)-2,6-dimethyl-3-chlorophenyl]-3-(2-fluorobenzoyl)thiourea;
1-[4-(2,5-dichlorophenoxy)-2,6-dimethyl-3-chlorophenyl]-3-(2-fluorobenzoyl)urea;
1-[4-(2,4,5-trichlorophenoxy)-2,6-dimethyl-3-chlorophenyl]-3-(2-fluorobenzoyl)urea;
1-[4-(2,4,5-trichlorophenoxy)-2,6-dimethyl-3-chlorophenyl]-3-(2,6-difluorobenzoyl)urea:
1-[4-(2,4,5-trichlorophenoxy)-2,6-dimethyl-3-chlorophenyl]-3-(2,-chlorobenzoyl)thiourea:
1-[4-(2,4,5-trichlorophenoxy)-2,6-dimethyl-3-chlorophenyl]-3-(2,6-difluorobenzoyl)urea;
1-[4-(2,5-dichloro-4-bromophenoxy)-2,6-dimethylphenyl]-3-(2-chlorobenzoyl)urea;
1-[4-(2,5-dichloro-4-bromophenoxy)-2,6-dimethyl-3-chlorophenyl]-3-(2-fluorobenzoyl)urea;
1-[4-(2,5-dichloro-4-bromophenoxy)-2,6-dimethyl-3-chlorophenyl]-3-(2,6-difluorobenzoyl)thiourea;
1-[4-(2,5-dichloro-4—bromophenoxy)-2,6-dimethyl-3-chlorophenyl]-3-(2,6-difluorobenzoyl)thiourea;
1-[4-(2-bromo-4,5-dichlorophenoxy)-2,6-dimethyl-7-chlorophenyl]-3-(2,6-difluorobenzoyl)urea;
1-[4-(2-bromo-4,5-dichlorophenoxy)-2,6-dimethyl-3-chlorophenyl]-3-(2-chlorobenzoyl)urea;
1-[4-(2-bromo-4,5-dichlorophenoxy)-2,6-dimethyl-3-chlorophenyl]-3-(2-chloro-6-fluorobenzoyl)urea:
1-[4-(2-bromo-4,5-dichlorophenoxy)-2,6-dimethyl-3-chlorophenyl)-3-(2-fluorobenzoyl)thiourea;
1-[4-(2-bromo-4,,5-dichlorophenoxy)-2,6-dimethyl-3-chlorophenyl]-3-(2-fluorobenzoyl)urea;
1-[4-(2,5-dibrom-4-chlorophenoxy)-2,6-dimethyl-3-chlorophenyl]-3-(2,6-difluorobenzoyl)urea;
1-[4-(2,5-dibromo-4-chlorophenoxy)-2,6-dimethyl-3-chlorophenyl]-3-(2-chlorobenzoyl)urea:
1-[4-(2,5-dibromo-4-chlorophenoxy)-2,6-dimethyl-3-chlorophenyl]-3-(2-difluorobenzoyl)urea;
1-[4-(2,S-dichloro-4-fluorophenoxy)-2,6-dimethyl-3-chlorophenyl]-3-(2,6-difluorobenzoyl)urea:
1-[4-(2,4-dichlorophenoxy)-2,3,6-trichlorophenyl]-3-(2-chlorobenzoyl)urea;
1-[4-(2,4-dichlorophenoxy)-2,3,6-trichlorophenyl]-3-(2,6-difluorobenzoyl)urea;
1-[4-(2,4-dichlorophenoxy) -2,3,6-trichloro-phenyl]-3-(2-fluorobenzoyl)urea;
1-[4-(2,4-dichlorophenoxy)-2,3,6-trichlorophenyl]-3-(2,6-dichlorobenzoyl)urea;
1-[4-(2-bromo-4-chlorophenoxy)-2,3,6-trichlorophenyl]-3-(2,6-difluorobenzoyl)urea;
1-[4-(2-bromo-4-chlorophenoxy)-2,3,6-trichlorophenyl]-3-(2-chlorobenzoyl)urea;
1-[4-(2-bromo-4-chlorophenoxy)-2,3,6-trichlorophenyl]-3-(2-chloro-6-fluorobenzoyl)urea;
1-[4-(2-bromo-4-chlorophenoxy)-2,3,6-trichlorophenyl]-3-(2-fluorobenzoyl)urea;
1-[4-(2-bromo-4-chlorophenoxy)-2,3,6-trichlorophenyl]-3-(2,6-dichlorobenzoyl)urea;
1-[4-(2,4-dibromophenoxy)-2,3,6-trichlorophenyl]-3-(2,6-difluorobenzoyl)urea;
1-[4-(2,4-dibromophenoxy)-2,3,6-trichlorophenyl]-3-(2-chlorobenzoyl)urea:
1-[4-(2,4-dibromophenoxy)-2,3,6-trichlorophenyl]-3-(2-fluorobenzoyl)urea;
1-[4-(2,5-dichlorophenoxy)-2,3,6-trichloro-phenyl]-3-(2-fluorobenzoyl)urea;
1-[4-(2,5-dichlorophenoxy)-2,3,6-trichlorophenyl]-3-(2,6-difluorobenzoyl)urea;

1-[4-(2,5-dichlorophenoxy)-2,3,6-trichlorophenyl]-3-(2,6-difluorobenzoyl)urea;
1-[4-(2,5-dichlorophenoxy)-2,3,6-trichlorophenyll-3-(2-chloro-6-fluorobenzoyl)urea;
1-[4-(2-bromo-5-chlorophenoxy)-2,3,6-trichlorophenyl]-3-(2,6-difluorobenzoyl)urea;
1-[4-(2-bromo-5-chlorophenoxy-2,3,6-trichlorophenyl]-3-(2-fluorobenzoyl)urea;
1-[4-(2-bromo-5-chlorophenoxy)-2,3,6-trichlorophenyl]-3-(2-chlorobenzoyl)urea;
1-[4-(2,4,5-trichlorophenoxy)-2,3,6-trichlorophenyl]-3-(2,6-difluorobenzoyl)urea;
1-[4-(2,4,5-trichlorophenoxy)-2,3,6-trichlorophenyl)-3-(2-chlorobenzoyl)urea:
1-[4-(2,4,5-trichlorophenoxy)-2,3,6-trichlorophenyl]-3-(2-fluorobenzoyl)urea:
1-[4-(2,4-dichlorophenoxy)-3,6-dimethyl-2-chlorophenyl]-3-(2,6-diflurobenzoyl)urea;
1-[4-(2,4-dichlorophenoxy)-3,6-dimethyl-2-chlorophenyl)-3-(2-flurobenzoyl)urea;
1-[4-(2,4-dichlorophenoxy)-3,6-dimethyl-2-chlorophenyl)-3-(2-chlorobenzoyl)urea;
1-[4-(2,4-dichlorophenxoy)-3,6-dimethyl-2-chlorophenyl]-3-(2,6-dichlorobenzoyl)urea:
1-[4-(2-bromo-4-chlorophenoxy)-3,6-dimethyl-2-chlorophenyl]-3-(2,6-diflurobenzoyl)urea:
1-[4-(2,4-dibromophenoxy)-3,6-dimethyl-2-chlorophenyl]-3-(2-chlorobenzoyl)urea;
1I-[4-(2,4-dibromophenoxy)-3,6-dimethyl-2-chlorophenyl]-3-(2,6-diflurobenzoyl)urea;
1-[4-(2,4-dichlorophenoxy)-2,3,6-trimethylphenyl]-3-(2-chlorobenzoyl)urea:
1-[4-(2,4-dichlorophenoxy)-2,3,6-trimethylphenyl]-3-(2,6-difluorobenzoyl)urea;
1-[4-(2,4-dichlorophenoxy)-2,3,6-trimethylphenyl]-3-(2-fluorobenzoyl)urea;
1-[4-(2,4-dichlorophenoxy)-2,3,6-trimethylphenyl]-3-(2,6-dichlorobenzoyl)urea;,
1-[4-(2-bromo-4-chlorophenoxy)-2,3,6-trimethylphenyl]-3-(2-chlorobenzoyl)urea;
1-[4-(2-bromo-4-chlorophenoxy)-2,3,6-trimethylphenyl]-3-(2,6-difluorobenzoyl)urea;
1-[4-(2-bromo-4-chlorophenoxy)-2,3,6-trimethylphenyl]-3-(2-fluorobenzoyl)urea; and
1-[4-(2,4-dibromophenoxy)-2,3,6-trimethylphenyl]-3-(2,6-difluorobenzoyl)urea, U.S. patent application Ser. No. 712,195, filed Mar. 15, 1985, incorporated herein by reference, discloses and claims alpha-cyanobenzyl phenyl benzoyl urea compounds which may be used in the method of this invention. Such alpha-cyanobenzyl phenyl benzoyl urea compounds can be prepared by the methods described in the application, and are available from Union Carbide Agricultural Products Company, Inc., Research Triangle Park, N.C. Illustrative of the alpha-cyanobenzyl phenyl benzoyl urea compounds of U.S. patent application Ser. No. (D-14858) which may be useful in the method of this invention include the following:
1-(2,5-dichloro-4-(alpha-cyano-4-fluorobenzyl)phenyl]-3-(2,6-difluorobenzoyl)urea;
1-[2-methyl-5-chloro-4-(alpha-cyano-4-chlorobenzyl)phenyl]-3-(2,6-difluorobenzoyl)urea;
1-[2,5-dichloro-4-(alpha-cyano-4-chlorobenzyl)phenyl]-3-(2,6-difluorobenzoyl)urea:
1-[4-(alpha-cyano-4-methylbenzyl)phenyl]-3-(2,6-difluorobenzoyl)urea;
1-[2,5-dichloro-4-(alpha-cyano-2,4-dimethylbenzyl)phenyl]-3-(2,6-difluorobenzoyl)urea;

1-[2,5-dichloro-4-(alpha-cyano-4-fluorobenzyl)phenyl]-3-(2-fluorobenzoyl)urea;

1-[2-methyl-5-chloro-4-(alpha-cyano-alpha-methyl-4-chlorobenzyl)phenyl-3-(2,6-difluorobenzoyl)urea;

1-[2,5-dichloro-4-(alpha-cyano-4-methylbenzyl)phenyl-3-(2,6-difluorobenzoyl)thiourea;

1-[3-chloro-2,5-dimethyl-4-(alpha-cyano-4-chlorobenzyl)phenyl]-3-(2,6-difluorobenzoyl)urea:

1-[2,3,5-trichloro-4-(alpha-cyano-4-methylbenzyl)phenyl]-3-(2,6-difluorobenzoyl)urea;

1-[2,5-dichloro-4-(alpha-cyano-alpha-propyl-4-chlorobenzyl)phenyl]-3-(2-chlorobenzoyl)urea;

1-[2,5-dichloro-4-(alpha-cyano-4-chlorobenzyl)phenyl]-3-(2,6-dimethoxybenzoyl)urea;

1-[2-methyl-5-chloro-4-(alpha-cyano-4-chlorobenzyl)phenyl]-3-(2-trifluoromethylbenzoyl)urea;

1-[2,5-dichloro-4-(alpha-cyano-4-trifluoromethoxybenzyl)phenyl]-3-(2,6-difluorobenzoyl)urea:

1-[2,5-dichloro-4-(alpha-cyano-2-bromo-4-chlorobenzyl)phenyl]-3-(2,6-difluorobenzoyl)urea;

1-[2-methyl-5-chloro-4-(alpha-cyano-4-bromobenzyl)phenyl]-3-(2,6-difluorobenzoyl)urea;

1-[2,3-dichloro-4-(alpha-cyano-4-chlorobenzyl)phenyl]-3-(2-trifluoromethoxybenzoyl)urea;

1-[2-chloro-5-trifluoromethyl)-4-(alpha-cyano-4-cyanobenzyl)phenyl]-3-(2,6-difluorobenzoyl) urea;

1-[2-chloro-5-ethoxycarbonyl-4-(alpha-cyano-2,4-dichlorobenzyl)phenyl]-3-(2,6-difluorobenzoyl)urea; and 1-[2,5-dichloro-4-(alpha-cyano-2-bromo-4-methoxybenzyl)phenyl]-3-(2,6-difluorobenzoyl)urea.

U.S. patent application Ser. No. 428,994, filed Sep. 30, 1982, incorporated herein by reference, discloses and claims bicyclooxyheterocyclyl aroyl urea compounds which may be used in the method of this invention. Such bicyclooxyheterocyclyl aroyl urea compounds can be prepared by the methods described in the application, and are available from Union Carbide Agricultural Products Company, Inc., Research Triangle Park, N.C. Illustrative of the bicyclooxyheterocyclyl aroyl urea compounds of U.S. patent application Ser. No. 428,994 which may be useful in the method of this invention include the following:

1-(2-[4-chloro-1-naphthoxy)-S-pyridyl)-3-(2,6-difluorobenzoyl)urea:

1-(2-[4-chloro-1-naphthoxy]-5-pyridyl)-3-(2-chloro-6-fluorobenzoyl)urea:

1-(3-chloro-2-[4-chloro-5,6,7,8-tetrahydro-1-naphthoxy]-5-pyridyl)-3-(2,6-difluorobenzoyl)urea:

1-(3-chloro-2-[4-chloro-5,6,7,8-tetrahydro-1-naphthoxy]-5-pyridyl)-3-(2-chloro-6-fluorobenzoyl)urea;

1-(3-chloro-2-[4-chloro-1-naphthoxy]-5-pyridyl)-3-(2,6-difluorobenzoyl)urea:

1-(3-chloro-2-[4-chloro-1-naphthoxy]-5-pyridyl)-3-(2-chloro-6-fluorobenzoyl)urea:

1-(2-[4-chloro-1-naphthoxy]-3-methyl-5-pyridyl)-3-(2,6-difluorobenzoyl)urea:

1-(2-[4-chloro-1-naphthoxy]-3-methyl-5-pyridyl)-3-(2-chloro-6-fluorobenzoyl)urea:

1-(3-chloro-2-[1,6-dibromo-2-naphthoxy]-5-pyridyl)-3-(2,6-difluorobenzoyl)urea:

1-(3-chloro-2-[1,6-dibromo-2-naphthoxy]-5-pyridyl)-3-(2-chloro-6-fluorobenzoyl)urea:

1-(3-chloro-2-[4-methoxy-1-naphthoxy]-S-pyridyl)-3-(2,6-difluorobenzoyl)urea:

1-(3-methoxy-2-[4-methoxy-1-naphthoxy]-5-pyridyl)-3-(2,6-difluorobenzoyl)urea:

1-(3-bromo-2-[4-dimethylamino-5,6,7,8-tetrahydro-1-naphthoxy]-5-pyridyl)-3-(2,6-difluorobenzoyl)urea;

1-(3-bromo-2-[4-dimethylamino-5,6,7,8-tetrahydro-1-naphthoxy]-5-pyridyl)-3-(2-chlorobenzoyl)urea;

1-(3-chloro-2-[4-dimethylamino-5,6,7,8-tetrahydro-1-naphthoxy]-5-pyridyl)-3-(2-chlorobenzoyl)urea;

1-(3-chloro-2-[4-dimethylamino-5,6,7,8-tetrahydro-1-naphthoxy]-5-pyridyl)-3-(2,6-difluorobenzoyl)urea:

1-(2-[4-dimethylamino-5,6,7,8-tetrahydro-1-naphthoxy]-3-methyl-5-pyridyl)-3-(2-chloro-6-fluorobenzoyl) urea: and 1-(2-[4-dimethylamino-5,6,7,8-tetrahydro-1-naphthoxy]-3-methyl-5-pyridyl)-3-(2-chlorobenzoyl)urea.

U.S. patent application Ser. No. 454,847, filed Dec. 30, 1982 abandoned parent application to U.S. Pat. No. 4,659,724, incorporated herein by reference, discloses and claims 1-(pyridyloxyaryl)-3-benzoyl urea compounds which may be used in the method of this invention. Such 1-(pyridyloxyaryl)-3-benzoyl urea compounds can be prepared by the methods described in the application, and are available from Union Carbide Agricultural Products Company, Inc., Research Triangle Park, N.C. Illustrative of the 1-(pyridyloxyaryl)-3-benzoyl urea compounds of U.S. patent application Ser. No. 454,847 abandoned parent application to U.S. Pat. No. 4659,724 which may be useful in the method of this invention include the following:

1-[4-(3-chloro-5-cyano-2-pyridyloxy)-3,5-dibromophenyl]-3-(2,6-difluorobenzoyl)urea:

1-(4-(3-chloro-5-cyano-2-pyridyloxy)-3,5-dibromophenyl]-3-(2-chlorobenzoyl)urea:

1-(4-(3-chloro-5-cyano-2-pyridyloxy)-3,5-dibromophenyl]-3-(2-chloro-6-fluorobenzoyl)urea:

1-[4-(3-cyano-2-pyridyloxy)-3,5-dibromophenyl]-3-(2,6-difluorobenzoyl)urea:

1-[4-(5-cyano-2-pyridyloxy)-3,5-dibromophenyl]-3-(2-chlorobenzoyl)urea:

1-[4-(5-cyano-2-pyridyloxy)-3,5-dibromophenyl]-3-(2-chloro-6-fluorobenzoyl)urea:

1-[4-(5-cyano-2-pyridyloxy)-3,5-dibromophenyl]-3-(2,6-dichlorobenzoyl)urea;

1-[4-(5-cyano-2-pyridyloxy)-3,5-dimethylphenyl]-3-(2,6-difluorobenzoyl)urea;

1-[4-(5-cyano-2-pyridyloxy)-3,5-dimethylphenyl]-3-(2-chlorobenzoyl)urea;

1-[4-(5-cyano-2-pyridyloxy)-3,5-dimethylphenyl]-3-(2,6-dichlorobenzoyl)urea:

1-[4-(5-cyano-2-pyridyloxy)-3,5-dimethylphenyl-3-(2-fluorobenzoyl)urea;

1-[4-(3-chloro-5-cyano-2-pyridyloxy)-3,5-dimethylphenyl]-3-(2-6-difluorobenzoyl)urea:

1-[4-(3-chloro-5-cyano-2-pyridyloxy)-3,5-dimethylphenyl-3-(2-6-dichlorobenzoyl)urea;

1-[4-(3-chloro-5-cyano-2-pyridyloxy)-3,5-dimethylphenyl]-3-(2-chloro-6-fluorobenzoyl)urea;

1-[4-(5-cyano-2-pyridyloxy)-3-trifluoromethylphenyl]-3-(2-chlorobenzoyl)urea;

1-[4-(5-cyano-2-pyridyloxy)-3-trifluoromethylphenyl]-3-(2,6-difluorobenzoyl)urea;

1-[4-(5-cyano-2-pyridyloxy)-3-trifluoromethylphenyl]-3-(2,6-difluorobenzoyl)urea;

1-[4-(5-cyano-2-pyridyloxy)-3-trifluoromethylphenyl]-3-(2,6-dichlorobenzoyl)urea;

1-[4-(3-chloro-5-cyano-2-pyridyloxy)-3-trifluoromethylphenyl]-3-(2-chlorobenzoyl)urea:

1-[4-(3-chloro-5-cyano-2-pyridyloxy)-3-trifluoromethylphenyl]-3-(2,6-difluorobenzoyl)urea;

1-[4-(3-chloro-5-cyano-2-pyridyloxy)-3-trifluoromethylphenyl]-3-(2,6-dichlorobenzoyl)urea;

1-[4-(3-chloro-5-cyano-2-pyridyloxy)-3-trifluoromethylphenyl]-3-(2-chloro-6-fluorobenzoyl)urea;

1-[4-(3-chloro-5-cyano-2-pyridyloxy)-3,6-dimethyl-5-chlorophenyl]-3-(2-chlorobenzoyl)urea;
1-[4-(3-chloro-5-cyano-2-pyridyloxy)-3,6-dimethyl-5-chlorophenyl]-3-(2,6-difluorobenzoyl)urea;
1-[4-(3-chloro-5-cyano-2-pyridyloxy)-3,6-dimethyl-5-chlorophenyl]-3-(2,6-dichlorobenzoyl)urea;
1-[4-(31-chloro-5-cyano-2-pyridyloxy)-3,6-dimethyl-5-chlorophenyl]-3-(2-chloro-6-fluorobenzoyl)urea:
1-[4-(3-methyl-5-nitro-2-pyridyloxy)-3,5-dibromophenyl]-3-(2-chlorobenzoyl)urea;
1-[4-(3-methyl-5-nitro-2-pyridyloxy)-3,5-dibromophenyl]-3-(2,6-difluorobenzoyl)urea;
1-[4-(3-methyl-5-nitro-2-pyridyloxy)-3,5-dibromophenyl]-3-(2,6-dichlorobenzoyl)urea;
1-[4-(3-methyl-5-nitro-2-pyridyloxy)-3,5-dibromophenyl]-3-(2-chloro-6-fluorobenzoyl)urea;
1-[4-(3-methyl-5-nitro-2-pyridyloxy)-3,6-dimethyl-5-chlorophenyl]-3-(2-chlorobenzoyl)urea;
1-[4-(3-methyl-5-nitro-2-pyridyloxy)-3,6–4imethyl-5-chlorophenyl]-3-(2,6-difluorobenzoyl)urea;
1-[4-(3-methyl-5-nitro-2-pyridyloxy)-3,6-dimethyl-5-chlorophenyl]-3-(2,6-dichlorobenzoyl)urea:
1-[4-(3-methyl-5-nitro-2-pyridyloxy)-3,6-dimethyl-5-chlorophenyl]-3-(2-chloro-6-fluorobenzoyl)urea;
1-[4-(5-cyano-2-pyridyloxy)-3,6-dimethyl-5-chlorophenyl]-3-(2-chlorobenzoyl)urea;
1-[4-(5-cyano-2-pyridyloxy)-3,6-dimethyl-5-chlorophenyl]-3-(2-chlorobenzoyl)urea:
1-[4-(5-cyano-2-pyridyloxy)-3,6-dimethyl-5-chlorophenyl]-3-(2,6-dichlorobenzoyl)urea;
1-[4-(5-cyano-2-pyridyloxy)-3,6-dimethyl-5-chlorophenyl]-3-(2,6-difluorobenzoyl)urea;
1-[4-(5-cyano-2-pyridyloxy)-3,6-dimethyl-5-chlorophenyl]-3-(2-chloro-6-fluorobenzoyl)urea;
1-[4-(3-methyl-5-cyano-2-pyridyloxy)-3-methylphenyl]-3-(2-chlorobenzoyl)urea;
1-[4-(3-methyl-5-cyano-2-pyridyloxy)-3-methylphenyl]-3-(2,6-difluorobenzoyl)urea:
1-[4-(3-methyl-5-cyano-2-pyridyloxy)-3-methylphenyl]-3-(2,6-dichlorobenzoyl)urea;
1-[4-(3-methyl-5-cyano-2-pyridyloxy)-3-methylphenyl]-3-(2-chloro-6-fluorobenzoyl)urea;
1-[4-(3-chloro-5-cyano-2-pyridyloxy)-3-methylphenyl]-3-(2-chlorobenzoyl)urea:
1-[4-(3-chloro-5-cyano-2-pyridyloxy)-3-methylphenyl3-3-(2,6-difluorobenzoyl)urea;
1-[4-(3-chloro-5-cyano-2-pyridyloxy)-3-methylphenyl]-3-(2,6-dichlorobenzoyl)urea;
1-[4-(3-chloro-5-cyano-2-pyridyloxy)-3-methylphenyl]-3-(2-chloro-6-fluorobenzoyl)urea;
1-[4-(3-chloro-5-cyano-2-pyridyloxy)-3-methylphenyl]-3-(2-methylbenzoyl)urea;
1-[4-(3-chloro-5-cyano-2-pyridyloxy)-3-methylphenyl]-3-(2-trifluoromethylbenzoyl)urea;
1-[4-(3-chloro-5-cyano-2-pyridylthio)phenyl]-3-(2-chlorobenzoyl)urea;
1-[4-(3-chloro-5-cyano-2-pyridylthio)phenyl]-3-(2,6-difluorobenzoyl)urea;
1-[4-(3-chloro-5-cyano-2-pyridylthio)phenyl]-3-(2,6-dichlorobenzoyl)urea;
1-[4-(3-chloro-S-cyano-2-pyridylthio)phenyl]-3-(2-chloro-6-fluorobenzoyl)urea;
1-[4-(3-chloro-5-cyano-2-pyridyloxy)-3,5-dimethylphenyl]-3-(2,6-difluorobenzoyl)thiourea;
1-[4-(3-chloro-5-cyano-2-pyridyloxy)-3,5-dibromophenyl]-3-(2,6-difluorobenzoyl)thiourea;
1-[4-(S-cyano-2-pyridyloxy)-3,5-dibromophenyl]-3-(2,6-difluorobenzoyl)thiourea:
1-[4-(5-cyano-2-pyridyloxy)-3,6-dimethyl-5-chlorophenyl]-3-(2,6-difluorobenzoyl)thiourea;
1-[4-(5-cyano-2-pyridyloxy)-3,6-dimethyl-5-chlorophenyl]-3-(4-chlorobenzoyl)urea:
1-[4-(5-cyano-2-pyridyloxy)-3,6-dimethyl-5-chlorophenyl]-3-(4-chlorobenzoyl)thiourea;
1-[4-(5-cyano-2-pyridyloxy)-3,5-dibromophenyl1-3-(4-chlorobenzoyl)thiourea;
1-(4-(3-methyl-5-nitro-2-pyridyloxy)-3,5-dibromophenyl]-3-(2,6-difluorobenzoyl)thiourea.
1-[4-(3-methyl-5-nitro-pyridyloxy)-3,5-dibromophenyl]-3-(4-chlorobenzoyl)thiourea;
1-[4-(3-cyano-5-methyl-2-pyridyloxy)-3,5-dichlorophenyl]-3-(2-chlorobenzoyl)urea:
1-[4-(3-cyano-5-methyl-2-pyridyloxy)-3,5-dichlorophenyl]-3-(2,6-difluorobenzoyl)urea;
1-[4-(3-cyano-5-methyl-2-pyridyloxy)-3,5-dichlorophenyl]-3-(2,6-dichlorobenzoyl)urea;
1-[4-(3-cyano-5-methyl-2-pyridyloxy)-3,5-dichlorophenyl]-3-(2-chloro-6-fluorobenzoyl)urea;
1-[4-(3-(cyano-5-methyl-2-pyridyloxy)-3,5-dichlorophenyl]-3-(2,6-difluorobenzoyl)thiourea;
1-[4-(3-cyano-5-methyl-2-pyridyloxy)-3,5-dichlorophenyl]-3-(4-chlorobenzoyl)thiourea;
1-[4-(3-cyano-5-methyl-2-pyridyloxy)-3,5-dichlorophenyl]-3-(2,6-dimethylbenzoyl)urea;
1-[4-(3-cyano-4,6-dimethyl-2-pyridyloxy)-3,5-dichlorophenyl]-3-(2,6-difluorobenzoyl)urea;
1-[4-(3-cyano-4,,6-dimethyl-2-pyridyloxy)-3,5-dichlorophenyl]-3-(2,6-dichlorobenzoyl)urea;
1-[4-(3-cyano-4,6-dimethyl-2-pyridyloxy)3,5-dichlorophenyl]-3-(2-chlorobenzoyl)urea;
1-[4-(3-cyano-4,6-dimethyl-2-pyridyloxy)-3,5-dichlorophenyl]-3-(2-chloro-6-fluorobenzoyl)urea;
1-[4-(3-cyano-4,6-dimethyl-2-pyridyloxy)-3,5-dichlorophenyl]-3-(2,6-difluorobenzoyl)thiourea;
1-[4-(5-cyano-6-chloro-2-pyridyloxy)-3,5-dichlorophenyl]-3-(2-chlorobenzoyl)urea;
1-(4-(5-cyano-6-chloro-2-pyridyloxy)-3,5-dichlorophenyl]-3-(2,6-difluorobenzoyl)urea;
1-[4-(5-cyano-6-chloro-2-pyridyloxy)-3,5-dichlorophenyl]-3-(2,6-dichlorobenzoyl)urea;
1-[4-(5-cyano-6-chloro-2-pyridyloxy)-3,5-dichlorophenyl]-3-(2,6-difluorobenzoyl)urea;
1-[4-(S-cyano-6-chloro-2-pyridyloxy)-3,5-dimethylphenyl]-3-(2-chlorobenzoyl)urea;
1-[4-(5-cyano-6-chloro-2-pyridyloxy)-3,5-dimethylphenyl]-3-(2,6-difluorobenzoyl)urea;
1-[4-(5-cyano-6-chloro-2-pyridyloxy)-3,5-dimethylphenyl]-3-(2,6-dichlorobenzoyl)urea;
1-[4-(5-cyano-6-chloro-2-pyridyloxy)-3,5-dimethylphenyl]-3-(2-chloro-6-fluorobenzoyl)urea;
1-[4-(5-cyano-6-chloro-2-pyridyloxy)-3,5-dimethylphenyl]-3-(4-chlorobenzoyl)thiourea;
1-[4-(5-cyano-6-chloro-2-pyridyloxy)-3,5-dimethylphenyl]-3-(2-fluorobenzoyl)urea;
1-[4-(3-chloro-5-methyl-2-pyridyloxy)-3,5-dichlorophenyl]-3-(2-chloro-6-fluorobenzoyl)urea;
1-[4-(3-chloro-5-methyl-2-pyridyloxy)-3,5-dichlorophenyl]-3-(2-chlorobenzoyl)thiourea;
1-[4-(3-chloro-5-methyl-2-pyridyloxy)-3,5-dichlorophenyl]-3-benzoyl)thiourea:
1-[4-(3-chloro-5-methyl-2-pyridyloxy)-3-methylphenyl]-3-(2-chlorobenzoyl)urea;
1-[4-(3-chloro-S-methyl-2-pyridyloxy)-2,5-dimethylphenyl]-3-(2,6-difluorobenzoyl)urea;
1-[4-(3,5-dimethyl-2-pyridylthio)-3,5-dichlorophenyl]-3-(2,6-difluorobenzoyl)urea:

1-[4-(3,5-dimethyl-2-pyridylthio)-3,5-dichlorophenyl]-(3-chlorobenzoyl)thiourea:
1-[4-(3,5-dimethyl-2-pyridylsulfonyl-3,5-dichlorophenyl]-3-(2,6-difluorobenzoyl)urea;
1-[4-(3-methyl-5-chloro-2-pyridylthio)-3,5-dichlorophenyl]-3-(2,6-difluorobenzoyl)urea;
1-[4-(3-methyl-5-chloro-2-pyridylthio)-3,5-dichlorophenyl]-3-(2-chlorobenzoyl)thiourea:
1-[4-(3-methyl-5-chloro-2-pyridylsulfonyl)-3,5-dichlorophenyl]-3-(2,6-difluorobenzoyl)urea;
1-[4-(3-methyl-5-chloro-2-pyridylthio)-3-methylphenyl]-3-(2-chlorobenzoyl)urea:
1-[4-(3-methyl-5-chloro-2-pyridylsulfonyl)-3-methylphenyl]-3-(2,6-difluorobenzoyl)urea:
1-[4-(3-methyl-5-bromo-2-pyridylthio)-3,5-dichlorophenyl]-3-(2-chlorobenzoyl)urea:
1-[4-(3,6-dimethyl-2-pyridylthio)-3,5-dichlorophenyl-3-(2,6-difluorobenzoyl)urea;
1-[4-(4,6-dimethyl-2-pyridyloxy)-2,5-dimethylphenyl]-3-(2,6-difluorobenzoyl)urea;
1-[4-(3-chloro-5-methyl-2-pyridyloxy)-2-methyl-5-chlorophenyl]-3-(2-chlorobenzoyl)urea; and
1-[4-(3-chloro-5-methyl-2-pyridyloxy)-2-methyl-5-chlorophenyl]-3-(2-chlorobenzoyl)thiourea.

U.S. patent application Ser. No. 454,847, filed Dec. 30, 1982 abandoned parent application to U.S. Pat. No. 4,659,724, incorporated herein by reference, discloses and claims phenoxyphenyl and phenoxypyridyl urea compounds which may be used in the method of this invention. Such phenoxyphenyl and phenoxypyridyl urea compounds can be prepared by the methods described in the application, and are available from Union Carbide Agricultural Products Company, Inc., Research Triangle Park, N.C. Illustrative of the phenoxyphenyl and phenoxypyridyl urea compounds of U.S. patent application Ser. No. 454,849 which may be useful in the method of this invention include the following:
1-(2,6-dichlorobenzoyl)-3-(3,6-dimethyl-5-chloro-4-[4-(4-chlorophenylsulfonyl)phenoxy]phenyl)urea;
1-(2,6-difluorobenzoyl)-3-(3,6-dimethyl-5-chloro-4-[4-(4-chlorophenylsulfonyl)phenoxylphenyl)urea;
1-(2-chloro-6-fluorobenzoyl)-3-(3,6-dimethyl-5-chloro-4-[4-(4-chlorophenylsulfonyl)phenoxylphenyl) urea:
1-(2-chlorobenzoyl)-3-(3,6-dimethyl-5-chloro-4-[4-(4-chlorophenylsulfonyl)phenoxy]phenyl)urea;
1-(2-methylbenzoyl)-3-(3,6-dimethyl-5-chloro-4-(4-(4-chlorophenylsulfonyl)phenoxy]phenyl)urea;
1-(2-trifluoromethylbenzoyl)-3-(3,6-dimethyl-5-chloro-4-[4-(4-chlorophenylsulfonyl)phenoxy]phenyl) urea;
1-(2,6-dichlorobenzoyl)-3-(3,5-dimethyl-4-[4-(4-chlorophenylsulfonyl)phenoxy]phenyl)urea;
1-(2,6-difluorobenzoyl)-3-(3,5-dimethyl-4-[4-(4-chlorophenylsulfonyl)phenoxy]phenyl)urea;
1-(2-chloro-6-fluorobenzoyl)-3-(3,5-dimethyl-4-[4-(4-chlorophenylsulfonyl)phenoxy]phenyl)urea:
1-(2-chlorobenzoyl)-3-(3,5-dimethyl-4-[4-(4-chlorophenylsulfonyl)phenoxy]phenyl)urea;
1-(2,6-dichlorobenzoyl)-3-(3,6-dimethyl-5-chloro-4-[4-(4-chlorophenylsulfenyl)phenoxy]phenyl)urea;
1-(2,6-difluorobenzoyl)-3-(3,6-dimethyl-5-chloro-4-[4-(4-chlorophenylsulfenyl)phenoxy]phenoxyzphenyl) urea;
1-(2-chloro-6-fluorobenzoyl)-3-(3,6-dimethyl-5-chloro-4-[4-(4-chlorophenylsulfenyl)phenoxy]phenyl) urea:
1-(2-chlorobenzoyl)-3-(3,6-dimethy,1-5-chloro-4-[4-(4-chlorophenylsulfenyl)phenoxy]phenyl)urea;
1-(2-chlorobenzoyl)-3-(3,6-dimethyl-5-chloro-4-[4-(4-chlorophenylsulfenyl)phenoxy]phenyl)thiourea;
1-(2,6-difluorobenzoyl)-3-(3,6-dimethyl-5-chloro-4-(4-(4-chlorophenylsulfenyl)phenoxy]phenyl)thiourea;
1-(2,6-difluorobenzoyl)-3-(3,6-dimethyl-5-chloro-4-[4-(4-chlorophenylsulfonyl)phenoxy]phenyl)thiourea;
1-(2,6-difluorobenzoyl)-3-(3,6-dimethyl-5-chloro-4-[4-(4-chlorophenylsulfinyl)phenoxy]phenyl)thiourea:
1-(2,6-dichlorobenzoyl)-3-(3,6-dimethyl-5-chloro-4-[4-(4-chlorophenylsulfinyl)phenoxy]phenyl)urea;
1-(2-chloro-6-fluorobenzoyl)-3-(3,6-dimethyl-5-chloro-4-[4-(4-chlorophenylsulfinyl)phenoxy]phenyl) urea;
1-(2-chlorobenzoyl)-3-(3,6-dimethyl-5-chloro-4-[4-(4-chlorophenylsulfinyl)phenoxy]phenyl)urea:
1-(2,6-difluorobenzoyl)-3-(3-trifluoromethyl-4-[4-(4-chlorophenylsulfonyl)phenoxy]phenyl)urea;
1-(2,6-dichlorobenzoyl)-3-(3-trifluoromethyl-4-[4-(4-chlorophenylsulfonyl)phenoxy]phenyl)urea;
1-(2-chloro-6-fluorobenzoyl)-3-(3-trifluoromethyl-4-[4-(4-chlorophenylsulfonyl)phenoxy]phenyl)urea;
1-(2-chlorobenzoyl)-3-(3-trifluoromethyl-4-[4-(4-chlorophenylsulfonyl)phenoxy]phenyl)urea:
1-(2,6-difluorobenzoyl)-3-(3,5-dimethyl-4-[4-(4-chlorophenylsulfinyl)phenoxy]phenyl)urea;
1-(2,6-dichlorobenzoyl)-3-(3,5-dimethyl-4-[4-(4 chlorophenylsulfinyl)phenxoy]phenyl)urea;
1-(2-chloro-6-fluorobenzoyl)-3-(3,5-dimethyl-4-[4-(4-chlorophenylsulfinyl)phenoxy]phenyl)urea;
1-(2-chlorobenzoyl)-3-(3,5-dimethyl-4-[4-(4-chlorophenylsulfinyl)phenoxy]phenyl)urea:
1-(2,6-difluorobenzoyl)-3-(2-[4-(4-chlorophenylsulfonyl)phenoxy]-3-bromo-5-pyridyl)urea;
1-(2,6-dichlorobenzoyl)-3-(2-[4-(4-chlorophenylsulfonyl)phenoxy]-3-bromo-5-pyridyl)urea;
1-(2-chloro-6-fluorobenzoyl)-3-(2-[4-chlorophenylsulfonyl)phenoxy]-3-bromo-5-pyridyl)urea:
1-(2-chlorobenzoyl)-3-(2-[4-(4-chlorophenylsulfonyl)phenoxy]-3-bromo-5-pyridyl)urea;
1-(2,6-difluorobenzoyl)-3-(2-[4-(4-chlorophenylsulfonyl)phenoxy]-3-bromo-5-pyridyl)thiourea:
1-(2,6-difluorobenzoyl)-3-(2-[4-(4-chlorophenylsulfenyl)phenoxy]-3-chloro-5-pyridyl)urea;
1-(2,6-dichlorobenzoyl)-3-(2-[4-(4-chlorophenylsulfenyl)phenoxy]-3-chloro-5-pyridyl)urea;
1-(2-chloro-6-fluorobenzoyl)-3-(2-[4-(4-chlorophenylsulfenyl)phenoxy]-3-chloro-5-pyridyl)urea;
1-(2-chlorobenzoyl)-3-(2-[4-(4-chlorophenylsulfenyl)phenoxy]-3-chloro-5-pyridyl)urea;
1-(2,6-difluorobenzoyl)-3-(2-(4-(4-chlorophenylsulfenyl)phenoxy]-3-chloro-5-pyridyl)thiourea:
1-(2,6-difluorobenzoyl)-3-(2-[4-(4-chlorophenylsulfinyl)phenoxy]-3-chloro-5-pyridyl)urea;
1-(2,6-dichlorobenzoyl)-3-(2-[4-(4-chlorophenylsulfinyl)phenoxyl-3-chloro-5-pyridyl)urea;
1-(2-chloro-6-fluorobenzoyl)-3-(2-[4-(4-chlorophenylsulfinyl)phenoxy]-3-chloro-5-pyridyl)urea;
1-(2-chlorobenzoyl)-3-(2-[4-(4-chlorophenylsulfinyl)phenoxy]-3-chloro-5-pyridyl)urea:
1-(2,6-difluorobenzoyl)-3-(2-[4-(4-chlorophenylsulfinyl)phenoxy]-3-chloro-S-pyridyl)thiourea;
1-(2,6-difluorobenzoyl)-3-(3-chloro-4-[4-(2-chloro-4-trifluoromethylphenylsulfenyl)-phenoxy]phenyl)urea;
1-(2,6-dichlorobenzoyl)-3-(3-chloro-4-[4-(2-chloro-4-trifluoromethylphenylsulfenyl)-phenxoy]phenyl)urea;
1-(2,6-dimethylbenzoyl)-3-(3-chloro-4-[4-(2-chloro-4-trifluoromethylphenylsulfenyl)-phenoxy]phenyl)urea;
1-(2-chlorobenzoyl)-3-(3-chloro-4-[4-(2-chloro-4-trifluoromethylphenylsulfenyl)-phenoxy]phenyl)urea;
1-(2,6-difluorobenzoyl)-3-(3-chloro-4-[4-(2-chloro-4-trifluoromethylphenylsulfenyl)-phenoxy]phenyl) thiourea;
1-(2,6-difluorobenzoyl)-3-(3-chloro-4-[4-(2-chloro-4-trifluoromethylphenylsulfonyl)-phenoxy]phenyl)urea;

1-(2,6-dichlorobenzoyl)-3-(3-chloro-4-[4-(2-chloro-4-trifluoromethylphenylsulfonyl)-phenoxy]phenyl)urea;

1-(2-chlorobenzoyl)-3-(3-chloro-4-[4-(2-chloro-4-trifluoromethylphenylsulfonyl)-phenoxy]phenyl)urea;

1-(2,6-difluorobenzoyl)-3-(3--chloro-4-[4-(2-chloro-4-trifluoromethylphenylsulfonyl)-phenoxy]phenyl) thiourea;

1-(2,6-difluorobenzoyl)-3-(3,6-dimethyl-5-chloro-4-(2-chloro-4-(2,4-dimethylphenoxy)-phenoxy]phenyl) urea;

1-(2,6-dichlorobenzoyl)-3-(3,6-dimethyl-5-chloro-4-[2-chloro-4-(2,4-dimethylphenoxy)-phenoxy]phenyl) urea:

1-(2-chlorobenzoyl)-3-(3,6-dimethyl-5-chloro-4-[3-chloro-4-(2,4-dimethylphenoxy)-phenoxy]phenyl)urea;

1-(2-chloro-6-fluorobenzoyl)-3-(3,6-dimethyl-5-chloro-4-[2-chloro-4-(2,4-dimethylphenoxy)-phenoxy]phenyl) urea:

1-(2,6-difluorobenzoyl)-3-(3,6-dimethyl-5-chloro-4-[2-chloro-4-(2,4-dimethylphenoxy)-phenoxy]phenyl) urea;

1-(2,6-dimethoxybenzoyl)-3-(3,6-dimethyl-5-chloro-4-[3-chloro-4-(2,4-dimethylphenoxy)-phenoxy]phenyl) urea;

1-(2,6-difluorobenzoyl)-3-(3,6-dimethyl-5-chloro-4-(2-methyl-4-(2,4-dichlorophenoxy)-phenoxy]phenyl) urea;

1-(2,6-dichlorobenzoyl)-3-(3,6-dimethyl-5-chloro-4-[2-methyl-4-(2,4-dichlorophenoxy)-phenoxy]phenyl) urea:

1-(2-chlorobenzoyl)-3-(3,6-dimethyl-5-chloro-4-(2-methyl-4-(2,4-dichlorophenoxy)-phenoxy]phenyl) urea;

1-(2,6-dimethoxybenzoyl)-3-(3,6-dimethyl-5-chloro-4-[2-methyl-4-(2,4-dimethylphenoxy)-phenoxy]phenyl) urea;

1-(2,6-difluorobenzoyl)-3-(3,6-dimethyl-5-chloro-4-[2-methyl-4-(2,4-dichlorophenoxy)-phenoxy)phenyl) thiourea;

1-(2-chlorobenzoyl)-3-(3,6-dimethyl-5-chloro-4-[3-chloro-4-(2-t-butyl-4-methylphenoxy)-phenoxy] phenyl)urea;

1-(2,6-difluorobenzoyl)-3-(3,6-dimethyl-5-chloro-4-[2-chloro-4-(2-t-butyl-4-methylphenoxy)-phenoxy]phenyl) urea:

1-(2,6-dichlorobenzoyl)-3-(3,6-dimethyl-5-chloro-4-(3-chloro-4-(2-t-butyl-4-methylphenoxy)-phenoxy] phenyl) urea;

1-(2,6-difluorobenzoyl)-3-(3,6-dimethyl-5-chloro-4-[3-isopropyl-4-(2,4-dichlorophenoxy)-phenoxy]phenyl) urea:

1-(2,6-dichlorobenzoyl)-3-(3,6-dimethyl-5-chloro-4-(3-isopropyl-4-(2,4-dichlorophenoxy)-phenoxy]phenyl) urea;

1-(2-chlorobenzoyl)-3-(3,6-dimethyl-5-chloro-4-[2-isopropyl-4-(2,4-dichlorophenoxy)-phenoxy]phenyl) urea;

1-(2-chlorobenzoyl)-3-(3,6-dimethyl-5-chloro-4-[2-isopropyl-4-(2,4-dichlorophenoxy)-phenoxy]phenyl) thiourea;

1-(2-dichlorobenzoyl)-3-(3-chloro-4-[4-(2-chloro-4-t-butylthiophenylsulfonyl)-phenoxy]phenyl)urea;

1-(2,6-difluorobenzoyl)-3-(3,6-dimethyl-5-chloro-4-[4-(4-trifluoromethylphenoxy)phenoxy]phenyl) urea:

1-(2,6-difluorobenzoyl)-3-(3,5-dichloro-4-[4-(4-chlorobenzoyl)phenoxy]phenyl)urea;

1-benzoyl-3-(3,5-dichloro-4-(4-(4-chlorophenylsulfonyl)phenoxy]phenyl)thiourea;

1-(2,6-difluorobenzoyl)-3-(3,5-dichloro-4-[2-trifluoromethyl-4-(4-chlorophenylsulfonyl)phenoxy) phenyl)urea:

1-(2,6-difluorobenzoyl)-3-(2-methyl-5-chloro-4-[4-(4-chlorophenylsulfonyl)phenoxy]phenyl)urea;

1-(2-chlorobenzoyl)-3-(2,5-dimethyl-4-[4-(4-chlorophenylsulfonyl)phenoxy)phenyl)thiourea:

1-(2-chlorobenzoyl)-3-(3-methoxy-4-[4-(4-chlorophenylsulfonyl)phenoxy]phenyl)urea;

1-(2,6-difluorobenzoyl)-3-(3-chloro-4-[4-(2-chloro-4-[4-chlorophenylthio]phenylsulfonyl)-3-methyl-phenoxy] phenyl)urea;

1-(2,6-difluorobenzoyl)-3-(3-chloro-4-[4-(2-chloro-4-[4-chlorophenylsulfinyl]phenylsulfonyl)phenoxy]phenyl) urea;

1-(2,6-difluorobenzoyl)-3-[3,5-dichloro-4-[4-(4-chlorophenoxysulfonyl)phenoxy]phenyl urea;

1-(2,6-difluorobenzoyl)-3-[3,5-dichloro-4-[4-(4-chlorophenylsulfonyloxy)phenoxy]phenyl]urea;

1-(2,6-difluorobenzoyl)-3-[2,5-dimethyl-3-chloro-4-[4-(4-chlorophenoxysulfonlyl)phenoxylphenyl]urea;

1-(2-chlorobenzoyl)-3-[2,5-dimethyl-3-chloro-4-[4-(4-chlorophenoxysulfonyl)phenoxyaphenyl]urea;

1-(2,6-difluorobenzoyl)-3-(3-chloro-4-[2-chloro-4-[4-chlorophenylsulfonlyl)phenylsulfonyl)phenoxy] phenyl) urea;

1-(2,6-difluorobenzoyl)-3-(3-methyl-4-[4-(4-t-butylsulfinylphenylsulfonyl)phenoxy]phenyl)urea:

1-(2,6-difluorobenzoyl)-3-(3-methyl-4-[4-(4-methylthiophenylsulfonyl)phenoxy]phenyl)urea; and 1-(2,6-difluorobenzoyl)-3-(3-methyl-4-[4-(4-methylsulfonylphenylsulfonyl)phenoxy]phenyl)urea.

U.S. patent application Ser. No. 672,007, filed Nov. 15, 1984, incorporated herein by reference, discloses and claims biphenylyloxy and biphenylylalkoxy aryl acyl urea compounds which may be used in the method of this invention. Such biphenylyloxy and biphenylylalkoxy aryl acyl urea compounds can be prepared by the methods described in the application, and are available from Union Carbide Agricultural Products Company, Inc., Research Triangle Park, N.C. Illustrative of the biphenylyloxy and biphenylylalkoxy aryl acyl urea compounds of U.S. patent application Ser. No. (D-14121) which may be useful in the method of this invention include the following:

1-(2,6-difluorobenzoyl)-3-(3-methyl-5-chloro-4-(2-phenylphenoxy)phenyl]urea;

1-(2,6-difluorobenzoyl)-3-[3,5-dimethyl-4-(2-phenyl-4-bromophenoxy)phenyl]urea;

1-(2-chlorobenzoyl)-3-[3,5-dimethyl-4-(2-phenyl-4-bromophenoxy)phenyl]urea;

1-(2,6-difluorobenzoyl)-3-(2,5-dimethyl-3-chloro-4-(2-phenyl-4-methylphenoxy)phenyl]urea:

1-(2-trifluoromethoxybenzoyl)-3-[2,5-dimethyl-3-chloro-4-(2-phenyl-4-methylphenoxy)phenyl]urea;

1-(2-chlorobenzoyl)-3-[2,5-dimethyl-3-chloro-4-(2-phenyl-4-trifluoromethylphenoxy)phenyl]urea:

1-(2-chlorobenzoyl)-3-[3-trifluoromethyl-4-(2-phenylphenoxy)phenyl]urea;

1-(2-nitrobenzoyl)-3-[3-methoxy-4-(2-phenyl-4-ethoxycarbonylphenoxy)phenyl]urea:

1-(2-chlorobenzoyl)-3-[3-ethoxycarbonyl-4-(2-phenyl-4-bromophenoxy)phenyl]urea;

1-(2,6-difluorobenzoyl)-3-[2,5-dimethyl-3-chloro-4-(2-phenyl-4-cyanophenoxy)phenyl]urea:

1-(2,6-difluorobenzoyl)-3-[3,5-dichloro-4-[4-(2-phenyl-4-chlorophenyl)butoxy]phenyl]urea;

1-(2-chlorobenzoyl)-3-[3-carboxy-4-(2-phenyl-4-chlorophenoxy)phenyl]urea;

1-(2,6-difluorobenzoyl)-3-(3,5-dichloro-4-[alpha, alpha-dimethyl-2-phenyl-4-chlorobenzyloxylphenyl]urea;

1-(2-chlorobenzoyl)-3-[2,5-dimethyl-3-chloro-4-(2-phenyl-4-chlorophenoxy)phenyl]urea;

1-(2,6-difluorobenzoyl)-3-[2,5-dimethyl-3-chloro-4-(2-phenyl-4-chlorophenoxy)phenyl]urea;

1-(2-chloro-6-fluorobenzoyl)-3-[2,5-dimethyl-3-chloro-4-(2-phenylphenoxy)phenyl]urea;

1-(2,6-difluorobenzoyl)-3-[3,5-dichloro-4-(2-phenylphenylmethoxy)phenyl]urea:

1-(2,6-difluorobenzoyl)-3-[2,5-dimethyl-3-chloro-4-(2-phenylphenoxy)phenyl]urea;

1-(2-chlorobenzoyl)-3-[2,5-dimethyl-3-chloro-4-(2-phenylphenoxy)phenyl]urea;

1-(2,6-difluorobenzoyl)-3-3, 5-dichloro-4-(alpha-methy 1-(2-phenylbenzyloxy))phenyl]urea;
1-(2-chlorobenzoyl)-3-[3,5-dichloro-4-(alpha-methyl-(2-phenylbenzyloxy))phenyl]urea;
1-(2-trifluoromethylbenzoyl)-3-[2,5-dimethyl-3-chloro-4-(2-phenyl-4-chlorophenoxy)phenyl)urea;
1-(2-methoxybenzoyl)-3-[2,5-dimethyl-3-chloro-4-(2-phenyl-4-chlorophenoxy)phenyl]urea;
1-(2-ethoxybenzoyl)-3-[2,5-dimethyl-3-chloro-4-(2-phenylphenoxy)phenyl]urea;
1-(2-fluorobenzoyl)-3-[3-methoxy-5-chloro-4-(2-phenyl-4-chlorophenoxy)phenyl]urea;
1-(2,6-difluorobenzoyl)-3-[3-trifluoromethoxy-4-(2-phenyl-4-methoxyphenoxy)phenyl]urea;
1-(2,6-difluorobenzoyl)-3-[2,5-dimethyl-3-chloro-4-(2-phenyl-4-trifluoromethoxyphenoxy)phenyl]urea;
1-(2-fluorobenzoyl)-3-[2,5-dimethyl-3-chloro-4-(2-phenyl-4-cyanophenoxy)phenyl]urea;
1-(2,6-difluorobenzoyl)-3-[3,5-dichloro-4-(2-phenyl-4-nitrophenoxy)phenyl]urea;
1-(2,6-difluorobenzoyl)-3-[2,5-dimethyl-3-chloro-4-(3-phenylphenoxy)phenyl]urea;
1-(2,6-dichlorobenzoyl)-3-[3,5-dichloro-4-(2-phenyl-4-carboxyphenoxy)phenyl]urea;
1-(2,6-difluorobenzoyl)-3-[2,5-dimethyl-3-chloro-4-(2-bromo-4-phenylphenoxy)phenyl]urea;
1-(2-chlorobenzoyl)-3-[2,5-dimethyl-3-chloro-4-(2-phenylphenoxy)phenyl]thiourea;
1-(2-fluorobenzoyl)-3-[3-nitro-4-(2-phenyl-4-chlorophenoxy)phenyl]urea;
1-(2-fluorobenzoyl)-3-[2,5-dimethyl-3-chloro-4-(2-phenylphenoxy)phenyl]thiourea;
1-(2-fluorobenzoyl)-3-(2,5-dimethyl-3-chloro-4-(2-phenyl-4-chlorophenoxy)phenyl)urea;
1-(2-ethoxybenzoyl)-3-[3-chloro-5-ethyl-4-(2-phenyl-4-tert-butylphenoxy)phenyl]urea;
1-(2-isopropylbenzoyl)-3-[2,5-dimethyl-3-carboxy-4-(2-phenyl-4-carboxyphenoxy)phenyl]urea dissodium salt;
1-(2,6-difluorobenzoyl)-3-[3-cyano-5-chloro-4-(2-phenyl-4-chlorophenoxy)phenyl]urea;
1-(2,6-difluorobenzoyl)-3-[3-isopropyl-5-methyl-4-(2-phenyl-4-ethoxyphenoxy)phenyl]urea;
1-(2,6-difluorobenzoyl)-3-[2-methyl-5-chloro-4-(2-phenylphenoxy)phenyl]urea; and
1-(2,6-difluorobenzoyl)-3-[2,5-dimethyl-3-chloro-4-(2-(4-chlorophenyl)phenoxy)phenyl]urea.

U.S. patent application Ser. No. 480,697, filed Mar. 31, 1983, incorporated herein by reference, discloses and claims bicyclooxyaryl thiourea compounds which may be used in the method of this invention. Such bicyclooxyaryl thiourea compounds can be prepared by the methods described in the application, and are available from Union Carbide Agricultural Products Company, Inc., Research Triangle Park, N.C. Illustrative of the bicyclooxyaryl thiourea compounds of U.S. patent application Ser. No. 480,697 which may be useful in the method of this invention include the following:
1-[4-(4-chloro-1-naphthoxy)-3,5-dichlorophenyl]-3-(2,6-difluorobenzoyl)thiourea;
1-[4-(4-chloro-1-naphthoxy)-345-dichlorophenyl]-3-(2-chlorobenzoyl)thiourea;
1-[4-(4-chloro-1-naphthoxy)-2,3,5-trichlorophenyl]-3-(2,6-difluorobenzoyl)thiourea;
1-[3-chloro-4-(4-chloro-1-naphthoxy)-2,5-dimethylphenyl]-3-(2,6-difluorobenzoyl)thiourea;
1-[3-chloro-4-(4-chloro-1-naphthoxy)-2,5-dimethylphenyl]-3-(2-chlorobenzoyl)thiourea;
1-[4-(4-chloro-1-naphthoxy)-2,3-dichloro-5-methylphenyl]-3-(2,6-difluorobenzoyl)thiourea;
1-[2-chloro-4-(4-chloro-1-naphthoxy)-3,5-dimethylphenyl]-3-(2,6-difluorobenzoyl)thiourea;
1-[4-(4-chloro-1-naphthoxy)-2,5-dichloro-5-methylphenyl]-3-(2,6-difluorobenzoyl)thiourea;
1-[4-(4-chloro-1-naphthoxy)-3-methylphenyl]-3-(2,6-difluorobenzoyl)thiourea;
1-[5-chloro-4-(4-chloro-1-naphthoxy)-2-methylphenyl]-3-(2,6-difluorobenzoyl)thiourea;
1-[4-(4-chloro-1-naphthoxy)-3,5-dimethylphenyl]-3-(2,6-difluorobenzoyl)thiourea;
1-[3-chloro-4-(4-chloro-1-naphthoxy)-2,5-dimethylphenyl]-3-(2-fluorobenzoyl)thiourea;
1-[4-(4-chloro-5,6,7,8-tetrahydro-1-naphthoxy)-3,5-dichlorophenyl]-3-(2,6-difluorobenzoyl)thiourea;
1-[5-chloro-4-(4-chloro-5,6,7,8-tetrahydro-1-naphthoxy)-2-methylphenyl]-3-(2,6-difluorobenzoyl) thiourea;
1-[3-chloro-4-(4-chloro-5,6,7,8-tetrahydro-1-naphthoxy)-2,5-dimethylphenyl]-3-(2,6-difluoro- benzoyl)thiourea;
1-[3-chloro-4-(4-chloro-5,6,7,8-tetrahydro-1-naphthoxy)-2,5-dimethylphenyl]-3-(2-chlorobenzoyl) thiourea;
1-[3-chloro-2,5-dimethyl-4-[4-(N,N-dimethylamino]-5,6,7,8-tetrahydro-1-naphthoxy]phenyl]-3-(2,6-difluorobenzoyl) thiourea;
1-[3-chloro-2,5-dimethyl-4-[4-(N,N-dimethylamino)-1-naphthoxyl-phenyl]-3-(2,6-difluorobenzoyl)thiourea;
1-[3,5-dichloro-4-[4-(N,N-dimethylamino)-5,6,7,8-tetrahydro-1-naphthoxy]phenyl]-3-(2,6-difluorobenzoyl) thiourea;
1-(3,5-dichloro-4-[4-(N,N-dimethylamino)-1-naphthoxy]-phenyl]-3-(2,6-difluorobenzoyl)thiourea;
1-[3,5-dichloro-4-(4-methoxy-1-naphthoxy)phenyl]-3-(2,6-difluorobenzoyl)thiourea;
1-[3-chloro-4-(4-methoxy-1-naphthoxy)phenyl]-3-(2,6-difluorobenzoyl)thiourea;
1-[3-chloro-4-(1,6-dibromo-2-naphthoxy)phenyl]-3-(2,6-difluorobenzoyl)thiourea;
1-[4-(1,6-dibromo-2-naphthoxy)-3-methylphenyl]-3-(2,6-difluorobenzoyl)thiourea;
1-[3,5-dichloro-(1,6-dibromo-2-naphthoxy)phenyl]-3-(2,6-difluorobenzoyl)thiourea;
1-[4-(6-bromo-2-naphthoxy)-3,5-dichlorophenyl]-3-(2,6-diflurobenzoyl]thiourea;
1-[4-(4-chloro-1-naphthoxy)-3,5-dimethylphenyl]-3-(2,6-difluorobenzoyl)thiourea;
1-[4-(4-chloro-5,6,7,8-tetrahydro-1-naphthoxy)-3,5-dimethylphenyl]-3-(2,6-difluorobenzoyl)thiourea;
1-[3,5-dichloro-4-(2,2-dimethyl-2,3-dihydro-7-benzofuranyloxy)phenyl)-3-(2,6-difluorobenzoyl) thiourea;
1-[2-(4-chloro-1-naphthoxy)-3-methyl-5-pyridyl]-3-(2,6-difluorobenzoyl)thiourea; and
1-[2-(4-methoxy-1-naphthoxy)-3-chloro-5-pyridyl]-3-(2,6-difluorobenzoyl)thiourea.

Other urea compounds disclosed in the art and encompassed within formula 1 may also be used in the method of this invention. Such urea compounds including the preparation thereof are described in the following U.S. Pat. Nos.: 4,271,171; 4,085,226; 4,139,636; 4,310,548; 4,262,020; 4,323,579; 4,234,600; 4,321,276; 4,310,694; 4,089,975; 4,380,641; 4,366,155; 4,405,552; 4,264,605; 4,293,552; 4,338,257; 4,164,581; 4,212,870; 4,276,309; 4,310,530; 4,173,637; 4,344,951; 4,321,388; 4,350,706; 3,992,553; 4,041,177; 4,275,077; 3,748,356; 3,933,908; 3,989,842; 4,160,037; 4,336,264; 4,083,977; 4,148,977; 4,160,902; 4,148,902; 4,166,124; 4,160,834; 4,064,267; 4,005,223; 4,123,449; 4,068,002; 4,194,005; 4,399,152; and 4,013,717.

Other such urea compounds encompassed within formula 1 which may be used in the method of this invention are described in the following patents and published applications: EP 42533; EP 14675; German DE 3,235,419; German DE 3,219,200; German DE 3,041,947; EP 77759; EP 40179; German DE 3,241,138; EP 79311; EP 71279; EP 42732; Belgian 868,228; United Kingdom 2,028,813; German DE 2,726,684; United Kingdom 1,580,876; Japan 5 7128 673; Japan 5 8039 657; Japan Kokai 81 15272; Japan 5 7002 273; Japan Kokai 81 25148; Japan 5 7144 258; EP 31974; EP 88343: Japan Kokai 78 11537; German DE 3,217,619; EP 93977; German DE 3,104,407; EP 57888; Japan 5 9020 265; Japan 5 4012 345; EP 116,728; Japan 5 5038 357; Japan 5 6092 857; Japan 5 7002 258; EP 69288; Japan 5 7002 259; Japan 5 5038 357; Japan 5 8035 163; Japan 5 8039 657; Japan 82 02258; Japan 5 6092 857; Japan 5 6068 659; German DE 3,232,265; German DE 2,541,116; and EP 13414.

Illustrative of other urea compounds which may be useful in the method of this invention include the following:

1-[3,5-dichloro-4-(3,5-dichloro-2-pyridyloxy)phenyl]-3-(2-chloro-6-fluorobenzoyl)urea;
1-[4-(4-chlorophenoxy)-3,5-dichlorophenyl]-3-(2-fluorobenzoyl)urea;
1-[4-(4-chlorophenoxy)-3,5-dichlorophenyl]-3-(2-chloro-6-fluorobenzoyl)urea;
1-[4-(3-chloro-5-trifluoromethyl-2-pyridyloxy)-3,5-dichlorophenyl]-3-(2-chlorobenzoyl)urea;
1-[4-(3-chloro-5-trifluoromethyl-2-pyridyloxy)-3,5-dichlorophenyl]-3-(2-fluorobenzoyl)urea;
1-[4-(3-chloro-5-trifluoromethyl-2-pyridyloxy)-3,5-dichlorophenyl]-3-(2-chloro-6-fluorobenzoyl)urea;
1-[3,5-dichloro-4-(3,5-dichloro-2-pyridyloxy)phenyl]-3-(2,6-difluorobenzoyl)urea;
1-[3,5-dichloro-4-(3,5-dichloro-2-pyridyloxy)phenyl]-3-(2-fluorobenzoyl)urea;
1-[3,5-dichloro-4-(3,5-dichloro-2-pyridyloxy)phenyl]-3-(2-chlorobenzoyl)urea;
1-[4-(3-chloro-5-trifluoromethyl-2-pyridyloxy)-3,5-dichlorophenyl]-3-(2,6-difluorobenzoyl)urea;
1-(4-chlorophenyl)-3-(2,6-difluorobenzoyl)urea;
1-(3,5-dichloro-2,4-difluorophenyl)-3-(2,6-difluorobenzoyl)urea;
1-[3,5-dichloro-4-(1,1,2,2-tetrafluoroethoxy)phenyl]-3-(2,6-difluorobenzoyl)urea;
1-(4-trifluoromethylphenyl)-3-(2,6-difluorobenzoyl)-urea;
1-(4-trifluoromethoxyphenyl)-3-(2-chlorobenzoyl)urea;
1-[5-(4-bromophenyl)-6-methyl-2-pyrazinyl]-3-(2,6-dichlorobenzoyl)urea;
1-[S-(4-bromophenyl)-6-methyl-2-pyrazinyl1-3-(2-chlorobenzoyl)urea;
1-(4-trifluoromethyl-2-thiazoyl)-3-(2,6-dichlorobenzoyl)urea;
1-(2-fluoro-4-iodophenyl)-3-(2,6-difluorobenzoyl) urea;
1-(2,4-difluorophenyl)-3-(2,6-difluorobenzoyl)urea:
1-(4-chloro-2-fluorophenyl)-3-(2,6-difluorobenzoyl) urea:
1-(4-bromo-2-fluorophenyl)-3-(2,6-difluorobenzoyl) urea;
1-[4-(1-phenylethoxy)phenyl]-3-(2,6-difluorobenzoyl) urea;
1-[4-(1-phenylethoxy)phenyl]-3-(2-chlorobenzoyl)urea;
1-[3-chloro-4-(1-phenylpropoxy)phenyl]-3-(2-chlorobenzoyl)urea;
1-(4-benzoyloxyphenyl)-3-(2,6-difluorobenzoyl)urea;
1-(3,5-dichloro-4-benzoyloxyphenyl)-3-(2,6-difluorobenzoyl)urea;
1-(3,5-dimethyl-4-benzyloxyphenyl)-3-(2-chlorobenzoyl) urea;
1-[3,5-dichloro-4-(4-chlorobenzyloxy)phenyl]-3-(2,6-difluorobenzoyl)urea;
1-[3-chloro-4-(5-trifluoromethyl-6-chloro-2-pyridyloxy) phenyl]-3-(2-chlorobenzoyl)urea;
1-[3-methoxycarbonyl-4-(3-chloro-5-(trifluoromethyl)-2-pyridyloxy)-5-methylphenyl]-3-(2,6-difluorobenzoyl)urea;
1-[2,5-dichloro-4-(3-chloro-5-trifluoromethyl-2-pyridyloxy)phenyl]-3-(2,6-difluorobenzoyl)urea;
1-[2,5-dimethyl-4-(3-chloro-5-trifluoromethyl-2-pyridyloxy)-phenyl]-3-(2,6-difluorobenzoyl)urea;
1-[3,5-dichloro-4-(2,2-dichlorocyclopropylmethoxy)-phenyl]-3-(2-chlorobenzoyl)urea;
1-[3,5-dimethyl-4-(2,2-dichlorocyclopropylmethoxy)-phenyl]-3-(2-chlorobenzoyl)urea;
1-[3,5-dimethyl-4-(2,2-dichlorocyclopropylmethoxy)-phenyl]-3-(2,6-dichlorobenzoyl)urea;
1-(5-chloro-2-pyridinyl-N-oxide)-3-(2,6-dichlorobenzoyl) urea;
1-[4-(1,2-dichlorovinyloxy)phenyl]-3-(2,6-difluorobenzoyl)urea; 1[4-(1,1,2,2,-tetrafluoroethoxy)phenyl]-3-(3,5-dichlorobenzoyl)urea;
1-[3-methyl-4-(1,1,2,2-tetrafluoroethoxy)phenyl]-3-(2,6-difluorobenzoyl)urea;
1[4-(1,1,2-trifluoro-2-chloroethylthio)phenyl]-3-(2,6-difluorobenzoyl)urea:
1-[6-methyl-5-(alpha,alpha,alpha-trifluoro-m-tolyl)-2-pyrazinyl]-3-(2-chlorobenzoyl)urea;
1-[5-(4-methoxyphenyl)-6-methyl-2-pyrazinyl)-3-(2-chlorobenzoyl)urea;
1-(5-bromo-2-pyridinyl)-3-(2,6-dichlorobenzoyl)urea:
1-(5-(trifluoromethyl)-2-pyridinyl)-3-(2,6-dichlorobenzoyl)urea;
1-(5-chloro-2-pyridinyl)-3-(2,6-difluorobenzoyl)urea;
1-[6-(4-chlorophenylthio)-3-pyridinyl]-3-(2,6-difluorobenzoyl)urea;
1-[6-(3,5-dichlorophenoxy)-3-pyridinyl)-3-(2,6-dimethoxybenzoyl)urea;
1-[6-(3-(trifluoromethyl)-4-chlorophenylthio]-3-pyridinyl]-3-(2,6-dimethoxybenzoyl)urea:
1-[6-(3,5-bis(trifluoromethyl)phenylthio]-3-pyridinyl]-3-(2,6-dichlorobenzoyl)urea:
1-[6-(2,4-dichlorobenzyloxy)-3-pyridinyl]-3-(2,6-difluorobenzoyl)urea;
1-[6-[2-chloro-5-(trifluoromethyl)phenoxy]-3-pyridinyl]-3-(2,6-difluorobenzoyl)urea;
1-[6-(2,4-dichlorobenzyloxy)-3-pyridinyl1-3-(2-fluoro-6-methoxybenzoyl)urea;
1-[6-(3,5-dichlorophenoxy)-3-pyridinyl]-3-(2-chloro-6-fluorobenzoyl)urea;
1-(6-[4-chloro-3-(trifluoromethyl)phenoxy]-3-pyridinyl]-3-(2-fluoro-6-methoxybenzoyl)urea;
1-[5-(4-chlorophenyl)-2-pyridyl]-3-(2-chloro-6-fluorobenzoyl)urea:
1-[5-(2,4-dichlorophenyl)-2-pyridyl]-3-(2,6-difluorobenzoyl)urea;
1-[5-(4-bromophenyl)-4,6-dimethyl-2-pyridyl]-3-(2,6-difluorobenzoyl)urea;
1-[6-chloro-5-(4-chlorophenyl)-2-pyridyl1-3-(2,6-difluorobenzoyl)urea;
1-[6-bromo-5-(4-bromophenyl)-2-pyridyl]-3-(2,6-difluorobenzoyl)urea;
1-[5-(4-t-butylphenyl)-3-isoxazolyl]-3-(2-chlorobenzoyl) urea;
1-[4-bromo-5-(4-(trifluoromethyl)phenyl)-3-isoxazolyl]-3-(2,6difluorobenzoyl)urea;
1-[4-chloro-5-(4-(trifluoromethyl)phenyl]-3-isoxazolyl]-3-(2,6-difluorobenzoyl)urea;
1-[1-(3,5-bis(trifluoromethyl)phenyl)-5-chloro-1,6-dihydro-6-oxopyridazin-4-yl]-3-(2-chlorobenzoyl) urea;
1-[1-t-butyl-5-chloro-1,6-dihydro-6-oxopyridazin-4-yl]-3-(2,6-difluorobenzoyl)urea;

1-[1-(3,5-bis(trifluoromethyl)phenyl)-S-bromo-1,6-dihydro-6-oxopyridazin-4-yl]-3-(2-chlorobenzoyl) urea;
1-[3,5-dichloro-4-(1,1,2,2-tetrafluoroethoxy)phenyl]-3-(3,5-dichloro-4-pyridinecarbonyl)urea;
1-[3-(3-chloro-5-trifluoromethyl-2-pyridyloxy)-4-methylphenyl]-3-(2,6-difluorobenzoyl)urea;
1-[3-(3-chloro-5-trifluoromethyl-2-pyridyloxy)-4-chlorophenyl]-3-(2,6-difluorobenzoyl)urea;
1-[3-(4-(trifluoromethylphenoxy)phenyl]-3-(2,6-difluorobenzoyl)urea;
1-[4-ethynylphenyl)-3-(2,6-difluorobenzoyl)urea;
1-(3-chloro-4-ethynylphenyl)-3-(2-chloro-6-fluorobenzoyl)urea;
1-[3,5-dichloro-4-(N,N-diallylamino)phenyl]-3-(2,6-difluorobenzoyl)urea;
1-[3,5-dichloro-4-(N-i-propyl-N-allylamino)phenyl]-3-(2,6-difluorobenzoyl)urea;
1-(3,5-dibromo-4-(N-allyl-N-methylamino)phenyl]-3-(2,6-difluorobenzoyl)urea;
1-[3,5-dichloro-4-(3'-chloroallyloxy)phenyl]-3-(2,6-difluorobenzoyl)urea;
1-[3,5-dichloro-4-alloxyphenyl]-3-(2,6-difluorobenzoyl) urea;
1-[3,5-dichloro-4-(1',2'-dichlorovinyloxy)phenyl]-3-(2-fluorobenzoyl)urea;
1-[3,5-dichloro-4-(3'-bromoallylthio)phenyl]-3-(2-fluorobenzoyl)urea;
1-[4-trifluoromethylthiophenyl)-3-(2,6-difluorobenzoyl) urea;
1-(4-trifluoromethoxyphenyl)-3-(2,6-difluorobenzoyl) urea;
1-[3-chloro-4-(2-chloro-1,1,2-trifluoroethoxy)phenyl]-3-(2,6-difluorobenzoyl)urea;
1-[3-(trifluoromethyl)-4-bromophenyl]-3-(2-chlorobenzoyl) urea;
1-[3,4-(tetrafluoroethylenedioxy)phenyl)-3-(2,6-difluorobenzoyl)urea:
1-(3,4-(difluoromethylenedioxy)phenyl]-3-(2-fluorobenzoyl)urea:
1-[4-(t-butoxycarbonylphenyl]-3-(2-chlorobenzoyl) urea;
1-[3-chloro-4-(t-butoxycarbonyl)phenyl]-3-(2-chlorobenzoyl)urea;
1-[4-(1-hydroxy-1-trifluoromethyl-2,2,2-trifluoroethyl)phenyl]-3-(2,6-difluorobenzoyl)urea;
1-[4-(1-hydroxy-1-trifluoromethyl-2,2,2-trifluoroethyl)phenyl]-3-(4-chloroethenoyl)urea;
1-[2,5-dimethyl-4-(1-hydroxy-1-trifluoromethyl-2,2,2-trifluoromethyl)phenyl)-3-(2-chlorobenzoyl)urea;
1-[3,5-dichloro-4-(2-chloro-4-(trifluoromethylsulfonyl)phenoxy]phenyl[-3-(2,6-difluorobenzoyl)urea;
1-[3,5-dichloro-4-(3-trifluoromethyl-5-chloro-2-pyridyloxy)phenyl]-3-(2,6-difluorobenzoyl)urea;
1-[3,5-dichloro-4-(5-chloro-2-pyrimidinyloxy)phenyl]-3-(2,6-dichlorobenzoyl)urea;
1-[3,5-dichloro-4-(5-chloro-2-pyrimidinyloxy)phenyl]-3-(2,6-difluorobenzoyl)urea;
1-[3,5-dichloro-4-(3-chloro-5-trifluoromethyl-2-pyridyloxy)phenyl]-3-(2,6-dimethoxybenzoyl)urea:
1-[2,6-dichloro-3-pyridyl]-3-(2,6-difluorobenzoyl) urea;
1-]5-chloro-2-benzothiazolyll-3-(2,6-difluorobenzoyl) urea;
1-[5-bromo-2-benzoxazolyl]-3-(2,6-difluorobenzoyl) urea;
1-(3,5-dichloro-4-(4-chlorophenoxy)phenyl]-3-(2-hydroxycarbonylbenzoyl)urea;
1-[2-ethyl-4-(ethoxycarbonyl)-5-oxazolyl]-3-(2,6-difluorobenzoyl)urea;
1-[3,5-dichloro-4-(3-chloro-5-(2,2-dichloro-1,1,2-trifluoroethyl)-2-pyridyloxy)phenyll-3-(2,6-difluorobenzoyl)urea:

1-(2,3,4,5-tetrachlorophenyl)-3-(2,6-difluorobenzoyl) urea;
1-[3,5-dichloro-4-(N-(2-methoxyethyl)-N-methylamino)phenyl]-3-(2,6-difluorobenzoyl)urea;
1-[3,5-dichloro-4-(N-(3-methoxypropyl)-N-methylamino)phenyl]-3-(2-chlorobenzoyl)urea;
1-[3,5-dichloro-4-(N-n-decyl-N-methylamino)phenyl]-3-(2-chlorobenzoyl)urea;
1-[3,5-dichloro-4-(N-n-hexyl-N-methylamino)phenyl]-3-(2,6-difluorobenzoyl)urea;
1-(2,3,4,5-tetrafluorophenyl)-3-(2-chloro-6-fluorobenzoyl) urea;
1-(2,3,4,5-tetrafluorophenyl)-3-(2-chlorobenzoyl) urea;
1-(2,3,4,5-tetrachlorophenyl)-3-(2,6-difluorobenzoyl) thiourea;
1-[3,5-dichloro-4-(5-chloro-2-pyrimidinyloxy)phenyl]-3-(2,6-difluorobenzoyl)thiourea;
1-[3,5-dichloro-4-(2-bromo-4-trifluoromethylsulfonylphenoxy)phenyl]-3-(2-chlorobenzoyl)thiourea:
1-[3,4-(difluoromethylenedioxy)phenyl]-3-(2-chlorobenzoyl)thiourea;
1-[4-chloro-3-(4-(trifluoromethyl)phenyl)-5-isoxazolyl)-3-(2-chlorobenzoyl)thiourea;
1-[3,5-dichloro-4-(3-chloro-5-trifluoromethyl-2-pyridyloxy)phenyl]-3-(2,6-difluorobenzoyl)thiourea:
1-(4-(2-chloro-4-trifluoromethylphenoxy)-3,5-dichlorophenyl)-3-(2,6-difluorobenzoyl)urea;
1-(4-(2-chloro-4-trifluoromethylphenoxy)-3,5-dichlorophenyl)-3-(2-chlorobenzoyl)urea;
1-(4-(2-chloro-4-trifluoromethylphenoxy)phenyl)-3-(2,6-difluorobenzoyl)urea;
1-(4-(2-chloro-4-trifluoromethylphenoxy)phenyl)-3-(2-chlorobenzoyl)urea:
1-(4-(2-chloro-4-trifluoromethylphenyl)-2,5-dimethylphenyl)-3-(2,6-difluorobenzoyl)urea;
1-(4-(2-chloro-4-trifluoromethylphenyl)-2,5-dimethylphenyl)-3-(2-chlorobenzoyl)urea;
1-(4-(2-chloro-4-trifluoromethylphenoxy)-2,3,5-trimethylphenyl)-3-(2,6-difluorobenzoyl)urea;
1-(4-(2-chloro-4-trifluoromethylphenoxy)-2,3,5-trimethylphenyl)-3-(2-chlorobenzoyl)urea:
1-(4-(2-chloro-4-trifluoromethylphenoxy)-2,3,6-trimethylphenyl)-3-(2,6-difluorobenzoyl)urea;
1-(4-(2-chloro-4-trifluoromethylphenoxy)-2,3,6-trimethylphenyl)-3-(2-chlorobenzoyl)urea;
1-(4-(2-chloro-4-trifluoromethylphenoxy)-2,3,5,6-tetramethylphenyl)-3-(2,6-difluorobenzoyl)urea;
1-(4-(2-chloro-4-trifluoromethylphenoxy)-2,3,5,6-tetramethylphenyl)-3-(2-chlorobenzoyl)urea;
1-(3-chloro-4-(2-chloro-4-trifluoromethylphenoxy)-2,5-dimethylphenyl)-3-(2,6-difluorobenzoyl)urea;
1-(3-chloro-4-(2-chloro-4-trifluoromethylphenoxy)-2,5-dimethylphenyl)-3-(2-chlorobenzoyl)urea;
1-(3,5-dichloro-4-(4-trifluoromethylphenoxy)phenyl)-3-(2,6-difluorobenzoyl)urea;
1-(3-chloro-2,5-dimethyl-4-(4-trifluoromethylphenoxy)phenyl)-3-(2,6-difluorobenzoyl)urea;
1-(4-trifluoromethylphenoxy)-2,3,5-trimethylphenyl)-3-(2,6-difluorobenzoyl)urea;
1-(3,5-dichloro-4-(2,4-dichlorophenoxy)phenyl)-3-(2,6-difluorobenzoyl)urea:
1-(4-(2-bromo-4-chlorophenoxy)-3,5-dichlorophenyl)-3-(2,6-difluorobenzoyl)urea;
1-(4-(2-bromo-4-chlorophenoxy)-3,5-dichlorophenyl)-3-(2-fluorobenzoyl)urea;
1-(4-(2,4-dichlorophenoxy)phenyl)-3-(2,6-difluorobenzoyl) urea;

1-(4-(2,4-dichlorophenoxy)phenyl)-3-(2-chlorobenzoyl) urea;
1-(4-(4-chlorophenoxy)-3,5-dichlorophenyl)-3-(2,6-difluorobenzoyl)urea;
1-(3-chloro-2,5-dimethyl-4-(4-nitrophenoxy)phenyl)-3-(2,6-difluorobenzoyl)urea;
1-(3-chloro-2,5-dimethyl-4-(4-nitrophenoxy)phenyl)-3-(2-chlorobenzoyl)urea;
1-(3-chloro-4-(2-chloro-4-nitrophenoxy)-2,5-dimethylphenyl)-3-(2,6-difluorobenzoyl)urea;
1-(3-chloro-4-(2-chloro-4-nitrophenoxy)-2,5-dimethylphenyl)-3-(2-chlorobenzoyl)urea;
1-(3-chloro-4-(3,5-dichloro-2-pyridyloxy)-2,5-dimethylphenyl)-3-(2,6-difluorobenzoyl)urea;
1-(3-chloro-4-(3,5-dichloro-2-pyridyloxy)-2,5-dimethylphenyl)-3-(2-chlorobenzoyl)urea;
1-(3-chloro-4-(3-chloro-5-trifluoromethyl-i-pyridyloxy)-2,5-dimethylphenyl)-3-(2,6-difluorobenzoyl)urea;
1-(3-chloro-4-(3-chloro-5-trifluoromethyl-i-pyridyloxy)-2,5-dimethylphenyl)-3-(2-chlorobenzoyl)urea;
1-(3-chloro-4-(3-chloro-5-trifluoromethyl-i- pyridyloxy)-2,5-dimethylphenyl)-3-(2-fluorobenzoyl)urea;
1-(3-chloro-4-(3-chloro-5-trifluoromethyl-i-pyridyloxy)-2,5-dimethylphenyl)-3-(2,6-dichlorobenzoyl)urea;
1-(2,6-difluorobenzoyl)-3-[4-(7,9-dimethyldibenzofuranyl)]-urea;
1-(2,6-difluorobenzoyl)-3-[4-(9-chlorodihydrobenz-(f,f)oxepinyl)]urea;
1-(2,6-difluorobenzoyl)-3-[4-(2,10-dichlorodihydro-7-fluoro-3-methyl-dibenz(f,f)oxepinyl)]urea;
1-(2 6-difluorobenzoyl)-3-[4-(10-chloro-6,7-dihydro-8-fluoro-dibenz(b,g)oxocinyl)]urea;
1-(3,5-dichloro-4-(4-nitrophenoxy)phenyl]-3-(2,6-difluorobenzoyl)urea;
1-(3,5-dichloro-4-(4-nitrophenoxy)phenyl]-3-(2-chlorobenzoyl)urea;
1-[3,5-dichloro-4-(2-chloro-4-nitrophenoxy)phenyl]-3-(2,6-difluorobenzoyl)urea;
1-[3,5-dichloro-4-(4-cyanophenoxy)phenyl]-3-(2-chlorobenzoyl)urea;
1-[3,5-dichloro-4-(3,5-dichloro-2-pyridyloxy)phenyl]-3-(2,4,6-trifluorobenzoy)urea;
1-[3,5-dichloro-4-(3,5-dichloro-2-pyridyloxy)phenyl)-3-(2,4-difluorobenzoyl)urea;
1-[3,5-dichloro-4-(3,5-dichloro-2-pyridyloxy)phenyl]-3-(2,5-difluorobenzoyl)urea;
1-[3,5-dichloro-4-(3-chloro-5-trifluormethyl-2-pyridyloxy)phenyl]-3-(2,4,6-trifluorobenzoyl)urea;
1-[2,5-dimethyl-3-chloro-4-(2-bromo-4-chlorophenoxy)-phenyl]-3-(2-chloro-4-fluorobenzoyl)urea;
1-[2,5-dimethyl-3-chloro-4-(2-bromo-4-chlorophenoxy)-phenyl]-3-(2-chloro-5-fluorobenzoyl)urea;
1-[2,5-dimethyl-3-chloro-4-(2-bromo-4-chlorophenoxy)-phenyl]-3-(2,4,6-trifluorobenzoyl)urea;
1-[3,5-dichloro-4-(3-chloro-4-cyanophenoxy)phenyl]-3-(2-chlorobenzoyl)urea;
1-(3,S-dichloro-4-(3-chloro-5-bromo-2-pyridyloxy)-phenyl]-3-(2,6-difluorobenzoyl)urea;
1-(3,5-dichloro-4-(3,5-dibromo-2-pyridyloxy)phenyl]-3-(2,6-difluorobenzoyl)urea; 3-P-chlorophenyl-5-(2,6-difluorobenzoyl)-2,3,5,6-tetrahydro-4H-1,2,5-oxadiazinone-4:
1[4-chlorophenyl]-3-(2,6-difluorobenzoyl)-hydantion; and 1-[4-chlorophenyl]-3-(2,6-difluorobenzoyl)-parabanic acid.

It is appreciated that the particular urea compounds listed hereinabove are illustrative of urea compounds which may be used in the method of this invention. The method of this invention is not to be construed as being limited only to the use of these urea compounds: but rather, the method of this inventon includes those urea compounds encompassed within, formula 1 hereinabove. The term "parasites" as used in the specification and claims is meant to encompass all endoparasites and ectoparasites of warm-blooded animals as well as pests that breed in the manure of the animals.

In particular, representative parasites which may be controlled by the method of this invention include members of the Arthropoda, including mites of the suborders Mesostigmata, Sarcoptiformes, Trombidiformes and Onchychopalpida; sucking and biting lice of the orders Anoplura and Mallophaga: ticks of the families Ixodidae and Argasidae: fleas of the families Pulicidae, Ceratophyllidae, and others; Cimex and other Hemiptera; Triatoma and other Heteroptera: and myiasis-related fly larvae and blood sucking adults (including mosquitoes) of the suborders Brachycera, Cyclorrhapha and Nematocera. Representative also are helminths included in the Nematoda (Strongylida, including but not limited to Strongyloidea, Ancylostomatoidea, Trichostrongyloidea and Metastrongyloidea; Ascarida [Ascaris]; Filariina, such as but not limited to Onchocerca and Dirofilaria; Rhabditida; and Trichinellida); Cestoidea, especially Cyclophyllidea, and Trematoda, including Strigeatoidea such as Schistosoma; Echinostomida such as Fasciola: and Plagiorchiida such as Paraqonimus. Other parasites which may be controlled by compounds represented by generic formula 1 include Acanthocephala such as Macracanthorhynchus, Onicola or Moniliformis, and Pentastomida, especially Linguatula; and Protozoa, especially Coccidia such as Eimeria and Plasmodium, Piroplasmea such as Babesia; Toxoplasmea such as Trypanosoma; Trichomonadidae such as Trichomonas and Entamoebidae such as Entamoeba.

Illustrative of specific parasites of various host animals which may be controlled by the method of this invention include arthropods such as mites (mesostigmatids, itch. mange, scabies, chiggers), ticks (soft-bodied and hard-bodied), lice (sucking, biting), fleas (dog flea, cat flea, oriental rat flea), true bugs (bed bugs, kissing bugs), blood-sucking adult flies (horn fly, horse fly, stable fly. black fly. deer fly, louse fly, tsetse fly, punkies, mosquitoes), and parasitic fly maggots (bot fly, blow fly, screwworm, cattle grub, fleeceworm); helminths such as nematodes (threadworm, lungworm, hookworm, whipworm, nodular worm, stomach worm, round worm, pinworm, heartworm), cestodes (tapeworms) and trematodes (liver fluke, blood fluke); protozoa such as *coccidia, trypanosomes, trichomonads, amoebas* and *plasmodia; acanthocephalans* such as thorny-headed worms; and pentastomids such as tongueworms.

Also, the acyl urea compounds of formula 1 may be administered to a vertebrate definitive host for control of arthropod intermediate hosts which feed on the feces of the vertebrate host. For example, an arthropod intermediate host of helminths and other disease and nuisance-causing organisms, which arthropod host feeds on the feces of a vertebrate host treated with one or more acyl urea compounds of formula 1. can be controlled by the method of this invention.

The method of parasite control of this invention is of the systemic type. The acyl urea compounds of formula 1 are useful parasiticides for the systemic control of endoparasites and ectoparasites which feed on living tissues of warm-blooded animals. These acyl urea compounds have the ability to permeate the living tissues of a host animal to which one of the acyl urea compounds is administered.

Endoparasites and ectoparasites which consume blood or other livng tissues of the host animal ingest or contact the acyl urea compound with which the tissue is permeated, and are thereby killed. It is believed that the blood is an agency through which the acyl urea compound is dispersed through the host animal. However, as illustrated in the working examples hereinafter, systemic control is observed from topical (pour-on) applications of acyl urea compounds of formula 1, thereby indicating that the acyl urea compounds permeate other tissues as well as blood. The acyl urea compounds of formula 1 are also effective for the control of pests which breed in the manure of warm-blooded animals.

Endoparasites and ectoparasites which feed on the living tissues of animals are killed by the acyl urea compounds of formula 1. Those parasites which suck the host animal's blood, those which burrow into and feed on the animal's tissue, and those, like the larvae of bot flies, which enter a natural orifice of the host, attach to the mucous membranes, and feed therefrom may be all equally effectively killed.

It is understood that the parasites mentioned above are not confined to the single host animal with which each is generally identified. Certain parasites inhabit various hosts, although most parasites have a favorite host. For example, the mange mite attacks at least horses, hogs, mules, humans, dogs, cats, foxes, rabbits, sheep, and cattle. Horseflies freely attack horses, mules, cattle, hogs, dogs, and most other animals. Use of the acyl urea compounds of formula 1 kills parasites of the types described above growing in various host animals. For example, these acyl urea compounds may be effective in cats, goats, camels, and zoo animals.

The parasites controlled by the method of this invention normally affect warm-blooded animals. Representative of animals affected are humans and domestic animals such as cattle, horses, sheep, goats, poultry, swine, dogs, and cats.

The time, manner, and rates at which the acyl urea compounds are effectively administered may be varied over a wide range. The acyl urea compounds can be administered to the animals at rates from about 0.01 to about 1000 mg./kg of animal body weight. The best rate for killing a given parasite infesting a given animal must be determined individually, but it is generally found that in most cases the optimum rate is within the preferred range of from about 0.25 to 100 mg./kg. of animal body weight. The optimum rate for a given instance depends on such factors as the activity of the specific acyl urea compound employed, the method of administration, the level of infestation, the duration of control desired, the health of the animal to be treated, the susceptibility of the parasite of primary concern, the expense which can be borne by the animal, and the degree of control desired. The acyl urea compounds of formula 1 are effective when administered at any time of year to animals of any age. It is possible to administer these acyl urea compounds to the animals continuously, as by constant feeding of a diet which contains one of the acyl urea compounds, and thus assure that all parasites which contact the treated animal will be killed. Such administration, however, may not be economical, and it will often be found best to administer the acyl urea compound at such times as to give the best return of parasite control for the compound expended. Certain parasites have a known active season when they attack animals. If such a parasite is of primary importance, the acyl urea compounds can be used only during the active season with assurance of year-round control of the parasite. Other parasites infest and bite animals essentially the year round. Control of such parasites can still be accomplished with, relatively brief periods of administration by administering the acyl urea compounds to all the animals on a farm or in an area for a short period of time, such as for a few weeks. All the parasites of a generation are thus killed, and the animals can be expected to remain parasite-free for a considerable length of time.

Oral administration of an acyl urea compound of formula 1 may be performed by mixing the acyl urea compound in the animal's feed or drinking water, vitamin or mineral supplement, or by administering oral dosage forms such as drenches, tablets, bolus, salt block or capsules. Such oral means of administration are well known in the art.

Percutaneous administration may be conveniently accomplished by subcutaneous, dermal, intramuscular, and even intravenous injection of the injection devices as well as needle-less air-blast injection devices may be useful. Percutaneous administration is also meant to include surface treatment of the animal by dipping (drenching), pour-on, spraying, or dusting. As illustrated in the working examples hereinafter, systemic control is observed from surface treatments of the acyl urea compounds of formula 1.

Sustained action of the acyl urea compounds of formula 1 can be obtained by formulating the acyl urea compound in a matrix which will physically inhibit dissolution. The formulated matrix is injected into the body where it remains as a depot from which the compound slowly dissolves. Matrix formulations, now well known in the art, can be formulated in waxy semisolids such as vegetable waxes and high molecular weight polyethylene glycols.

Even more effective sustained action may be obtained by introducing into the animal an implant containing one of the acyl urea compounds of formula 1. Such implants are well known in veterinary art. Such administration can be highly economical and efficacious, because a properly designed implant maintains a constant concentration of the acyl urea compound in the tissues of the host animal. An implant can be designed to supply the acyl urea compound for several months, and can easily be inserted in the animal. No further handling of the animal or concern over the dosage is necessary after the insertion of the implant.

Percutaneous administration of formula 1 acyl urea compounds may be carried out in the ways usual in the animal veterinary art. For example, it may be practical to formulate an injectable suspension of the acyl urea compound as a fine powder, suspended in a formulation of physiologically-acceptable liquid carriers, surfactants, and suspending agents.

The liquid carriers can be, for example, a vegetable oil such as peanut oil, corn oil, or sesame oil, a glycol such as a polyethylene glycol, or water, depending on the acyl urea compound chosen.

Suitable physiologically acceptable adjuvants may be necessary to keep the acyl urea compound of formula 1 suspended. The adjuvants can be chosen from among the emulsifiers, such as salts of dodecylbenzene sulfate and toluenesulfonate, ethylene oxide adducts of alkylphenol, and oleate and laurate esters, and from the dispersing agents such as salts of naphthalenesulfonate, lignin sulfonate and fatty alcohol sulfates. Thickeners such as carboxymethyl cellulose, polyvinylpyrrolidone, gelatin and the alginates may also be used as adjuvants for injectable suspensions. Many classes of surfactants, as well as those which have been discussed above, serve to suspend the acyl urea compound. For example, lecithin and the polyoxyethylene sorbitan esters may be useful surfactants.

The acyl urea compounds used in the method of this invention can be administered to the animal directly in an undiluted form or the active compound may be formulated with a suitable carrier prior to use. A suitable carrier for purposes of this invention is a carrier which will have no deleterious effect on the animal being treated or on the method or results of the invention. The carrier can be either solid or liquid depending upon the compound and method of administration selected by one skilled in the art. Suitable liquid carriers include water, N-methylpyrrolidone, vegetable oil, and other non-toxic liquid carriers with or without surfactants. Liquid concentrates can be prepared by dissolving one of the active compounds with a non-toxic solvent and dispersing the toxicants in water with the aid of suitable surface active emulsifying and dispersing agents. The choice and quantity of dispersing and emulsifying agents employed is dictated by the ability of the agent to facilitate dispersion of the toxicant. For a solid formulation such as a powder, tablet, paste, or the like, the active ingredient is dispersed in and on an appropriate carrier such as clay, talc, or dry molasses.

Formulations useful in the conduct of the method of this invention can also contain other optional ingredients such as stabilizers or other biologically active compounds, insofar as they do not impair or reduce the activity of the compounds towards the parasites and do not harm the animal being treated.

The formulation of veterinary additives in animal feed is an extremely well-known art. It is usual to formulate the compound first as a premix in which the acyl urea compound of formula 1 is dispersed in a liquid or particulate solid carrier. The premix may conveniently contain from about 1 to 400 grams of compound per pound of carrier, depending on the desired concentration of the feed.

The premix is in turn formulated into feed by dispersing it in the feed mixture in a conventional mixer. The correct amount of acyl urea compound, and hence of premix, to mix in the feed can be easily computed by taking into account the weight of the animals, the approximate amount each animal eats per day.and the concentration of the compound in the premix.

Likewise, the amount of acyl urea compound to administer in the drinking water of animals can be computed by taking into account the animal's weight and the amount each animal drinks per day. It is convenient to use a suspendable formulation of the desired acyl urea compound. The formulation may be a suspension in the concentrated form which is mixed into the drinking water, or may be a dry preparation which is mixed with and suspended in the drinking water. In either event, the acyl urea compound should be in a finely-powdered form. The acyl urea compounds can easily be formulated into tablets and capsules according to the conventional methods known in the art. Drench formulations comprise the acyl urea compound dissolved or dispersed in an aqueous liquid mixture. It is convenient and efficacious to use a dispersion of the acyl urea compound made in the same way that the drinking water formulations discussed above are made.

It is appreciated that the acyl urea compounds of generic formula 1 may be used in combination with each other and/or with one or more biologically active materials, e.g., medicinal drugs, vertebrate toxicants, growth promoters, vitamins, minerals, etc., known in the veterinary art. Such combinations may be used for the known or other purpose of each ingredient and may provide a synergistic effect. The combinations may be administered according to the known or other methods for administering the biologically active materials. e.g.. orally. implant, pour-on, injection, etc.

Illustrative of medicinal drugs known in the veterinary art which may be used in combination with the acyl urea compounds of formula 1 include, for example, the following: benzylbenzoate +lindane; benzylbenzoate; chloroform +rotenone; caraway oil +petrolatum; chlordane; chlorpyrifos; crotoxyphos +dichlorvos; coumaphos; diazinon; dichlorvos; dimethoate; dioxathion; famophos; fenthion; calcium polysulfide; lindane: malathion; methoprene; methoxychlor; benzylbenzoate +lindane +chlorobutanol +phenylmercuric chloride: naled: nicotine sulfate; phosmet; pyrethrins: synergized pyrethrins such as piperonyl butoxide and the like; stabilene, MGK 11 or MGK 326; stirofos +dichlorvos; ronnel; rotenone; stirofos; amicarbalide diisethionate; amprolium; decoquinate; carbarsone; dimetridazole; diminazine aceturate; ethidium bromide; furazolidone; homidium bromide; imidocarb dipropionate; isometamidium; lasalocid; nitarsone; pamaquine napthoate; phenamidine isethionate; phenanthridinium; butynorate +sulfanitran +dinsed +roxarsone; quinacrine hydrochloride; quinacrine hydrochloride +diiodohydroxyquin: quinapyramine sulfate; quinuronium sulfate: ronidazole; sulfamethazine; sulfaquinoxaline sodium; suramin; amphotericin B; griseofulvin; nystatin; benzalkonium chloride +chlordantoin; salicylic acid +benzoic acid; thiabendazole; albendazole; tolnaftate; neomycin +bactracin +polymyxin B sulfate +hydrocortisone acetate; chloroform +rotenone; triethylanolamine polypeptide oleoate condensate +chlorobutanol +propylene glycol; ephedrine sulfate; hydrocortisone acetate +neomycin sulfate; 2-mercaptobenzothiozole +benzocaine +2-chloro-4-phenlphenol; prednisolone acetate +sodium sulfacetamide +neomycin sulfate; nystatin +neomycin sulfate +thiostrepton +triamcinolone acetonide; resorcinol +zinc oxide +calamine +oil of cade +pyroligneous acid +zinc hydride; resorcin +bismuth subgallate +bismuth subnitrate +zinc oxide +calamine +oil of cade; penicillin G sodium; phenylephrine hydrochloride; phenylmercuric nitrate; dimethyl pthalate +cotton seed oil; thymol +ethyl alcohol; thiabendazol +neomycin sulfate +dexamethasone; albendazole +neomycin sulfate +dexamethasone; thiabendazole-piperazine phosphate; aracoline acetarsol; arecoline hydrobromide; arsenamide; bephenium embonate; bephenium hydroxynapthoate; bunamdine hydrochloride; N-butyl chloride; canbendazole; carbondisulfide; diethylcarbamazine citrate; dichlorophen; dichlorophen-toluene; disophenol; dithiazanine iodide; fenbendazole; haloxon; hexylresorcinol; hygromycin; lead arsenate; levamisole; mebendazole; oxfendazole; niclosamide; piperazine-carbondisulfide complex; phenothiazine; phthalofyne; piperazine hexahydrate; piperazine salt of niclosamide, adipate, chloride, citrate, dihydrochloride, hexahydrate, phosphate, and sulfate; pyrantel embonate; pyrantel pamoate; pyrantel tartrate; sutadimethoxine-ormetoprin; styrylpyridinium-diethycarbamazine; themium closylate; thiophanate; tylosin; tetracyline; carbadox; lincomycin; flavomycin; bacitracin; virginiamycin; amprolium; ethopabate; robenidine: arprinocid; monensin; chlorotetracyclin; sulfa compounds; dibutyltin dialurate; lasalocid; salinomycin; narasin; diethylcarbanazine; phenothiazine; metronidazole; nitrothiazole; ipronidazole; sulfamethiazine; amprolium; nitroturazone; diaveridine +sulfaquinoxaline; sulfaquinoxaline; chloroquine; quinacrine; levamisole; ivermectin; avermectin; milbemycin; methyridine; crotamiton; ampicillin; lincomycin; cephalothrin; and amoxicillin trihydrate +clavulanate potassium.

Illustrative of vertebrate toxicants known in the veterinary art which may be used in combination with the acyl area compounds of formula 1 include, for example, the following: coumafuryl: pivalin; warfarin; dicumarol; coumachlor; coumatetralyl; chlorophacinon; diphenacoum: bromethacoum; bromethalin; brodifacoum; bromodiolone +sulpha quinoxaline; bromodiolone; calciferol; calciferol +any anticoagulant such as difenacoum; calcium carbide; calcium phosphide; alpha-chloralose; chlorophacinone; chloropicrin; cholecalciterol; coumafuryl; coumatetryl; crimidine; difenacoum; endrin; floroacetamide; lindane +teenazine +thiourea; acetylsalicylic acid +any anticoagulant such as difenacoum; pindone +warfarin; pyranocoumarin: scillirocide and toxic extracts of Urginea: strychine; thalium sulfate; and zinc phosphide. Such combinations may be administered, for example, as a bait or tracking powder in which an undesirable vertebrate host can be eliminated by the toxicant and, at the same time, any ectoparasites from the dead vertebrate host can be killed and prevented from moving to infect man or his domestic animals by the systemic action of the acyl urea compound.

Illustrative of growth promoters known in the veterinary art which may be used in combination with the acyl urea compounds of formula 1 include, for example, the following: 2,4 - dihydro - 6 -phenyl - 1H - s - triazolo [4,3-a][1,4] benzodiazepin- 1- ones as described in U.S. Pat. No. 3,786, 149; 2,3 - dibromopropanol as described in U.S. Pat. No. 3,934,037; tertiary alcohols and their urea, ureide, oxyurea and carbamate derivatives as described in U.S. Pat. No. Reissue 28,691; tropine benzohydryl ether or 3 - quinuclidinyl benzohydryl ether as described in U.S. Pat. No. 3,978, 221; polyhaloaldehyde aldol condensation products as described in U.S. Pat. No. 3,755,601: nituroxazide as described in U.S. Pat. No. 4,093,747; phenylalkylsulfamide derivatives as described in U.S. Pat. No. 3,860,723; quinoxalinedi - N-oxides as described in U.S. Pat. No. 4,012,512; imines of quinoxalinedi—N—oxides as described in U.S. Pat. Nos. 3,997,665, 3,983,235, 3,984,553, 3,984,550, 3,984,547 and 3,983,236; streptomycetes antibiotics including avermectin, ivermectin, milbemycin, valinomycin and the like as described in U.S. Pat. No. Reissue 28,700 and U.S. Pat. Nos. 4,083,964, 3,950,515, 4,073,884, and 3,790,667; mixtures of mocimycin and bacitracin as described in U.S. Pat. No. 3,928,573; vancomycin, ristocetin and physiologically acceptable salts and esters thereof as described in U.S. Pat. No. 3,928,571; dibenzazepines as described in U.S. Pat. No. 3,812,255; hydroxyphenethanol amines as described in U.S. Pat. No. 3,818,101; bromo FES derivatives and chloro FES derivatives as described in U.S. Pat. Nos. 3,751,431 and 3,764,614; tetrahydroiminobenzo [G] thien-4-ylureas as described in U.S. Pat. No. 4,060,627; pyrazoles as described in U.S. Pat. 3,980,794; thiolcarbamates as described in U.S. Pat. No. 3,781,440; iodonium salts as described in U.S. Pat. No. 4,087,554: 3 —nitro—pyrazole—gamma—carboxylic acid nitrofurfurylidene hydrazides as described in U.S. Pat. No. 4,235,995; macrotrolides such as nonactin, monactin, dinastin, trinactin, tetranactin, polynactin and the like as described in DE 2835936 A 790222 79091: penicillin, cephalosporin and analogs thereof as described in DE 7932285A 790125 79051; and spiramycin and acid esters thereof as described in DE 861603A 780607 78241.

Illustrative of vitamins known in the veterinary art which may be used in combination with the acyl urea compounds of formula 1 include, for example, vitamins A,B,C,D,E, thiamine and the like.

Illustrative of essential minerals known in the veterinary art which may be used in combination with the acyl urea compounds of formula 1 include, for example, sodium, calcium, magnesium, copper, zinc, cobalt, phosphorous, sulfur, chlorine, iodine and the like.

It is understood that the above biologically active materials are merely representative of a wide variety of materials that can be combined with the acyl urea compounds of formula 1 for use in the method of this invention.

The inherent low mammalian toxicity of these compounds by all routes of entry makes them ideally suited for medical and veterinary parasite control. There may also be a reduced probability of pest resistance developing to this chemical class relative to compounds which are dependent upon cholinesterase-inhibition. When administered orally, by pour-on, by implant, or by injection, the costly expense of spray equipment and labor for spraying are eliminated. Problems associated with coverage and penetration of feathers or hair are also avoided.

The method of this invention including the preparation of acyl urea compounds of formula 1 utilized therein is illustrated by the following examples.

EXAMPLE I

Preparation of 1-[3-chloro-4-(4-chloro-1-naphthoxy)-2,5-dimethylphenyl]-3-(2-chlorobenzoyl) urea Part A: Preparation of 3-chloro-4-(4- chloro-1-naphthoxy)-2,5-dimethyl-1-nitrobenzene Into a solution containing 9.10 grams (51.1 mmol) of 4-chloro-1-naphthol and 10.12 grams (46.0 mmol) of 3-chloro-2,5-dimethyl-1-nitrobenzene in 22 milliliters of dimethylsulfoxide at room temperature and under a nitrogen atmosphere was added 8.89 grams (64.4 mmol) of anhydrous potassium carbonate. The resulting mixture was heated to a temperature of 130° C. and maintained at that temperature for a period of 6 hours. The reaction mixture was then filtered and the filtrate was diluted with 20 milliliters of methanol and allowed to cool to room temperature. Crystallization occurred during this cooling period. The filtrate was further cooled in an ice bath, filtered and the collected crystals washed with cold methanol. Recrystallization from a hexane-ethyl acetate mixture afforded 7.92 grams of 3-chloro-4-(4-chloro-1-naphthoxy)-2,5-dimethyl-1-nitrobenzene as a white solid having a melting point of 135°C.–137° C.

Part B: Preparation of 3-chloro-4-(4-chloro-1-naphthoxy)-2,5-dimethylaniline

Into a solution containing 13.8 grams (38.1 mmol) of 3-chloro-4-(4-chloro-1-naphthoxy)- 2,5-dimethyl-1-nitrobenzene prepared in Part A in 400 milliliters of toluene was added 2.0 grams of a 5% platinum on carbon catalyst. The resulting mixture was placed in a one liter rocking Parr hydrogenation vessel. Hydrogen was introduced into the vessel to a pressure of 120 psi. The hydrogen pressure was maintained between 100–120 psi until hydrogen uptake ceased. The contents of the reactor vessel were then removed and filtered. Removal of the solvents from the filtrate afforded 11.6 grams of 3-chloro-4-(4-chloro-1-naphthoxy)-2,5-dimethylaniline as a white solid having a melting point of 118° C.–125° C.

Part C: Preparation of 1-r3-chloro-4-(4-chloro-1-naphthoxy)-2,5-dimethylphenyl]-3-(2-chlorobenzoyl) urea Into a solution containing 3.0 grams (9.0 mmol) of 3-chloro-4-(4-chloro-1-naphthoxy)-2,5-dimethylaniline prepared in Part B in 25 milliliters of toluene which solution was warmed to a temperature of 50° C. and placed under a nitrogen atmosphere was slowly added a solution containing 2.5 grams (13.8 mmol) of 2-chlorobenzoyl isocyanate in 5 milliliters of toluene. After stirring for 1 hour at a temperature of 50° C., the reaction mixture was cooled to room temperature, placed in an ice bath, and filtered through a Buchner funnel. The collected solid was dried under vacuum at a temperature of 50° C. to afford 3.15 grams of 1-(3-chloro-4-(4-chloro-1-naphthoxy)-2,5-dimethylpheny 1]-3-

(2- chlorobenzoyl)urea as a white solid having a melting point of 187° C. Elemental analysis of the white solid indicated the following:

Analysis: $C_{26}H_{19}Cl_3N_2O_2$ Calculated: C. 60.77; H. 3.73; N. 5.45 Found: C. 60.82; H. 3.76; N. 5.76 This compound is referred to hereinafter as Compound 1.

EXAMPLE II

Preparation of 1-[3-chloro-4-(4-chloro-1-naphthoxy) -2,5-dimethylphenyl-3-(2,6-difluorobenzoyl) urea Into a solution containing 3.0 grams (9.0 mmol) of 3-chloro-4-(4-chloro-1-naphthoxy)-2,5-dimethylaniline prepared in Part B of Example I in 25 milliliters of toluene which solution was warmed to a temperature of 50° .C and placed under a nitrogen atmosphere was slowly added a solution containing 2.5 grams (13.5 mmol) of 2,6-difluorobenzoyl isocyanate in 5 milliters of toluene. After stirring for one hour at a temperature of 50° C. the reaction mixture was cooled to room temperature, placed in an ice bath. and filtered through a Buchner funnel. The collected solid was dried under a vacuum at a temperature of 50° C. to afford 2.89 grams of 1-[3-chloro-4-(4-chloro-1-naphthoxy)-2,5-dimethylphenyl]-3-(2,6-difluorobenzoyl) urea as a white powder havin a melting point of 187° C. Elemental analysis of the white powder indicated the following:

Analysis $C_{26}H_{18}Cl_2F_2N_2O_3$ Calculated: C. 60.59; H. 3.52: N. 5.44 Found: C. 59.95; H. 3.28; N. 6.19

This compound is referred to hereinafter as Compound 2.

EXAMPLE III

Preparation of 1-[3-chloro-4-(2,4-dimethylphenoxy) -2,5-dimethylphenyl]-3-(2,6-difluorobenzoyl)urea Part A: Preparation of 4-(2,4-dimethylphenoxy)-2,5-dimethyl-3-chloronitrobenzene Into a round bottom reaction flask equipped with a magnetic stirrer. condenser, thermometer and nitrogen inlet was added 50.0 grams (0.23 mol) of 2,5-dimethyl-3,4-dichloronitrobenzene. 38.5 grams (0.32 mol) of 2,4-dimethylphenol. So grams (0.36 mol) of potassium carbonate and 125 milliliters of dimethylformamide. The reaction mixture was heated to a temperature of 90° C.–100° C. and maintained at this temperature for a period of 72 hours. The reaction mixture was then cooled, filtered and concentrated to give a dark oil. The dark oil was partitioned between toluene (300 milliliters) and 4% sodium hydroxide (250 milliliters) and then separated. The organic layer was washed with water and brine, dried over $Na_2SO_4$ and concentrated to give a dark oil. The dark oil was trituated with hexane and a solid was formed. The solid was washed with cold hexane and vacuum dried to give 47.8 grams (0.16 mol) of 4-(2,4-dimethylphenoxy) 2,5-dimethyl-3-chloronitrobenzene as a tan powder having a melting point of 78° C.–80° C. Elemental analysis of the tan powder indicated the following:

Analysis: $C_{16}H_{16}ClNO_3$ Calculated: C, 62.85; H, 5.27; N. 4.58 Found: C, 63.47; H, 5.35; N. 4.49

Part B: Preparation of 4-(2,4-dimethylphenoxy)-2,5-dimethyl-3-chloroaniline

Into a solution of 4-(2,4-dimethylphenoxy)-2,5-dimethylphenyl-3-chloronitrobenzene (25 grams. 81.8 mmol) prepared in Part A in toluene (250 milliliters) was added a 5% platinum on carbon catalyst (1.0 gram). The resulting mixture was placed in a one liter rocking Parr hydrogenation vessel. Hydrogen was introduced into the vessel to a pressure of 20 psi and maintained at this pressure for a period of 4.5 hours. The contents of the reactor vessel were then removed, filtered through celite and concentrated to give 24.5 grams of an oil. After high vacuum drying. the oil turned to a pinkish solid which was identified as 4-(2,4-dimethylphenoxy)-2,5-dimethyl-3-chloroaniline having a melting point of 86° C.–88° C. Elemental analysis of the solid indicated the following:

Analysis: $C_{16}H_{18}ClNO$ Calculated: C. 69.69; H. 6.53; N. 5.08 Found: C. 70.02; H. 6.60; N. 5.68

Part C: Preparation of 1-[3-chloro-4-(2,4-dimethylphenoxy)-2,5-dimethylphenvl]-3-(2,6-difluorobenzoyl) urea Into a solution of 4-(2,4-dimethylphenoxy)-2,5-dimethyl-3-chloroaniline (1.75 grams. 6.3 mmol) prepared in Part B in 7 milliliters of toluene, which solution was warmed to a temperature of 50° C. was added 1.14 grams (6.2 mmol) of 2,6-difluorobenzoyl isocyanate in 1.5 milliliters of toluene. The reaction mixture was heated to a temperature of 90° C. and maintained at this temperature for 0.5 hours. After cooling to room temperature, the reaction mixture was diluted with 20 milliliters of hexane and then cooled in an ice bath. A precipitate formed which was collected by filtration and washed with a cold solution of 50% hexane in toluene. After vacuum drying. a white solid (1.26 grams) which was identified as 1-[3-chloro-4-(2,4-dimethylphenoxy)-2,5-dimethylphenyl]-3-(2,6-difluorobenzoyl)urea was obtained having a melting point of 183° C.–185° C. Elemental analysis of the white solid indicated the following:

Analysis: $C_{24}H_{11}N_2O_3ClF_2$ Calculated: C, 62.82; H. 4.61; N. 6.10 Found: C. 62.94; H. 4.88; N. 6.03

This compound is referred to hereinafter as Compound 3.

EXAMPLE IV

Preparation of 1-[4-(4-chloro-1-naphthoxy)-2,3,5-trichlorophenyl]-3-(2,6-difluorobenzoyl)urea Part A: Preparation of 4-(4-chloro-1-naphthoxy)-3,5-dichloronitrobenzene Into a mixture of 3,4,5-trichloronitrobenzene (30.26 grams, 134.0 mmol), anhydrous potassium carbonate (28.02 grams, 203.0 mmol) and dimethylformamide (300 milliliters) was added solid 4-chloronaphthol (30,04 grams, 168,0 mmol). The mixture was stirred under a nitrogen atmosphere and heated overnight at a temperature of 105° C. The mixture was then allowed to cool and the dimethylformamide was evaporated under reduced pressure. The residue was dissolved in 1:1 ethyl acetate:ethyl ether (1,5 liters) and washed sequentially with water, 5% NaOH solution, water and brine. The organic layer was dried over $Na_2SO_4$ and concentrated under reduced pressure to afford a crude product as a dark brown solid (48.73 grams). Decolorization with carbon and recrystallization (2x) from hexane:ethyl acetate afforded pure 4-(4-chloro-1-naphthoxy)-3,5-dichloronitrobenzene (15.84 grams, 42.98 mmol, 32%) as a yellow solid having a melting point of 121.5° C.–123° C. This material was characterized by $^1$H-NMR spectroscopy as follows: $^1$H-NMR (CDCl$_3$) 8.70–8.10 (m. 2H). 8.38 (s, 2H), 7.90–7.50 (m, 2H), 7.33 (d, J=9Hz. 1H). 6.25 (d, J=9Hz, 1H).

Part B: Preparation of 4-(4-chloro-1-naphthoxv)-3,5-dichloroaniline

Into a 500 milliliter Parr bottle was charged 4-(4-chloro-1-naphthoxy)-3,5-dichloro- nitrobenzene (15.84 grams, 42.97 mmol) prepared in Part A and toluene (250 milliliters). The bottle was purged thoroughly with nitrogen and 5% platinum on carbon (0.50 grams) was added immediately following the purge. The reaction mixture was then hydrogenated for 1.5 hours on a rocking Parr hydrogenator at a pressure of 90–100 psi hydrogen at ambient temperature. The reaction mixture was filtered through a pad of celite and the filtrate concentrated under reduced pressure to afford pure 4-(4-chloro-1-naphthoxy)-3,5-dichloroaniline (13.99 grams, 41.31 mmol, 96%) as a white solid having a melting point of 145° C.–147° C. Elemental analysis of the white solid indicated the following:

Analysis: $C_{16}H_{10}Cl_3NO$
Calculated: C, 56.75; H, 2.98; N, 4.14
Found: C, 56.96; H, 2.94; N, 4.14

Part C: Preparation of 4-(4-chloro-1-naphthoxy)-2,3,5-trichloroaniline

Into a magnetically stirred solution of 4-(4-chloro-1-naphthoxy)-3,5-dichloroaniline (6.00 grams, 17.72 mmol) prepared in Part B in benzene (50 milliliters) was added solid N-chlorosuccinimide (2.84 grams, 21.20 mmol). The mixture was heated to reflux for 1 hour, cooled and filtered. The solvent was evaporated under reduced pressure and the crude product when subjected to flash column chromatography (3:1 hexane:ethyl acetate) afforded pure 4-(4-chloronaphthoxy)-2,3,5-trichloroaniline (3.70 grams, 9.92 mmol, 56%). Elemental analysis of the product indicated the following:

Analysis: $C_{16}H_9Cl_4NO$
Calculated: C, 51.51; H, 2.43; N, 3.75
Found: C, 51.78; H, 2.49; N, 3.69

Part D: Preparation of 1-[4-(4-chloro-1-naphthoxy)-2,3,5-trichlorophenyl-3-(2,6-difluorobenzoyl)urea Into a magnetically stirred solution of 4-(4-chloro-1-napthhoxy)-2,3,5-trichloroaniline (1.60 grams, 4.29 mmol) prepared in Part C in dichloromethane (20 milliliters) was added neat 2,6-difluorobenzoyl isocyanate (786 milligrams, 4.29 mmol). The heterogeneous mixture was stirred at room temperature for about 15 minutes and then chilled to a temperature of 0° C. The precipitate was collected on a fritted disc and washed with 3:1 hexane:ethyl acetate to afford pure 1-[4-(4-chloro-1-naphthoxy)-2,3,5-trichlorophenyl]-3-(2,6-difluorobenzoyl) urea (1.9 grams, 3.41 mmol, 80%) as a white powder having a melting point of 213° C.–215° C. Elemental analysis of the white powder indicated the following:

Analysis: $C_{24}H_{12}Cl_4F_2N_2O_3$
Calculated: C, 51.83; H, 2.17; N, 5.04
Found: C, 51.41; H, 2.54; N, 4.91

This compound is referred to hereinafter as Compound 4.

EXAMPLE V

Preparation of 2-(2-chlorobenzoyl)-3-[3-chloro-4-(4-chloro-1-naphthoxy)-2,5-dimethyl-phenyl]-1,1-dimethylquanidine Part A: Preparation of 1-(2-chlorobenzoyl)-3-[3-chloro-4-(4-chloro-1-naphthoxy)-2,5-dimethylphenyl]-S-methylisothiourea Into a solution containing 21.2 grams of 1-[3-chloro-4-(4-chloro-1-naphthoxy)-2,5-dimethyl-phenyl]-3-(2-chlorobenzoyl)thiourea and 200 milliliters of dry tetrahydrofuran under an atmosphere of nitrogen and cooled to 10° C. was added 6.3 milliliters (6.4 grams) of 1,8-diaza-bicyclo[.5.4.0] undec-7-ene. The resulting solution was warmed to room temperature and stirred for 20 minutes. After cooling the resultant mixture to a temperature of 10° C., 2.5 milliliters (5.7 grams) of methyl iodide was added. After 5 minutes at 10° C. the mixture was warmed to room temperature, stirred for 2 hours, and then poured into 500 milliliters of ethyl acetate. This solution was washed twice with water and the organic layer dried over anhydrous sodium sulfate. Removal of the solvents afforded 21.14 grams of an orange solid. Recrystallization of the orange solid using a hexane-ethyl acetate mixture afforded 11.29 grams of 1-(2-chlorobenzoyl)-3-[3-chloro-4-(4-chloro-1-naphth-oxy)-2,5-dimethylphenyl]-S-methylisothiourea as white crystals having a melting point of 165° C.–168° C. Elemental analysis of the white crystals indicated the following:

Analysis: $C_{27}H_{21}Cl_3N_2O_2S$
Calculated: C, 59.62; H, 3.89; N, 5.15
Found: C, 59.87; H, 3.89; N, 5.02

Part B: Preparation of 2-(2-chlorobenzovl)-3-[3-chloro-4-(4-chloro-1-napthoxy)-2,5-dimethylphenyl]-1,1-dimethylcuanidine.

A mixture containing 5.0 grams of 1-(2-chlorobenzoyl)-3-[3-chloro-4-(4-chloro-1-naphthoxy)-2,5-dimethylphenyl]-S-methylisothiourea prepared in Part A, 25 milliliters of tetrahydrofuran, 10 milliliters of ethanol and 50 milliliters of a 40% aqueous dimethylamine solution was refluxed in a nitrogen atmosphere for 5 hours. An additional 25 milliliters of 40% aqueous dimethylamine solution was added and reflux was continued for an additional 16 hours. After cooling to room temperature, the mixture was poured into 200 milliliters of water. This aqueous mixture was extracted twice with methylene chloride and twice with ethyl acetate. The combined extracts were dried over anhydrous sodium sulfate. Removal of the solvents afforded 3.97 grams of a crude material. Chromatography of the crude material on silica gel using 9:1 ethyl acetate:methanol for elution afforded 1.87 grams of 2-(2-chlorobenzoyl)-3-[3-chloro-4-(4-chloro-1-naphthoxy)-2,5-dimethylphenyl]-1,1-dimethylguanidine as an amphomorous solid having a melting point of 85° C.–97° C. Elemental analysis of the amphomorous solid indicated the following:

Analysis: $C_{28}H_{24}Cl_3N_3O_2$
Calculated: C, 62.18; H, 4.47; N, 7.77
Found: C, 62.10; H, 4.22; N, 8.00

This compound is referred to hereinafter as Compound 49.

EXAMPLE VI

Preparation of 1-(4-tert-butyldimethylsiloxy- 3,5-dichlorophenyl)-3-(2,6-difluorobenzoyl)urea Into a homogeneous solution of 1-(3,5-dichloro-4-hydroxyphenyl)-3-(2,6-difluoro-benzoyl)urea (3.13 grams, 8.66 mmol) in dimethylformamide (25 milliliters) was added triethylamine (1.75 grams, 17.3 mmol), and the resulting mixture was stirred for 5 minutes. Tertiary-butyldimethylsilyl chloride (3.92 grams, 26.0 mmol) was then added, and a thick precipitate formed immediately. This heterogeneous mixture was then diluted with ethyl acetate (200 milliliters), washed with saturated sodium bicarbonate (twice with 150 milliliters) and then washed with a brine solution (150 milliliters). The organic layer was dried over sodium sulfate, filtered, and concentrated under reduced pressure to give a brown solid. The solid was washed with cold ether and vacuum dried to afford 1-(4-tert-butyldimethyl-siloxy-3,5-dichlorophenyl)-3-(2,6-difluorobenzoyl)urea (2.71 grams, 5.70 mmol) having a melting point of 184° C.–186° C. Elemental analysis of the product indicated the following:

Analysis: $C_{20}H_{22}Cl_2F_2N_2O_3Si$
Calculated: C, 50.52; H, 4.66: N, 5.89
Found: C, 50.47; H, 4.71; N, 5.69

This compound is referred to hereinafter as Compound 45.

EXAMPLE VII

In a manner similar to that employed in the preceeding examples, other urea compounds were prepared. Compounds 5, 6, 7, 14, 18, 21, 22, 23, 29, 32, 33, 34, 39, 43, 48, 68, 78 and 85 were prepared in a manner similar to that employed in Examples I and II for the preparation of Compounds 1 and 2 respectively. Compounds 8, 10, 12, 15, 24, 28, 55, 56, 57, 58, 61, 62, 63, 71, 73, 74, 76, 77, 87, 89, 90, 91, 92, 93 and 98 were prepared in a manner similar to that employed in Example III for the preparation of Compound 3. Compound 79 was prepared in manner similar to that employed in Example V for the preparation of Compound 49. Compounds 25, 37, and 41 were prepared in a manner similar to the procedure described in U.S. patent application Ser. No. 480,697, filed Mar. 31, 1983. Compound 19 was prepared in a manner similar to the procedure described in U.S. Pat. No. 4,521,426. Compound 26 was prepared in a manner similar to the procedure described in U.S. patent application Ser. No. 712, 197, filed Mar. 15, 1985. Compounds 30, 53, 64, 94, 95, 96, 97 and 99 were prepared in a manner similar to the precedure described in U.S. patent application Ser. No. 781,382, filed Sep. 30, 1985. Compounds 69 and 72 were prepared in a manner similar to the procedure described in U.S. patent application Ser. No. 672,007, filed Nov. 15, 1984. Compound 65 was prepared in a manner similar to the procedure described in U.S. patent application Ser. No. 686,735, filed Dec. 27, 1984.

The following compounds were prepared in a manner similar to that described in the indicated publication: Compound 16 (U.S. Pat. No. 3,748,356); Compound 36 (U.S. Pat. No. 3,748,356); Compound 47 (U.S. Pat. No. 3,748,356); Compound 17 (U.S. Pat. No. 4,275,077); Compound 20 (U.S. Pat. No. 4,275,077); Compound 27 (U.S. Pat. No. 4,457,943); Compound 31 (U.S. Pat. No. 4,139,636); Compound 9 (U.S. Pat. No. 4,041,177); Compound 88 (U.S. Pat. No. 4,005,223); Compound 35 (EP 72,438); Compound 54 (EP 69,288); Compound 59 (EP 72,438); Compound 46 (U.S. Pat. No. 4,212,870); Compound 75 (U.S. Pat. No. 4,162,330); Compound 80 (U.S. Pat. No. 4,162,330); Compound 11 (U.S. Pat. No. 4,173,637); Compound 13 (U.S. Pat. No. 4,173,637); and Compound 60 (Japan 56 092857).

The following intermediate anilines and aromatic amines were prepared in a manner similar to that described in the indicated publication, and were then reacted with the appropriate benzoyl isocyanate according to the procedure employed in Example II above: 5-amino-3-methyl-1,2,4-oxadiazole described in U.S. Pat. No. 3,917,478 (Compound 82); 2-amino-5-(1-naphthyl) methylthio-1,3,4-thiadiazole described in German Patent 1,079,060 (Compound 38); 5-(4-nitrophenyl)-3-trifluoromethyl-1,2,4-oxadiazole described in U.S. Pat. No. 3,917,478 (Compound 50) in which the reduction conditions of Example I, Part B above were used to prepare the corresponding aniline; 1-chloro-4-nitronaphthalene described in Bassilios, *Bull. Soc. Chim. Fr.*, 1951, 651 in which catalytic reduction (Example I, Part B above) afforded 1-amino-4-chloronaphthalene (Compound 40); 1-chloro-4-nitronaphthalene was converted into 1-amino-4-(2,4-dimethylphenoxy) naphthalene according to U.S. patent application Ser. No. 495,331, filed May 20, 1983 (Compound 42); 9-nitroanthracene was reduced using the procedure described in Example I, Part B above (Compound 44); 1-amino-4-chloro-5,6,7,8-tetrahydronaphthalene described in Press and Hoffman, *Org. Prep. Proc. Int.*, 1982, 14,204 and Simonetta Beltrane. *Gazz. Chim. Ital.*, 1958, 88,769 (Compound 70); 3,5-dichloro-4-[4-chloro-1-naphthoxy)butoxy] aniline and 4-[1-(1-naphthyl) ethoxy] aniline described in U.S. patent application Ser. No. 430,368, filed Sep. 30, 1982 (Compounds 66 and 81); 1,1-bis-(4-chlorophenyl)methylamine and alpha-methyl-4-chlorobenzylamine described in Cram and Guthrie, *J. Am. Chem. Soc.*, 1966, 88, 5760 (Compounds 83 and 84); and alpha-amino-4-chlorophenylacetonitrile described in Stevens et al., *J. Chem. Soc.*, 1931, 2568 (Compound 86). Compounds 51 and 52 were prepared from commercially available anilines or amines according to the procedure employed in Example II above.

Compound 67 was prepared according to the procedure described in Example II above. The aniline used in this procedure was prepared as follows: A mixture containing 32.81 grams of 3-chloro-2,5-dimethyl-4-(2,4-dimethylphenoxy)aniline, 36.40 grams of methyl bromoacetate, 16.44 grams of anhydrous potassium carbonate and 240 milliliters of toluene was heated to reflux for 66 hours. The reaction mixture was then cooled to room temperature, diluted with 700 milliliters of ethyl acetate, and washed with 400 milliliters of water and 400 milliliters of brine solution. The organic layer was dried over anhydrous sodium sulfate and the solvents removed under reduced pressure. The residue was triturated with hexane to afford 28.32 grams of methyl N-[3-chloro-2,5-dimethyl-4-(2,4-dimethylphenoxy)phenyl] glycinate as an off white solid. $^1$H-NMR(CDCl$_3$): δ 2.12(s, 3H), 2.28(s, 3H), 2.31(s,3H), 2.37(s,3H), 3.81(s,3H), 3.97(s,2H), 6.17(d, J=8Hz, 1H), 6.29(s,1H), 6.78(d of d: J=8, 2Hz , 1H), 7.01(broad d, J=2Hz ,1H).

The structure and analytical data for Compounds 1 through 99, which compounds are used in the examples hereinafter for controlling certain endoparasites and ectoparasites of warm-blooded animals, are set forth in Table 1 below:

TABLE 1

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 1 | 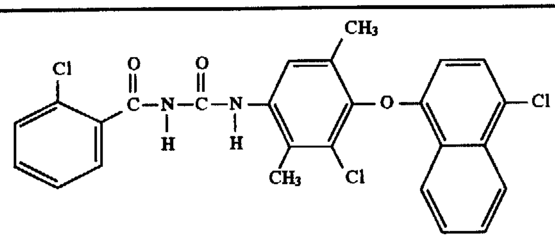 | 60.77 | 3.73 | 5.45 | 61.53 | 3.95 | 5.36 | 187 |
| 2 | 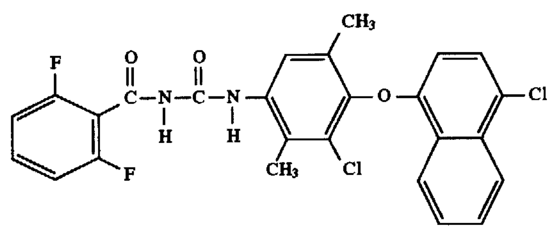 | 60.59 | 3.52 | 5.44 | 59.95 | 3.28 | 6.19 | 187 |
| 3 | 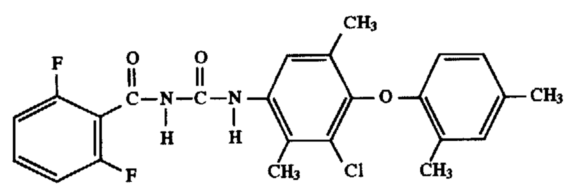 | 62.82 | 4.61 | 6.10 | 62.94 | 4.88 | 6.03 | 183–185 |
| 4 | 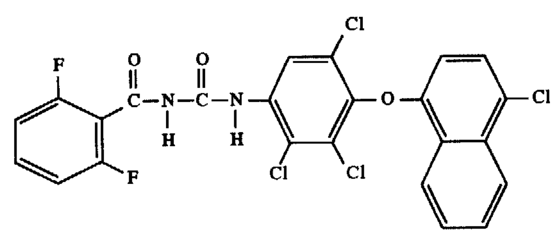 | 51.83 | 2.17 | 5.04 | 51.41 | 2.54 | 4.91 | 213–215 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 5 | (structure) | 55.25 | 2.51 | 5.37 | 55.56 | 2.46 | 5.36 | 237–239 |
| 6 | (structure) | 64.93 | 3.98 | 5.83 | 63.93 | 3.92 | 6.14 | 206 |
| 7 | (structure) | 62.03 | 4.41 | 5.57 | 60.03 | 4.15 | 5.49 | 224–226 |
| 8 | (structure) | 58.43 | 4.09 | 5.68 | 58.72 | 4.18 | 5.68 | 221–222.5 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 9 | [structure: 3,5-dichloro-4-(4-nitrophenoxy)phenyl with CO-NH-CO-NH-2,6-difluorophenyl] | 49.81 | 2.30 | 8.72 | 49.84 | 2.19 | 8.66 | 229–231 |
| 10 | [structure: 3,5-dichloro-4-(4-chlorophenoxy)phenyl with CO-NH-CO-NH-2,6-difluorophenyl] | 50.93 | 2.35 | 5.94 | 50.98 | 2.66 | 5.96 | 198–198.5 |
| 11 | [structure: 3,5-dichloro-4-(3-chloro-5-trifluoromethyl-2-pyridyloxy)phenyl with CO-NH-CO-NH-2,6-difluorophenyl] | 1H-NMR (DMSO-d6): δ11.66 (s, 1H), 10.46 (s, 1H), 8.61 (br s, 2H), 7.96 (s, 2H), 7.01–7.86 (m, 3H). | | | | | | 203–205 |
| 12 | [structure: 3-chloro-4-(4-bromo-2,3-dimethylphenoxy)-3,5-dimethylphenyl with CO-NH-CO-NH-2,6-difluorophenyl] | 53.60 | 3.75 | 5.21 | 53.27 | 3.78 | 5.07 | 198–200 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 13 | [structure: 3,5-dichloro-pyridyloxy-dichlorophenyl acyl urea with 2,6-difluorobenzoyl] | 45.00 | 1.79 | 8.28 | 44.95 | 1.67 | 8.39 | 229–230 |
| 14 | [structure: 4-chloro-naphthyloxy-methylphenyl acyl urea with 2,6-difluorobenzoyl] | 64.31 | 3.67 | 6.00 | 64.03 | 3.49 | 5.92 | 233 |
| 15 | [structure: 2,4-dichlorophenoxy-chloro-dimethylphenyl acyl urea with 2,6-difluorobenzoyl] | 52.87 | 3.03 | 5.61 | 52.91 | 3.07 | 5.65 | 188–190 |
| 16 | [structure: 4-chlorophenyl acyl urea with 2,6-difluorobenzoyl] | 1H-NMR (DMSO-d6): δ11.54 (s, 1H), 10.33 (s, 1H), 7.00–7.90 (m, 7H). | | | | | | 229 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 17 | [4-chloronaphthyloxy-3-chlorophenyl linked to 2,6-difluorobenzoyl acyl urea] | 59.15 | 2.90 | 5.75 | 59.22 | 2.90 | 5.80 | 234–236 |
| 18 | [4-chloronaphthyloxy-3-CF₃-phenyl linked to 2,6-difluorobenzoyl acyl urea] | 57.65 | 2.71 | 5.38 | 57.46 | 2.69 | 5.30 | 215–217 |
| 19 | [4-chloronaphthyloxy-3-chloropyridyl linked to 2,6-difluorobenzoyl acyl urea] | 56.58 | 2.68 | 8.61 | 56.09 | 2.44 | 8.43 | 211.5–212.5 |
| 20 | [4-chloronaphthyloxy-phenyl linked to 2,6-difluorobenzoyl acyl urea] | 63.65 | 3.34 | 6.19 | 63.40 | 3.20 | 6.13 | 214 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 21 | [structure] | 63.69 | 5.34 | 7.96 | 63.71 | 5.31 | 7.83 | 219 |
| 22 | [structure] | 59.89 | 3.22 | 5.59 | 60.89 | 3.38 | 5.27 | 238 |
| 23 | [structure] | 59.42 | 3.99 | 5.54 | 59.56 | 4.08 | 5.48 | 210–212 |
| 24 | [structure] | 64.74 | 5.43 | 5.59 | 64.70 | 5.73 | 5.65 | 192–194 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 25 | (4-chloronaphthyloxy-dichloro-dimethylphenyl)-NH-CS-NH-CO-(2,6-difluorophenyl) | 58.76 | 3.42 | 5.27 | 60.03 | 3.54 | 5.13 | 199–201 |
| 26 | (4-fluorophenyl-CH(CN)-dichlorophenyl)-NH-CO-NH-CO-(2,6-difluorophenyl) | 55.25 | 2.53 | 8.79 | 55.19 | 2.51 | 8.58 | 216–218 |
| 27 | (trichloro-difluorophenyl)-NH-CO-NH-CO-(2,6-difluorophenyl) | 44.12 | 1.59 | 7.35 | 44.08 | 1.44 | 7.38 | 228.5–230 |
| 28 | (4-chloro-2-bromophenoxy-chloro-dimethylphenyl)-NH-CO-NH-CO-(2-fluorophenyl) | 50.22 | 3.06 | 5.32 | 50.16 | 3.14 | 5.30 | 168.5–170 |

TABLE 1-continued

Representative Acyl Urea Compounds

| Compound | Structure | Elemental Analysis | | | | | | | Melting Point °C. |
|---|---|---|---|---|---|---|---|---|---|
| | | Calculated | | | Found | | | | |
| | | C | H | N | C | H | N | | |
| 29 | ![structure] | 56.65 | 2.93 | 5.08 | 56.40 | 3.03 | 5.18 | | 202–210 |
| 30 | ![structure] | 57.27 | 2.96 | 5.14 | 56.87 | 3.05 | 4.91 | | 235–238 |
| 31 | ![structure] | \multicolumn{6}{l}{1H-NMR (DMSO-d$_6$): δ10.68 (br s, 1H), 10.05 (br s, 1H), 7.14–8.03 (m, 8H).} | | | | | | 196–197 |
| 32 | ![structure] | 56.81 | 3.57 | 5.52 | 59.21 | 3.85 | 5.09 | | 208–214 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 33 | 4-chlorophenyl sulfonyl naphthyloxy-chlorophenyl-CO-NH-CO-NH-(2-chloro-6-fluorophenyl) | 54.60 | 2.74 | 4.24 | 54.31 | 2.20 | 4.62 | 172–179 |
| 34 | chloro-naphthyloxy-dichlorophenyl-NH-CO-NH-CO-(4-chlorophenyl) | 55.41 | 2.71 | 5.38 | 55.18 | 2.76 | 5.74 | 262 |
| 35 | 4-methylpiperazinyl-chlorophenyl-NH-CO-NH-CO-(2-chloro-6-fluorophenyl) | 53.65 | 4.50 | 13.17 | 52.39 | 4.49 | 12.57 | 183 |
| 36 | 4-chlorophenyl-N(Me)-CO-NH-CO-(2,6-difluorophenyl) | 55.48 | 3.41 | 8.62 | 55.44 | 3.69 | 8.54 | 111–115 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 37 | (4-chloronaphth-1-yloxy)-2,6-dichlorophenyl-NH-CS-NH-CO-cyclohexyl | 56.75 | 4.16 | 5.51 | 56.64 | 4.09 | 5.47 | 183.5–184 |
| 38 | naphthylmethyl-S-C(=N-N=)-C(=S)-NH-CO-(2,6-difluorophenyl) | 55.25 | 3.09 | 12.27 | 55.40 | 3.16 | 12.22 | 204–205 |
| 39 | (5,6,7,8-tetrahydro-4-chloronaphth-1-yloxy)phenyl-NH-CO-NH-CO-(2,6-difluorophenyl) | 63.09 | 4.19 | 6.13 | 63.33 | 4.24 | 6.11 | 180.5–182.5 |
| 40 | (4-chloronaphth-1-yl)-NH-CO-NH-CO-(2,6-difluorophenyl) | 59.92 | 3.07 | 7.76 | 59.91 | 3.22 | 7.62 | 201–210 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 41 | *structure with Cl, Me, Cl, Me, naphthalene, O, CO—NH—CS—NH, cyclopropyl* | 60.13 | 4.38 | 6.09 | 61.01 | 4.55 | 6.03 | 214–215 |
| 42 | *structure with Me, Me, O, naphthalene, CO—NH—CO—NH, 2,6-difluorophenyl* | 69.94 | 4.51 | 6.27 | 68.61 | 4.60 | 6.21 | 223–228 |
| 43 | *structure with Cl, naphthalene, O, Cl, Me, Me, CO—N(Me)—CO—NH, 2-chlorophenyl* | 61.43 | 4.01 | 5.30 | 61.20 | 4.00 | 5.42 | 95 |
| 44 | *anthracene with CO—NH—CO—NH, 2,6-difluorophenyl* | 70.20 | 3.74 | 7.44 | 67.62 | 3.70 | 7.55 | 215–225 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 45 | 2,6-difluorophenyl-CO-NH-CO-NH-(3,5-dichloro-4-(O-SitBuMe₂)phenyl) | 50.52 | 4.66 | 5.89 | 50.47 | 4.71 | 5.69 | 184–186 |
| 46 | 2,6-dichlorophenyl-CO-NH-CO-NH-(5-chloro-2-pyridinyl N-oxide) | 43.30 | 2.23 | 11.65 | 43.29 | 2.28 | 11.46 | 210–212 |
| 47 | 2,6-difluorophenyl-CO-NH-CO-NH-(4-CF₃-phenyl) | 52.33 | 2.63 | 8.13 | 52.35 | 2.66 | 8.00 | 238–240 |
| 48 | 2-bromophenyl-CO-NH-CO-NH-(3,5-dimethyl-4-(4-chloronaphthalen-1-yloxy)-2-chlorophenyl) | 55.93 | 3.43 | 5.01 | 55.70 | 3.63 | 5.02 | 163–166 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 49 | (structure) | 62.17 | 4.47 | 7.76 | 62.10 | 4.22 | 8.00 | 85–97 |
| 50 | (structure) | 49.52 | 2.20 | 13.59 | 49.49 | 2.26 | 13.61 | 237–240 |
| 51 | (structure) | 55.48 | 3.41 | 8.62 | 55.72 | 3.37 | 8.64 | 165–168 |
| 52 | (structure) | 64.21 | 3.83 | 7.60 | 65.20 | 4.43 | 7.54 | 194–197 |
| 53 | (structure) | 47.70 | 3.16 | 4.63 | 48.14 | 3.34 | 4.49 | 184–186 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 54 | 2,6-difluorobenzoyl / 3-chloro-pyridyl-2-oxy-(2,4-dichlorophenyl) | 48.27 | 2.13 | 8.89 | 48.53 | 1.87 | 8.77 | 209–211 |
| 55 | 2-fluoro-6-chlorobenzoyl / 3-chloro-5-methyl-4-(2-bromo-4-chlorophenoxy)phenyl | 50.21 | 3.06 | 5.32 | 50.02 | 3.08 | 5.25 | 161.5–164 |
| 56 | 2-methylbenzoyl / 3-chloro-5-methyl-4-(2-bromo-4-chlorophenoxy)phenyl | 52.89 | 3.66 | 5.36 | 53.71 | 3.94 | 5.36 | 208–211 |
| 57 | 2,6-dimethoxybenzoyl / 3-chloro-5-methyl-4-(2-bromo-4-chlorophenoxy)phenyl | 50.72 | 3.72 | 4.92 | 50.41 | 3.74 | 4.64 | 178–185 |
| 58 | 2,6-dimethylbenzoyl / 3,5-dimethyl-4-(2-bromo-4-chlorophenoxy)phenyl | 53.75 | 3.94 | 5.22 | 55.16 | 4.12 | 5.02 | 250–254 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 59 | 2,6-dichloro-4-(2,4-dichlorophenylamino)phenyl with CO-NH-CO-NH-(2,6-difluorophenyl) | 47.55 | 2.19 | 8.31 | 47.80 | 2.24 | 8.11 | 225-229 |
| 60 | 2,6-dimethyl-4-(2-chloro-4-trifluoromethylphenoxy)-3,5-dimethylphenyl CO-NH-CO-NH-(2,6-difluorophenyl) | 55.88 | 4.10 | 5.43 | 56.65 | 3.66 | 5.41 | 195.5-198 |
| 61 | 2-chloro-4-(4-chlorophenylthio)-3,5-dimethylphenyl CO-NH-CO-NH-(2,6-difluorophenyl) | 54.89 | 3.35 | 5.82 | 54.69 | 3.32 | 7.66 | 148-154 |
| 62 | 3-chloro-4-(2,4-dichlorophenoxy)-2,5-dimethylphenyl CO-NH-CO-NH-(2,4-difluorophenyl) | 51.03 | 2.72 | 5.41 | 51.92 | 2.83 | 5.15 | 214-216 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 63 | 2,5-difluorophenyl-CO-NH-CO-NH-(3-Me, 4-Cl, 5-(2-Br, 4-Cl-phenoxy), 6-Me)-phenyl | 48.55 | 2.77 | 5.14 | 48.56 | 2.61 | 4.92 | 163–166 |
| 64 | 2,6-difluorophenyl-CO-NH-CO-NH-(3-Me, 4-Cl, 5-(2-Br, 6-CO₂Me, 4-Cl-phenoxy))-phenyl | *585.9510 HRMS | | | *585.9567 HRMS | | | 195.5–199.5 |
| 65 | 2,6-difluorophenyl-CO-NH-CO-NH-(3-Me, 4-Cl, 5-(4-(4-Cl-phenylsulfonyl)phenoxy), 6-Me)-phenyl | 55.54 | 3.32 | 4.62 | 56.36 | 3.50 | 4.45 | 207–209 |
| 66 | 2,6-difluorophenyl-CO-NH-CO-NH-(3,5-diCl, 4-(O-(CH₂)₄-O-(4-Cl-naphthyl)))-phenyl | 56.63 | 3.56 | 4.71 | 56.76 | 3.82 | 4.56 | 204.2–206.9 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 67 | 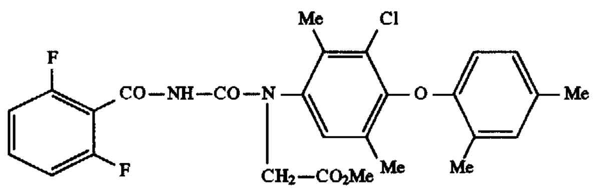 | 61.07 | 4.74 | 5.27 | 60.94 | 4.53 | 5.09 | 186–190 |
| 68 | 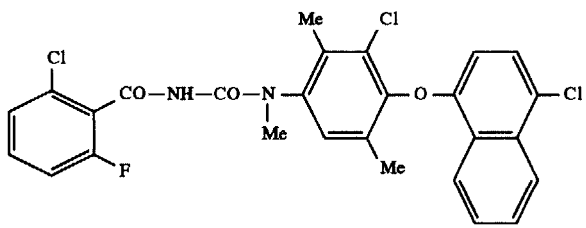 | 59.41 | 3.69 | 5.13 | 60.14 | 4.02 | 5.01 | 220–225 |
| 69 | 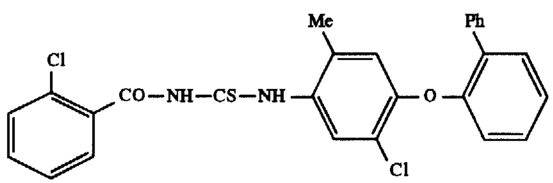 | 63.80 | 3.97 | 5.52 | 64.03 | 4.26 | 5.86 | 146–147 |
| 70 | 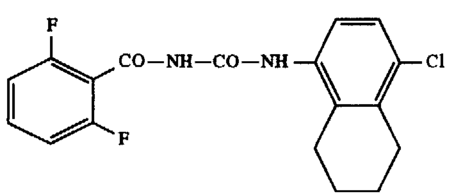 | 59.26 | 4.14 | 7.67 | 59.27 | 4.39 | 7.41 | 207–210 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 71 | (structure) | 63.99 | 5.12 | 6.78 | 63.93 | 5.35 | 6.50 | 179–180 |
| 72 | (structure) | 61.49 | 3.44 | 5.31 | 61.57 | 3.51 | 5.27 | 168.5–169.5 |
| 73 | (structure) | 60.26 | 4.61 | 9.16 | 60.22 | 4.85 | 9.17 | 242–243 |
| 74 | (structure) | 52.03 | 3.96 | 5.51 | 52.24 | 4.03 | 5.49 | 207–208 |
| 75 | (structure) | 52.31 | 2.92 | 6.77 | 52.42 | 3.03 | 6.75 | 188.5–190 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 76 | [structure: pyrrole-N-Me with CO-NH-CO-NH linked to trimethyl-chloro-phenyl ether of dimethylphenyl] | 64.85 | 5.68 | 9.86 | 64.09 | 5.65 | 9.90 | 227-229 |
| 77 | [structure: 2,6-difluorophenyl-CO-N(CH₂-S-(CH₂)₃-Me)-CO-NH linked to dimethyl-chloro-phenyl ether of chloro-methylphenyl] | 57.83 | 4.85 | 4.81 | 58.02 | 4.90 | 4.77 | 145-147 |
| 78 | [structure: 3-bromothiophene-CO-NH-CO-NH linked to dichlorophenyl ether of chloronaphthyl] | 46.30 | 2.11 | 4.90 | 47.34 | 2.18 | 5.01 | 204-205 |
| 79 | [structure: 2-chlorophenyl-CO-N=C(NMe₂)-NH-(4-chlorophenyl)] | 57.15 | 4.49 | 12.49 | 57.06 | 4.49 | 12.36 | 140.5-142.5 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 80 | 2,6-difluorophenyl-CO—NH—CO—NH-(3,5-dichloro-4-(O—CH₂—C≡CH)phenyl) | 51.14 | 2.52 | 7.01 | 50.31 | 2.55 | 6.51 | 188–198 |
| 81 | 2,6-difluorophenyl-CO—NH—CO—NH-(4-(O—CH(Me)-1-naphthyl)phenyl) | 69.94 | 4.51 | 6.27 | 69.58 | 4.31 | 6.40 | 212.5–216 |
| 82 | 2,6-difluorophenyl-CO—NH—CO—NH-(isoxazolyl-Me) | 46.81 | 2.85 | 19.85 | 46.98 | 3.17 | 19.57 | 151–154 |
| 83 | 2,6-difluorophenyl-CO—NH—CO—NH—CH(Me)-(2,4-dichlorophenyl) | 51.49 | 3.24 | 7.50 | 51.67 | 3.23 | 7.49 | 181–183 |
| 84 | 2,6-difluorophenyl-CO—NH—CO—NH—CH(4-chlorophenyl)(4-chlorophenyl) | 57.94 | 3.24 | 6.43 | 58.25 | 3.33 | 6.41 | 196.5–199 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 85 | 2,6-difluorobenzoyl urea with 3-chloro-2,6-dimethyl-4-(6-bromonaphthalen-2-yloxy)phenyl | 55.78 | 3.24 | 5.00 | 55.80 | 3.12 | 5.03 | 208.5–210 |
| 86 | 2,6-difluorobenzoyl urea with α-cyano-4-chlorobenzyl | 54.94 | 2.88 | 12.01 | 55.08 | 2.88 | 12.26 | 220–223 |
| 87 | 2,6-difluorobenzoyl thiourea with 3-chloro-2,6-dimethyl-4-(2-bromo-4-chlorophenoxy)phenyl | 47.16 | 2.69 | 5.00 | 47.98 | 2.81 | 4.51 | 170.5–174 |
| 88 | 2,6-difluorobenzoyl urea with 3,5-dichloro-4-(2-chloro-4-nitrophenoxy)phenyl | 46.49 | 1.95 | 8.13 | 46.56 | 1.99 | 8.13 | 230.5–232.5 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 89 | 2,6-difluorophenyl-CO-NH-CO-NH-[Me,Cl-substituted phenyl]-O-[Me-substituted phenyl with CH(Me)Me and OMe] | 62.08 | 5.01 | 5.57 | 62.00 | 5.14 | 5.50 | 185–186 |
| 90 | 2,6-difluorophenyl-CO-NH-CO-NH-[Et,Et-substituted phenyl]-O-[2,4-Cl-substituted phenyl] | 58.42 | 4.08 | 5.67 | 58.16 | 4.19 | 5.70 | 157–159 |
| 91 | 2,6-difluorophenyl-CO-NH-CO-NH-[Me,Cl-substituted phenyl]-O-[Me-substituted phenyl with OMe] | 59.94 | 4.15 | 6.07 | 60.71 | 4.12 | 5.97 | 182–186 |
| 92 | 2,6-difluorophenyl-CO-NH-CO-NH-[Me,Cl-substituted phenyl]-O-[Me-substituted phenyl with NMe₂] | 60.82 | 4.67 | 8.86 | 62.66 | 4.71 | 8.12 | 125–130 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 93 | [structure: 2,6-difluorobenzoyl-NH-CO-NH-phenyl(Me,Me)-O-phenyl(Br,Cl)] | 51.83 | 3.16 | 5.49 | 56.82 | 3.60 | 5.96 | 161.5–167 |
| 94 | [structure: 2,6-difluorobenzoyl-NH-CO-NH-phenyl(Me,Cl)-O-phenyl(Br,Cl) with dioxolane CH(O-O)] | 47.86 | 2.84 | 4.65 | 49.73 | 3.43 | 4.40 | 170–173 |
| 95 | [structure: 2,6-difluorobenzoyl-NH-CO-NH-phenyl(Me,Cl)-O-phenyl(Br,Cl) with CH=O] | 47.33 | 2.34 | 5.01 | 47.06 | 2.32 | 4.71 | 213–214.5 |
| 96 | [structure: 2,6-difluorobenzoyl-NH-CO-NH-phenyl(Me,Cl)-O-phenyl(Br,Cl) with CH₂OH] | 47.16 | 2.69 | 5.00 | 47.30 | 2.62 | 5.10 | 177–180 |

TABLE 1-continued

Representative Acyl Urea Compounds

| Compound | Structure | Elemental Analysis | | | | | | Melting Point °C. |
|---|---|---|---|---|---|---|---|---|
| | | Calculated | | | Found | | | |
| | | C | H | N | C | H | N | |
| 97 | 2,6-difluorophenyl-CO-NH-CO-NH-(3-Cl-4-Me-5-(2,4-dichlorophenoxy)-6-CH$_2$OMe-phenyl) | 52.14 | 3.23 | 5.28 | 51.84 | 3.22 | 5.25 | 178–179 |
| 98 | 2,6-difluorophenyl-CO-NH-CO-NH-(3-Cl-4-Me-5-(2,6-dimethylphenoxy)-6-Me-phenyl) | 62.81 | 4.61 | 6.10 | 62.63 | 4.44 | 6.04 | 192–194 |
| 99 | 2,6-difluorophenyl-CO-NH-CO-NH-(3-Cl-4-Me-5-(2-Br-4-Cl-phenoxy)-6-C(=O)O-CH$_2$-CH(Me)$_2$-phenyl) | 49.54 | 3.35 | 4.44 | 49.57 | 3.35 | 4.40 | 175–179 |

*High Resolution Mass Spectroscopy.

EXAMPLE VIII

Systemic Control of Northern Fowl Mite
(*Ornithonyssus sylviarum*)

White Leghorn laying hens housed in commercial egg laying cages were preinfested with northern fowl mites 3 weeks prior to being fed the treated feed. The feed was prepared by dissolving Compound 1 (technical grade) in soybean oil and blending the solution with a standard poultry ration. An untreated blank was prepared by blending soybean oil alone with the ration. Twenty birds received feed treated with 500 ppm of Compound 1 and 20 birds received the soybean oil (control). Birds were maintained on the rations for 5 consecutive weeks. Mite counts on each bird were made at weekly intervals, and the number of mites expressed according to the standard index: 0=no mites, 1=1 to 10 mites, 2=11 to 50 mites, 3=50 to 100 mites, 4=100 to 500 mites, 5=500 to 1,000 mites, 6=1,000 to 10,000 mites, 7>10,000 mites.

Results presented in Table 2 show that mite populations on birds receiving feed treated with Compound 1 declined rapidly with most birds free of mites after 3 weeks of feeding. Untreated birds remained heavily infested throughout the trial. At the end of 5 weeks, mite-infested control birds maintained on untreated feed were switched to feed treated with the title compound. As before, mite-free birds were produced in 3 weeks (Table 3).

TABLE 2

Effect of Compound 1 as a Feed Additive (500 ppm) for Systemic Control of Northern Fowl Mite
Average mite index/bird* at weeks on additive

| Treatment | Pre-treatment | 1 Wk. | 2 Wk. | 3 Wk. | 4 Wk. | 5 Wk. |
|---|---|---|---|---|---|---|
| Compound 1 | 4.20 | 4.15 | 2.15 | 0.65 | 0.10 | 0.0 |
| Untreated | 3.75 | 4.44 | 6.10 | 4.40 | 4.30 | 2.50 |

*Mean value based on 20 birds/treatment.

TABLE 3

Reduction in Mite Population on Previously Untreated Birds** Switched Onto Feed-Additive (500 ppm)
Average mite index/bird* after being switched onto additive

| Treatment | Pretreatment | 1 Wk. | 2 Wk. | 3 Wk. |
|---|---|---|---|---|
| Compound 1 | 2.50 | 1.20 | 0.1 | 0.9 |

*Mean value based on 20 birds/treatment.
**Untreated control birds from Table 2.

When the experiment was repeated using Compound 1 at a lower feed additive concentration (50 ppm), a similar result occurred (Table 4). Treated feed for this trial was prepared by mixing dry formulated wettable powder directly with the feed. The dry formulated wettable powder was prepared by uniformly mixing the following ingredients (percentages are all by weight):

| | |
|---|---|
| Compound 1 | 30% |
| Aluminum silicate (Englehard ASP-172) | 54 |
| ICI MX 2026 (a nonionic/ionic surfactant blend, ICI Americas, Inc.) | 8 |
| Talc clay | 5 |
| Ethylene oxide condensate of hydrophobic bases (Tergitol NP) | 2 |
| Dioctyl sodium sulfosuccinate (Aerosol OTB) | 1 |

This mixture was then finely pulverized and remixed by mechanical or air-attrition grinding to obtain the desired wettable powder.

TABLE 4

Effect of Compound 1 as a Feed Additive (50 ppm) for Systemic Control of Northern Fowl Mite
Average mite index/bird* at weeks on additive

| Treatment | Pretreatment | 1 Wk. | 2 Wk. | 3 Wk. | 4 Wk. |
|---|---|---|---|---|---|
| Compound 1 | 3.00 | 1.50 | 0.08 | 0.0 | 0.0 |
| Untreated | 2.83 | 2.00 | 2.33 | 2.58 | 2.5 |

*Mean value based on 12 birds/treatment.

EXAMPLE IX

Systemic Control of Northern Fowl Mite
(*Ornithonyssus sylviarum*)

The experiment described in Example VIII was conducted using Compound 2 in concentrations of 50 ppm and 5 ppm. Treated feed for this trial was prepared by mixing dry formulated wettable powder of Compound 2 directly with the feed. The dry formulated wettable powder was prepared by uniformly mixing the following ingredients (percentages are all by weight):

| | |
|---|---|
| Compound 2 | 26.5% |
| Kaolin clay | 61.2 |
| Alkylaryl sulfonate (Nacconol 90F) | 4.0 |
| Silica clay (Zeolex 7) | 4.0 |
| Dioctyl sodium sulfosuccinate (Aerosol OTB) | 2.0 |
| Sodium naphthalene formaldehyde condensate (Morwet D425) | 2.0 |
| Citric acid | 0.3 |

This mixture was then finely pulverized and remixed by mechanical or air-attrition grinding to obtain the desired wettable powder.

Similar results as occurred in Example VIII were observed (Table 5) using the same mite index as in Example VIII. After 4 weeks the birds receiving Compound 2 in their feed were virtually free of mites even at 5 ppm of Compound 2. Untreated birds remained heavily infested with mites throughout the test period.

TABLE 5

Effect of Compound 2 as a Feed Additive for Systemic Control of Northern Fowl Mite
Average mite index/bird* at weeks on additive

| Treatment | (ppm) | Pretrt. | 1 wk | 2 wk | 3 wk | 4 wk |
|---|---|---|---|---|---|---|
| Compound 2 | 50 | 5.0 | 4.8 | 1.1 | 0.0 | 0.0 |

TABLE 5-continued

Effect of Compound 2 as a Feed Additive for
Systemic Control of Northern Fowl Mite
Average mite index/bird* at weeks on additive

| Treatment | (ppm) | Pretrt. | 1 wk | 2 wk | 3 wk | 4 wk |
|---|---|---|---|---|---|---|
| Compound 2 | 5 | 5.1 | 4.7 | 3.4 | 1.1 | 0.6 |
| UNTREATED | — | 4.1 | 4.4 | 4.3 | 3.4 | 4.4 |

*Mean value based on twelve birds/treatment.

EXAMPLE X

Systemic Control of Northern Fowl Mite on Chickens

White Leghorn pullets (20 weeks old at beginning of this experiment) of the Hy-Line strain were preinfested with northern fowl mites 3 weeks prior to being fed the treated feed. The infested birds were housed two per standard commercial cage with two cages per treatment (four birds) and the untreated controls. Each group of birds was provided with the corresponding treated feed continuously during the 4 weeks of each test. The feed was prepared by suspending one of the compounds (technical grade) identified in Tables 6 and 7 below in ethanol and then spraying the solution onto a standard poultry ration to provide 200 ppm of active ingredient (by weight). An untreated blank was prepared by blending ethanol alone with the ration. Mite counts on each bird were made at weekly intervals, and the number of mites expressed according to the standard index described hereinabove. The results are set for in Tables 6 and 7 below.

TABLE 6

Systemic Control of Northern
Fowl Mite on Chickens
Average mite index/bird* at weeks on additive

| Feed Additive | Pretreatment | 1 wk | 2 wk | 3 wk | 4 wk |
|---|---|---|---|---|---|
| Compound 5 | 5.0 | 2.2 | 0.0 | 0.0 | 0.0 |
| Compound 6 | 5.0 | 6.2 | 6.0 | 4.8 | 1.0 |
| Compound 7 | 4.0 | 2.8 | 1.5 | 0.0 | 0.0 |
| Compound 8 | 4.2 | 6.0 | 0.8 | 0.0 | 0.0 |
| Compound 9 | 4.8 | 6.0 | 4.0 | 1.5 | 0.0 |
| Compound 10 | 4.8 | 6.2 | 6.5 | 6.0 | 3.2 |
| Compound 11 | 3.8 | 3.0 | 0.8 | 0.0 | 0.0 |
| Compound 17** | 3.3 | 3.3 | — | 3.5 | 2.8 |
| Compound 20** | 3.5 | 3.7 | — | 2.2 | 1.5 |
| Compound 21 | 5.8 | 6.2 | 4.5 | 2.2 | 0.2 |
| Untreated Control #1 | 4.8 | 6.0 | 6.5 | 6.5 | 6.3 |
| Untreated Control #2 | 4.3 | 5.5 | 6.3 | 6.8 | 7.0 |

*Mean value based on four birds/treatment.
**Administered at concentration of 250 ppm.

TABLE 7

Systemic Control of Northern
Fowl Mite on Chickens
Average mite index/bird* at weeks on additive

| Feed Additive | Pretreatment | 1 wk | 2 wk | 3 wk | 4 wk |
|---|---|---|---|---|---|
| Compound 4 | 7.0 | 7.0 | 4.2 | 0.0 | 0.0 |
| Compound 12 | 7.0 | 7.0 | 4.5 | 0.0 | 0.0 |
| Compound 13 | 7.0 | 7.0 | 6.5 | 0.2 | 0.0 |
| Compound 19 | 7.0 | 7.0 | 5.8 | 6.0 | 6.5 |

TABLE 7-continued

Systemic Control of Northern
Fowl Mite on Chickens
Average mite index/bird* at weeks on additive

| Feed Additive | Pretreatment | 1 wk | 2 wk | 3 wk | 4 wk |
|---|---|---|---|---|---|
| Compound 27 | 7.0 | 7.0 | 7.0 | 6.0 | 5.2 |
| Compound 29 | 7.0 | 6.8 | 3.0 | 0.0 | 0.0 |
| Compound 30 | 7.0 | 7.0 | 6.8 | 5.8 | 5.8 |
| Untreated Control #1 | 7.0 | 7.0 | 7.0 | 7.0 | 6.8 |
| Untreated Control #2 | 6.8 | 6.8 | 6.0 | 5.8 | 5.3 |

*Mean value based on four birds/treatment.

EXAMPLE XI

Pass-through Effects on Pests in Poultry Manure

Concurrent with monitoring feed additive effects of Compounds 1 and 2 on northern fowl mite, manure from the treated and untreated hens of Examples VIII and IX was collected to determine its toxicity to developing larvae of the house fly (*Musca domestica*). House fly eggs used in these tests were from a laboratory colony established from field-caught flies within a year of the test.

Manure collections were made by suspending plastic covered boards below the cages at intervals throughout the feeding studies of Examples VIII and IX. Samples were then placed in plastic cups with screen lids and inoculated with 50 fly eggs per cup. Adult fly emergence was monitored over a period of 10–30 days. Also measured was the residual toxicity of manure after treated birds were returned to untreated feed (flushing effect).

Table 8 presents the results of the treated feed pass-through tests. Manure from birds fed Compound 1 or Compound 2 in their feed was highly toxic to house fly larvae. Few adults emerged from the droppings of the treated birds whereas a substantial percentage of adults emerged from the manure of the untreated birds.

TABLE 8

Effect of Compound 1 and Compound 2
Feed Additive on House Fly Development
in Manure from Treated Birds

| | | Mean number emerging adult flies* (days on additive) | | |
|---|---|---|---|---|
| Treatment | (ppm) | 3 | 6 | 8 |
| Compound 1 | 50 | 0 | 0 | 0 |
| Compound 2 | 50 | 0.5 | 0.8 | 0.5 |
| Compound 2 | 5 | 2.6 | 1.6 | 3.2 |
| UNTREATED | — | 35.9 | 34.8 | 31.0 |

*Fifty house fly eggs initially added/replicate; 10 reps/treatment.

Table 9 presents the results when birds were returned to untreated feed after previously maintained on the feed additive for four weeks. Manure from birds fed rations treated with Compound 1 remained toxic to fly larvae 2–5 days after the birds were returned to untreated feed.

TABLE 9

Residual Effect of Compound 1 Feed Additive (50 ppm) on Fly Development Following Return of Birds to Untreated Feed**

| Treatment | Mean number emerging adult flies* (days following removal of additive) | | | |
|---|---|---|---|---|
| | −1 | 2 | 5 | 8 |
| Compound 1 | 0 | 4.0 | 23.6 | 38.5 |
| CONTROL | 34.1 | 32.0 | 34.2 | 40.5 |

*Fifty housefly eggs added per replicate; 10 reps/treatment.
**Birds previously maintained on the feed additive for four weeks.

EXAMPLE XII

Pass-through Effects on Pests in Poultry Manure

Concurrent with monitoring feed additive effects of the compounds in Example X on northern fowl mite, manure from the treated and untreated chickens of Example X was collected to determine its toxicity to developing larvae of the house fly (*Musca domestica*). House fly eggs used in these tests were from a laboratory colony established from field-caught flies within a year of the test.

Manure collections were made by suspending plastic covered boards below the cages at intervals throughout the feeding studies of Example X. Samples were then placed in plastic cups with screen lids and inoculated with 50 fly eggs per cup. Adult fly emergence was monitored over a period of 10–30 days.

Table 10 presents the results of the treated feed pass-through tests. Manure from birds fed certain compounds identified in Table 10 in their feed was highly toxic to house fly larvae. Few adults emerged from the droppings of the treated birds whereas a substantial percentage of adults emerged from the manure of the untreated birds.

TABLE 10

Effects of Certain Compounds Used as Feed Additives on House Fly Development in Manure from Treated Birds

| Feed Additive | Percent Inhibition of Adult Fly Emergence Relative to Untreated Control* |
|---|---|
| Compound 3 | 99.7 |
| Compound 4 | 100.0 |
| Compound 5 | 65.3 |
| Compound 6 | 73.1 |
| Compound 7 | 73.8 |
| Compound 8 | 77.8 |
| Compound 9 | 99.4 |
| Compound 10 | 100.0 |
| Compound 11 | 100.0 |
| Compound 12 | 100.0 |
| Compound 13 | 100.0 |
| Compound 16 | 100 |
| Compound 18 | 20.6 |
| Compound 19 | 65.9 |
| Compound 21 | 90.7 |
| Compound 22 | 34.4 |
| Compound 23 | 87.1 |
| Compound 24 | 92.4 |
| Compound 25 | 31.5 |
| Compound 26 | 75.1 |
| Compound 27 | 100 |
| Compound 28 | 98.0 |
| Compound 29 | 87.1 |
| Compound 30 | 12.3 |

*Based on two weekly manure collections; 6 replicates per treatment, fifty house fly eggs added per replicate

EXAMPLE XIII

Systemic Control of Poultry Lice (*Menacanthus stramineus*)

White leghorn laying hens housed in commercial egg laying cages were preinfested with lice by adding approximately 50 lice in all stages of development to each bird 3 weeks prior to testing. There were 8 birds each (2 per cage. 4 cages) for the treatment and for the control.

The treated feed was prepared by mixing 1.135g of Compound 2 (technical grade) with 1 lb. of standard 16% protein laying mash. The 1 lb. of treated feed was then mixed with 99 lbs of laying mash to give a final concentration of Compound 2 in the feed equal to 25 ppm. The control birds were fed the standard laying mash minus Compound 2. The feed, treated or untreated, was provided continuously during the 5 weeks of the test.

Lice populations on each bird were estimated by a standard procedure pretreatment and at weekly intervals after the birds were receiving the treated feed. The lice populations per bird were estimated by recording the total number of lice (nymphs and adults) observed upon parting the feathers in 5 locations (vent area, left thigh, right thigh, left side of breast, right side of breast). Thus, the index in Table 11 is the "no. of lice per 5 feather parts per bird".

As shown in Table 11, the lice population on the birds fed Compound 2 at 25 ppm rapidly declined. The lice population was extremely low after 2 weeks of feeding. and nearly eliminated after 3 weeks of feeding. No lice could be found on any birds after 4 and 5 weeks of feeding. Also, no clusters of lice eggs appeared on the feathers.

Concurrently, there was a gradual increase in the lice population on the untreated control birds. On these birds the lice population increased 3–4 fold during the 5 weeks of the test. Also, there were many lice egg masses on the feathers of these birds.

Lice on chickens are normally very difficult to control but when provided in as little as 25 ppm in the feed of the birds, Compound 2 completely controlled infestations of chicken lice in about 3 weeks.

TABLE 11

Effect of Compound 2 as a Feed Additive at 25 ppm (technical sprayed on 1 lb. feed aliquot) on Populations of Chicken Lice (*Menacanthus stramineus*)

| Treatment | Total No. Lice Per 5 feather Parts Per Bird | | | | | | | | |
|---|---|---|---|---|---|---|---|---|---|
| | 1 | 2 | 3 | 4 | 5 | 6 | 7 | 8 | Mean |
| *Pretreatment* | | | | | | | | | |
| Compound 2 | 47 | 20 | 22 | 74 | 14 | 31 | 21 | 52 | 35.1 |
| Untreated | 17 | 48 | 64 | 87 | 13 | 11 | 20 | 87 | 43.4 |
| *1 wk. Posttreatment* | | | | | | | | | |
| Compound 2 | 41 | 34 | 10 | 56 | 7 | 16 | 29 | 31 | 28.0 |
| Untreated | 115 | 130 | 100 | 140 | 66 | 10 | 210 | 55 | 103.2 |
| *2 wk. Posttreatment* | | | | | | | | | |
| Compound 2 | 9 | 2 | 0 | 15 | 1 | 0 | 1 | 1 | 3.6 |
| Untreated | 165 | 200 | 135 | 110 | 13 | 45 | 85 | 145 | 112.2 |
| *3 wk. Posttreatment* | | | | | | | | | |
| Compound 2 | 2 | 0 | 0 | 0 | 0 | 0 | 0 | 0 | 0.2 |
| Untreated | 160 | 135 | 200 | 190 | 37 | 85 | 85 | 210 | 137.7 |
| *4 wk. Posttreatment* | | | | | | | | | |
| Compound 2 | 0 | 0 | 0 | 0 | 0 | 0 | 0 | 0 | 0 |
| Untreated | 250 | 250 | 155 | 225 | 26 | 110 | 145 | 185 | 168.2 |
| *5 wk. Posttreatment* | | | | | | | | | |
| Compound 2 | 0 | 0 | 0 | 0 | 0 | 0 | 0 | 0 | 0 |
| Untreated | 202 | 185 | 155 | 105 | 45 | 77 | 131 | 185 | 135.6 |

EXAMPLE XIV

Systemic Control of Cattle Lice

Systemic and direct contact action were evaluated against cattle lice on cattle naturally infested with cattle lice. Compound 1 was administered orally in the feed, as a wipe-on (pour-on) salve along the backline and as a full-coverage contact spray. Compounds 2 and 3 were administered orally in feed and as a wipe-on (pour-on) salve.

Cattle on feed supplements received 8.85 mg ai/kg body wt/day by blending dry wettable powder formulations into a premix of ground grain, minerals, and salt. The dry wettable powder formulations for Compound 1 and 2 were prepared as described in Example VIII and IX respectively. The dry wettable powder formulation for Compound 3 was prepared by uniformly mixing the following ingredients (percentages are all by weight):

| Compound 3 | 25.0% |
|---|---|
| Aluminum Silicate (Englehard ASP-172) | 64.5 |
| Synthetic Silica Zeolex 7) | 2.0 |
| Citric Acid | 0.5 |
| Sodium Naphthalene Formaldehyde Condensate (Morwet D425) | 2.0 |
| Alkylaryl Sulfonate (Nacconol 90F) | 4.0 |
| Dioctyl Sodium Sulfosuccinate (Aerosol OTB) | 2.0 |

This mixture was then finely pulverized and remixed by mechanical or air-attrition grinding to obtain the desired wettable powder.

Wipe-on formulations were rubbed into the hair along the backline at a rate of 4 oz. form./animal (35 mg ai/kg) (single application). These formulations were prepared by mixing the following ingredients together in a ball mill to produce the following suspensions (percentages are all by weight):

| I | |
|---|---|
| Compound 1 | 5.0% |
| Carageenen-based flow modifier* | 4.5 |
| Dioctyl sodium sulfosuccinate | 0.4 |
| Cotton seed oil | 90.1 |
| II | |
| Compound 2 | 1.9% |
| Carageenen-based flow modifier* | 2.0 |
| Dioctyl sodium sulfosuccinate | 0.4 |
| Petroleum crop oil | 96.1 |
| III | |
| Compound 3 | 5.0% |
| Carageenen-based flow modifier* | 4.5 |
| Dioctyl sodium sulfosuccinate | 0.4 |
| Cotton Seed Oil | 90.1 |

*A finely divided, solidified vegetable oil derivative which when dispersed by strong shearing action in non-aqueous media, swells to form a thixotropic gel structure.

Compound 1 was additionally applied as a whole-animal contact spray. The spray was prepared by mixing together the following ingredients in a ball mill (all percentages by weight):

| Compound 1 | 15.0% |
|---|---|
| Methyl pyrrolidone | 47.5 |
| Cyclohexanone | 14.9 |
| Altox 3455F (a nonionic/ ionic surfactant blend, ICI Americas, Inc.) | 13.5 |
| Isophorone | 10.0 |
| Butylated Hydroxytoluene | 0.1 |

This mixture is then diluted with water and applied to the animal at 0.03 lb ai/gal (1 gal/animal).

Cattle averaged 430 lb/head. One animal was assigned per treatment with the exception of the control group which contained 2 animals.

Parasite loads were measured before and after treatment at 6 weekly intervals. Separate louse counts were taken from head, shoulder and sides, and tail-rump areas of each animal. The hair was parted using a 5-inch blade along which the number of lice/inch were counted.

Louse counts taken from head, shoulder, side, rump, and tail areas of treated cattle confirm that the compounds moved systemically throughout the animal following ingestion or localized penetration in the area of the pour-on (Table 8). Excellent control of both chewing (*Bovicola bovis*) and sucking (*Linognathus vituli*) lice was achieved within 2 - 3 weeks of initial treatment by all routes of administration. After 4 weeks the cattle administered Compound 1 or 2 were virtually lice-free whereas the untreated cattle remained heavily infested.

TABLE 12

Systemic Control of Cattle Lice[a] with Compounds
1 and 2 Administered as Feed Additives,
Pour-ons and Contact Sprays.

| Treatment[c] | | Pretrt. | Mean number lice per inch[b] (weeks posttreatment) | | | |
|---|---|---|---|---|---|---|
| | | | 1 wk | 2 wk | 3 wk | 4 wk |
| Compound 1 | FA | >35 | 21 | 2 | 0 | 1 |
| Compound 1 | PO | >35 | 7 | 4 | 0 | 0 |
| Compound 1 | SP | >35 | 3 | 0 | 3 | 2 |
| Compound 2 | FA | >35 | >35 | 5 | 0 | 0 |
| Compound 2 | PO | 33 | 18 | 9 | 0 | 0 |
| Compound 3 | FA | >35 | 22 | 5 | 1 | 0 |
| Compound 3 | PO | >35 | 15 | 1 | 0 | 0 |
| Untreated | #1 | >35 | >35 | 33 | >35 | 33 |
| Untreated | #2 | >35 | >35 | 34 | >35 | 28 |

[a]90% *Bovicola bovis*; 10% *Linognathus vituli*
[b]Composite counts from all locations; three 5-inch parts/location
[c]FA = Feed additive; PO = Pour-on; SP = spray.

EXAMPLE XV

Systemic Control of Cattle Nematodes

Systemic action was evaluated against cattle nematodes on cattle naturally infested with internal roundworms. Compound 3 was administered orally in the feed and as a wipe-on (pour-on) salve along the backline.

Cattle on feed supplements received 8.85 mg ai/kg body wt/day by blending dry wettable powder formulations into a premix of ground grain, minerals, and salt. The dry wettable powder formulation for Compound 3 was prepared as described in Example XIV.

Wipe-on formulations were rubbed into the hair along the backline at a rate of 4 oz. form./animal (35 mg ai/kg body wt.) (single application). The wipe-on formulation was prepared as described in Example XIV.

Cattle averaged 430 lb/head. One animal was assigned per treatment with the exception of the control group which contained 2 animals.

Parasite loads were measured before and after treatment at 6 weekly intervals. Intestinal roundworms (primarily strongyles) were monitored using a standard salt fecal floatation technique. Walnut-size portions of manure collected from treated animals were placed in paper cups three-fourths full of a saturated salt solution. After stirring, the resultant slurry was filtered through cheese cloth into a shell vial and a coverslip placed over the top. After 20 minutes, the coverslip was removed, placed on a slide and the total number of worm eggs per slide counted under a light microscope. Nematode egg counts from fecal samples are summarized in Table 13. After 4 weeks, the cattle administered Compound 3 exhibited significantly reduced nematode egg counts in comparison with the untreated cattle.

TABLE 13

Systemic Control of Cattle Nematodes with Compound 3
Administered as Feed Additives and Pour-ons

| Treatment[a] | | Number of Nematode Eggs/Fecal Float (weeks posttreatment) | | | | |
|---|---|---|---|---|---|---|
| | | Pretrt. | 1 wk | 2 wk | 3 wk | 4 wk |
| Compound 3 | FA | 127 | 34 | 6 | 42 | 59 |
| Compound 3 | PO | 93 | 140 | 51 | 26 | 48 |
| Untreated #1 | | >400 | >400 | >400 | >400 | >400 |
| Untreated #2 | | 6 | 10 | 3 | 220 | 201 |

[a]FA = Feed Additive; PO = Pour-on

EXAMPLE XVI

Systemic Control of Sarcoptic Mange in Pigs

Systemic action was evaluated against the mite *Sarcoptes scabiei* in pigs infested with the mite. Compound 2 was administered orally in the feed or as a wipe-on (pour-on) salve.

Pigs on feed supplements received 6 mg ai/kg body wt/day by blending dry wettable powder formulations into the feed. The dry wettable powder formulation for Compound 2 was prepared as described in Example IX.

Wipe-on formulations were rubbed into the back or other area of the animal at a rate of 35 mg ai/kg body wt in a single application. The wipe-on formulations were prepared by mixing the following ingredients together in a ball mill to produce a suspension (percentages are all by weight):

| | |
|---|---|
| Compound 2 | 1.9% |
| Carageenen-based flow modifier* | 2.0 |
| Dioctyl sodium sulfosuccinate | 0.4 |
| Petroleum crop oil | 96.1 |

*A finely divided, solidified vegetable oil derivative which when dispersed by strong shearing action in non-aqueous media, swells to form a thixotropic gel structure.

Parasitic loads were measured before and after treatment at 3 weekly intervals. Excellent systemic control of the mite was achieved within 1 week of initial treatment by both routes of administration (Table 14).

TABLE 14

Systemic Control of Sarcoptic Mange in Pigs with
Compound 2 Administered as Feed Additive and Pour-on

| Treatment | Average # of Live Mites at Wks Posttreatment[a] | | | |
|---|---|---|---|---|
| | Pretreatment | 1 Wk | 2 Wk | 3 Wk |
| Compound 2 FA | 32.8 | 0.5 | 1.5 | 0.0 |
| Compound 2 PO | 62.8 | 1.3 | 4.3 | 0.0 |
| UNTREATED | 25.0 | 16.8 | 22.5 | 11.0 |

[a]Based on one scraping/animal; 4 animals/treatment

129
EXAMPLE XVII

Systemic Control of Rodent Bot Fly

Systemic activity was evaluated against rodent bot fly on Peramiscus mice infested with rodent bot fly (*Cuterebra fontinella*). Larval development of this parasite takes place entirely within the body of the host. All compounds identified in Table 15 were administered orally in the feed as part of the daily ration. There were fifteen (15) mice each for the treatments and for the controls. A separate control was used for each treatment. The treated diet was prepared by pulverizing standard laboratory rat chow pellets. dry-incorporating the technical material and repelletizing. The final feeding concentration of each treatment was 200 ppm. Infestation was accomplished by manually placing 3–4 newly hatched bot fly larvae into the eyes of each mouse. Effectiveness was determined by periodically examining the inguinal region of the mouse for breathing holes cut by the migrating bot fly larvae. Further larval development and emergence from the body of the host was also monitored and recorded. All compounds were offered continuously throughout the experiment as well as during a 5–7 day period prior to infestation with the parasite.

The results are set forth in Table 15 below.

TABLE 15

Systemic Effect on Rodent Bot Fly

| Feed Additive | Percent Mortality* |
|---|---|
| Compound 3 | 100 |
| Compound 4 | 100 |
| Compound 5 | 90 |
| Compound 6 | 97 |
| Compound 7 | 80 |
| Compound 8 | 94 |
| Compound 9 | 63 |
| Compound 10 | 100 |
| Compound 11 | 100 |
| Compound 12 | 100 |
| Compound 13 | 100 |
| Compound 14 | 93 |
| Compound 15 | 100 |
| Compound 18 | 54 |
| Compound 19 | 10 |
| Compound 21 | 48 |
| Compound 22 | 22 |
| Compound 24 | 100 |
| Compound 25 | 10 |
| Compound 27 | 20 |
| Compound 29 | 78 |
| Compound 30 | 38 |

*Based on the number of air holes cut in treated mice in comparison with air holes cut in untreated mice for each treatment.

The results from Table 15 show a systemic effect as indicated by the major reduction in the number of air holes cut in treated mice.

130
EXAMPLE XVIII

Systemic Effect Against Flea Reproduction on Cats

Systemic activity was evaluated against fleas on cats infested with fleas (Ctenocephalides spp.). Treated feed for this experiment was prepared by mixing dry formulated wettable powder of the compounds identified in Tables 16 and 17 directly with the feed. The dry formulated wettable powder was prepared by uniformly mixing the following ingredients (percentages are all by weight):

| | |
|---|---|
| Compound 2 or 8 | 25.0% |
| Aluminum Silicate (Englehard ASP-172) | 64.5 |
| Synthetic Silica (Zeolex 7) | 2.0 |
| Citric Acid | 0.5 |
| Sodium Naphthalene Formaldehyde Condensate (Morwet D425) | 2.0 |
| Alkylaryl Sulfonate (Nacconol 90F) | 4.0 |
| Dioctyl Sodium Sulfosuccinate (Aerosol OTB) | 2.0 |

This mixture was then finely pulverized and remixed by mechanical or air-attrition grinding to obtain the desired wettable powder. The wettable powders were mixed into a portion of the daily ration (10 mg ai/kg body wt/day) and administered orally to the cats which were housed individually in galvanized wire cages. Flea infestations were established and maintained by infesting the test animals with adult fleas prior to and at weekly intervals after beginning treatment. Fifty, 7 to 14 day old, unfed adult fleas were placed along the dorsal midline of each cat. Three cats were used per treatment, each cat receiving the feed supplements for one month.

Treatment effects on adult fleas were assessed by combing them from the cats each week. To determine possible reproductive effects on the subsequent generation, eggs from these adults were collected on plywood boards suspended beneath the cage of each cat. Flea eggs were swept from the boards with a soft nylon brush, transferred to larval rearing media and held for development through one generation.

TABLE 16

| | Systemic Effect on Progeny of Adult Fleas Feeding on Cats | | | | | | | | | |
|---|---|---|---|---|---|---|---|---|---|---|
| Feed Additive | Total Number of Fleas Produced* (days on treatment) | | | | | | | | | |
| | −1 | 0 | 1 | 2 | 3 | 5 | 7 | 14 | 21 | 28 |
| Compound 2 | 328 | 335 | 3 | 0 | 0 | 0 | 0 | 0 | 0 | 0 |
| Compound 8 | 257 | 237 | 13 | 20 | 3 | 0 | 0 | 9 | 1 | 0 |
| Untreated | 404 | 235 | 191 | 343 | 407 | 275 | 266 | 129 | 262 | 59 |

*Counts based on 3 egg sweepings/treatment/sample (one sweeping per cat).

TABLE 17

Systemic Effect on Progeny of Adult Fleas Feeding on Cats Which Received Single Oral Dose**

| Feed Additive | Total Number of Fleas Produced* (days posttreatment) | | | | |
|---|---|---|---|---|---|
|  | 0 | 1 | 2 | 3 | 5 |
| Compound 2 | 544 | 29 | 1 | 11 | 32 |
| Untreated | 169 | 248 | 321 | 484 | 314 |

*Counts based on 3 eggs sweepings/treatment/sample (one sweeping per cat).
**Single dose of 10 mg ai/kg body wt. of Compound 2 administered on day zero.

Although adult fleas feeding on the treated animals were not directly affected, the results from Tables 16 and 17 show that development of their offspring was significantly inhibited. This effect was particularly dramatic after 2 days of receiving the feed supplement, i.e., no $F_1$ progeny developed through to the adult stage. Examination of the larval rearing containers indicated that the lethal effect on the progeny of exposed adults occurred very early in development; probably within the egg or shortly after hatch. The results from Table 17 indicate that a single 10 mg/kg body weight dose administered orally to cats also provides excellent control (>98% nonviable eggs) for 3 days. Roughly 90% nonviable eggs were still being produced 5 days after treatment.

EXAMPLE XIX

Systemic Control of Black Blowfly in Mice

Male Swiss-Webster mice weighing 30 grams or more were administered the compounds identified in Table 18 via gavage. Four mice were used for each treatment and the controls. The compounds were formulated by mixing technical grade samples of each compound identified in Table 18 with Tween 20° to a 4% concentration. The mice were dosed at a concentration of 400 mg active ingredient/kg body weight. The mice used in the positive control (bromophos) were dosed at a concentration of 100 mg active ingredient/kg body weight. The mice were euthanized 16 hours following treatment and the rear legs excised. Twenty first instar black blowfly larvae [*Phormia regina* (Meigen)] were introduced to the excised mouse leg muscle tissue. Blowfly development was monitored (i) 48 hours after introduction to muscle tissue (as a measure of direct larval mortality), (ii) 5 days after introduction to muscle tissue (as a measure of inhibition of pupal development), and (iii) through to adult emergence of the control group (approximately 10–12 days after pupation). Percent mortality was determined by observation of the number of surviving larvae, pupae or adults in treated mice in comparison with the untreated controls.

TABLE 18

Systemic Control of Black Blowfly in Mice

| Treatment | Percent Mortality | | |
|---|---|---|---|
|  | Larvae | Pupae | Adults |
| Compound 2 | * | 100 | — |
| Compound 3 | 100 | — | — |
| Compound 4 | * | 100 | — |
| Compound 5 | * | 100 | — |
| Compound 6 | 100 | — | — |
| Compound 8 | 100 | — | — |

TABLE 18-continued

Systemic Control of Black Blowfly in Mice

| Treatment | Percent Mortality | | |
|---|---|---|---|
|  | Larvae | Pupae | Adults |
| Compound 9 | 100 | — | — |
| Compound 10 | 100 | — | — |
| Compound 11 | 100 | — | — |
| Compound 12 | 100 | — | — |
| Compound 13 | * | 100 | — |
| Compound 14 | 100 | — | — |
| Compound 15 | 100 | — | — |
| Compound 16 | * | 100 | — |
| Compound 21 | * | 100 | — |
| Compound 23 | 100 | — | — |
| Compound 24 | 100 | — | — |
| Compound 26 | 100 | — | — |
| Compound 27 | 100 | — | — |
| Compound 28 | 100 | — | — |
| Compound 31 | 100 | — | — |
| Compound 32 | * | 100 | — |
| Compound 33 | 0 | 0 | 15 |
| Compound 34 | 0 | 0 | 10 |
| Compound 35 | 0 | 0 | 45 |
| Compound 36 | 100 | — | — |
| Compound 37 | 0 | 0 | 35 |
| Compound 38 | 0 | 0 | 15 |
| Compound 39 | * | 100 | — |
| Compound 40 | 0 | 0 | 5 |
| Compound 41 | * | * | 80 |
| Compound 42 | 0 | * | 80 |
| Compound 43 | * | 100 | — |
| Compound 44 | * | 100 | — |
| Compound 45 | 0 | * | 40 |
| Compound 46 | * | 100 | — |
| Compound 47 | 100 | — | — |
| Compound 48 | 0 | * | 55 |
| Compound 49 | 0 | — | 45 |
| Compound 50 | 0 | * | 65 |
| Compound 51 | 0 | * | 20 |
| Compound 52 | 0 | * | 70 |
| Compound 53 | * | 100 | — |
| Compound 54 | 100 | — | — |
| Compound 55 | * | 100 | — |
| Compound 56 | * | 100 | — |
| Compound 57 | * | 100 | — |
| Compound 58 | 0 | * | 35 |
| Compound 59 | * | 100 | — |
| Compound 60 | * | 100 | — |
| Compound 61 | 100 | — | — |
| Compound 62 | 100 | — | — |
| Compound 63 | 0 | * | 90 |
| Compound 64 | 0 | * | 65 |
| Compound 65 | 0 | 0 | 65 |
| Compound 66 | 0 | 0 | 5 |
| Compound 67 | 0 | 0 | 20 |
| Compound 68 | 0 | 0 | 15 |
| Compound 69 | 0 | 0 | 25 |
| Compound 70 | 0 | 0 | 15 |
| Compound 71 | * | * | 70 |
| Compound 72 | 0 | 0 | 70 |
| Compound 73 | 0 | 0 | 15 |
| Compound 74 | 0 | 0 | 35 |
| Compound 75 | * | 100 | — |
| Compound 76 | 0 | 0 | 20 |
| Compound 77 | 0 | * | 65 |
| Compound 78 | * | * | 50 |
| Compound 79 | 0 | 0 | 75 |
| Compound 80 | 0 | 0 | 5 |
| Compound 81 | * | 100 | — |
| Compound 82 | 0 | 0 | 15 |
| Compound 83 | 0 | 0 | 30 |
| Compound 84 | 0 | 0 | 40 |
| Compound 85 | * | * | 100 |
| Compound 86 | 0 | 0 | 10 |
| Compound 87 | * | * | 100 |
| Compound 88 | * | 100 | — |
| Compound 89 | * | 100 | — |

TABLE 18-continued

Systemic Control of Black Blowfly in Mice

| Treatment | Percent Mortality | | |
|---|---|---|---|
| | Larvae | Pupae | Adults |
| Compound 90 | * | 100 | — |
| Compound 91 | 100 | — | — |
| Compound 92 | 100 | — | — |
| Compound 93 | * | 100 | — |
| Compound 94 | * | 100 | — |
| Compound 95 | * | * | 70 |
| Compound 96 | 100 | — | — |
| Compound 97 | * | 100 | — |
| Compound 98 | * | * | 95 |
| Compound 99 | 0 | 0 | 5 |
| Untreated Control Tween 20 ® | 0 | 0 | 0 |
| Untreated Control | 0 | 0 | 0 |
| Bromophos | 100 | — | — |

*Indicates some control of larvae, however, not complete control.

EXAMPLE XX

Systemic Control of Endoparasitic Cesstodes in Mice

Male Swiss-Webster mice weighing 30 grams or more which had been orally infected with tapeworm (*Hymenolepsis nana*) eggs were treated with the compounds identified in Table 19. Four mice were used for each treated host and control and two mice were used for each nontreated host. Yomesan was used as a positive control. The compounds were administered as feed additive rations for 18 consecutive days at a concentration of 1000 ppm. Feed additive rations were prepared by uniformly blending technical grade samples of each compound identified in Table 19 with pulverized mice chow (Purina brand Rat Chow #5001). Mice were necropsied after 18 days on the ration and tapeworm development was monitored. Tapeworm eggs found in the gut of the treated mice were introduced into a second group of noninfected and nontreated mice (2 mice per treatment). These mice were each necropsied 14 days after infestation, and again tapeworm development was monitored. Percent mortality was determined by observation of tapeworm development in the gut of mice in comparison with the untreated control. and is based on the number of infected mice in comparison with the number of uninfected mice. The results in Table 19 demonstrate a reduction in tapeworm offspring in the nontreated host. The results in Table 19 also demonstrate direct adult tapeworm developmental inhibition by compounds 56 and 64.

TABLE 19

Systemic Control of Endoparasitic Cesstodes (Tapeworm) in Mice

| | Percent Mortality | |
|---|---|---|
| TREATMENT | TREATED HOST | NON-TREATED HOST |
| Compound 5 | 0 | 50 |
| Compound 10 | 0 | 50 |
| Compound 13 | 0 | 50 |
| Compound 15 | 0 | 50 |
| Compound 56 | 50 | — |
| Compound 64 | 75* | — |

TABLE 19-continued

Systemic Control of Endoparasitic Cesstodes (Tapeworm) in Mice

| | Percent Mortality | |
|---|---|---|
| TREATMENT | TREATED HOST | NON-TREATED HOST |
| Untreated Control | 0 | 0 |
| Yomesan | 100 | — |

*Growth size stunted about 75 percent for surviving adult tapeworms (25 percent).

EXAMPLE XXI

Systemic Control of Cat Flea $F_1$ Progeny

Adult cats weighing 4.5–6.0 kg were treated with feed additive rations of the compounds identified in Table 20 for seven consecutive days. One cat was used for each treatment and the control. Feed additive rations were prepared by uniformly blending technical grade samples of each compound identified in Table 20 with the daily food to attain a 10 mg active ingredient/kg body weight dosage. Twenty-four hours after the cat hosts were given the feed additive ration for day number 1. each cat was infested with 100 adult cat fleas [*Ctenocephalides felis* (Bouché)] as 50:50 mixture of males and females. Cat flea ova were collected from pans suspended beneath each cage at various intervals (day numbers 4. 5 and 6). while the host cat was on the 7 day ration. Collected ova were cultured to determine hatch and development to adult stadium. The results are given in Table 20. Percent mortality was determined by observation of the collected ova which developed in comparison with the untreated control.

TABLE 20

Systemic Control of Cat Flea $F_1$ Progeny

| FEED ADDITIVE | PERCENT MORTALITY OF CAT FLEA $F_1$ PROGENY |
|---|---|
| Compound 2 | 100 |
| Compound 5 | 100 |
| Compound 14 | 28 |
| Compound 15 | 99.5 |
| Compound 26 | 60.5 |
| Compound 28 | 100 |
| Untreated Control | 0 |

EXAMPLE XXII

Systemic Control of EndoParasitic Nematodes in Mice

Male Swiss-Webster mice weighing 30 grams or more which had been orally infected with threadworm (*Nematospiroides dubius*) third stage larvae were treated with compounds identified in Table 21. Four mice were used for each treated host and the controls. Thiabendazole was used as a positive control. The compounds were administered as feed additive rations for 18 consecutive days at a concentration of 1000 ppm. Feed additive rations were prepared by uniformly blending technical grade samples of each compound identified in Table 21 with pulverized mice chow (Purina brand Rat Chow #5001). Mice were necropsied after 18 days on the ration and threadworm development was monitored. On days 12, 13 and 14 of the 18 day period, fecal pellets were collected from the mice and any threadworm eggs which had passed into the feces were cultured to third stage larvae ($F_1$). Culturing occurred in a clean petri dish at ambient temperature. Development from egg to third stage larvae occurred in about 7–10 days. The results in Table 21 are based on four mice per treatment for the treated host and the controls. Percent mortality for the treated host was determined by observation of threadworm in the necropsied mice after 18 days. Percent mortality for $F_1$ larvae was determined by observation of third stage larvae in the fecal material in comparison with the untreated control for days 12, 13 and 14 of the 18 day period. The results in Table 21 demonstrate a reduction in $F_1$ threadworm larvae in comparison with the untreated control for certain of the compounds. The results in Table 21 also demonstrate stunted threadworm size development in the treated host after 18 days.

TABLE 21

Systemic Control of Endoparasitic Nematodes (Threadworm) in Mice

| TREATMENT | Percent Mortality | |
|---|---|---|
| | TREATED HOST (18 days) | LARVAE DEVELOPMENT ($F_1$) |
| Compound 2 | 0* | 100 |
| Compound 4 | 0* | 100 |
| Compound 5 | 0* | 0 |
| Compound 9 | 0* | 0 |
| Compound 11 | 0* | 33 |
| Compound 13 | 0* | 0 |
| Compound 15 | 0* | 33 |
| Compound 21 | 0* | 0 |
| Compound 24 | 0* | 0 |
| Compound 37 | 0** | 0 |
| Compound 54 | 0* | 33 |
| Untreated Control | 0 | 0 |
| Thiabendazole | 100 | — |

*Growth size stunted about 75 percent.
**Growth size stunted about 25 percent.

It will be understood that the parasite species employed in the above tests are merely representative of a wide variety of endoparasites and ectoparasites that can be controlled by the acyl urea compounds represented by the generic formula 1.

Although the invention has been illustrated by the preceeding examples, it is not to be construed as being limited thereby; but rather, the invention encompasses the generic area as hereinbefore disclosed. Various modifications and embodiments can be made without departing from the spirit and scope thereof.

We claim:

1. A method systematically of controlling parasites of warm-blooded animals which comprises orally or percutaneously administering to the animal a parasiticidally effective amount of a compound having the formula:

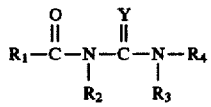

wherein $R_1$ and $R_4$ are independently a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

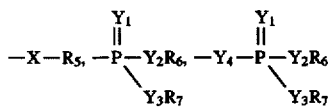

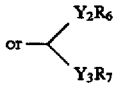

wherein $R_5$ is a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which are permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylaminoi, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluorooalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

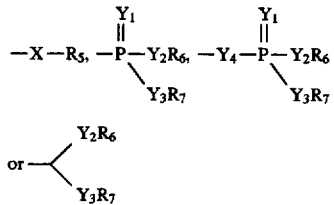

$Y_1$ and $Y_4$ are independently oxygen or sulfur, $Y_2$ and $Y_3$ are independently oxygen, sulfur, amino or a covalent bond, $R_6$ and $R_7$ are independently hydrogen or substituted or unsubstituted alkyl, polyhaloalkyl, phenyl or benzyl in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, progargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, akenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

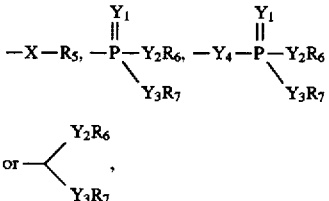

X is a covalent single bond or double bond, a substituted or unsubstituted heteroatom or substituted carbon atom, or a substituted or unsubstituted, branched or straight chain containing two or more carbon atoms or heteroatoms in any combination in which the permissible substituents are the same or different and are one or more hydrogen, ahlogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxyfulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonly and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

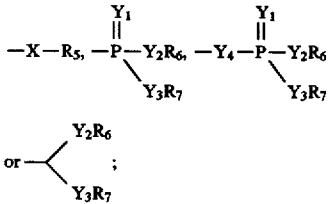

or $R_4$ is hydrogen;

Y is oxygen or sulfur; and $R_2$ and $R_3$ are independently hydrogen, alkyl, substituted alkyl in which the permissible substituents are the same or different and are one or more halogen, alkoxy, alkylthio, or cyano; cycloalkyl, cycloalkenyl, substituted benzyl in which the permissible substituents are the same or different and are one or more halogen, hydroxy, nitro, cyano, alkyl, polyhaloalkyl, alkoxy or polyhaloalkoxy; hydroxy, alkoxy, polyhaloalkoxy, alkylthio, polyhaloalkylthio, acyl, alkoxycarbonyl, alkoxythiocarbonyl, alkylsulfonyl, substituted phenylsulfonyl in which the permissible substituents are the same or different and are one or more halogen, nitro, cyano or polyhaloalkyl; substituted phenylthio in which the permissible substituents are the same or different and are one or more halogen, alkyl, nitro, cyano, polyhaloalkyl, or substituted or unsubstituted alkoxycarbonyl, alkenoxycarbonyl, alkynoxycarbonyl, cycloalkoxycarbonyl, phenoxycarbonyl, hydroxycarbonyl or the alkali metal salt or ammonium salt thereof, alkyl, alkoxy, alkylthio, cycloalkyl, cycloalkyloxy, cycloalkylthio, alkenyl, alkenylthio, alkanoyl, alkylsulfonyl, alkynyl, phenyl, phenoxy, phenylthio or amino; N-(alkylcarbonyl)-N- alkylaminothio, alkoxycarbonylthio, trialkylsilyl, dialkylarylsilyl, thiarylsilyl,

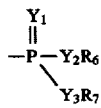

or $R_2$ and $R_3$ are independently

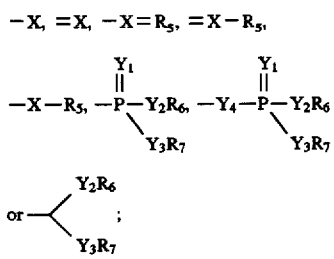

or $R_2$ and $R_3$ may be linked together to form a substituted or unsubstituted, heterocyclic ring system which may be saturated or unsaturated and in which the permissible substitutents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluorialkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

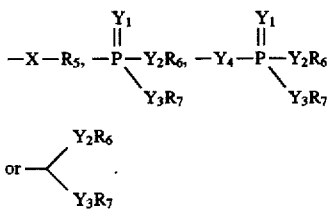

used together with one or more growth promoters.

2. The method of claim 1 wherein $R_1$, $R_4$ and $R_5$ are independently a substituted or unsubstituted, carbocyclic or heterocyclic ring system selected from a monocyclic aromatic or nonaromatic ring system having the formula

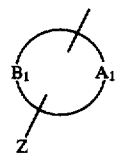

a bicyclic aromatic or nonaromatic ring system having the formula selected from

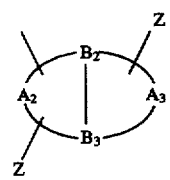

and

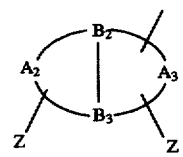

a polycyclic aromatic or nonaromatic ring system having the formula selected from

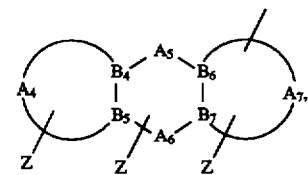

and a bridged ring system which may be saturated or unsaturated having the formula selected from wherein:

$A_1$ represents a ring-forming chain of atoms which together with $B_1$ forms a carbocyclic or heterocyclic ring system containing from 0 to 3 double bonds or from 0 to 2 triple bonds;

$B_1$ represents a saturated or unsaturated carbon atom;

$A_2$ and $A_3$ independently represent a ring-forming chain of atoms which together with $B_2$ and $B_3$ form a carbocyclic or heterocyclic ring system;

$B_2$ and $B_3$ are independently a saturated or unsaturated carbon atom or a saturated nitrogen atom:

$A_4$, $A_5$, $A_6$ and $A_7$ independently represent a ring-forming chain of atoms which together with $B_4$, $B_5$, $B_6$ and $B_7$ form a carbocyclic or heterocyclic ring system;

$B_4$, $B_5$, $B_6$ and $B_7$ are independently a saturated or unsaturated carbon atom or a saturated nitrogen atom:

$A_8$, $A_9$ and $A_{10}$ independently represent a ring-forming chain of atoms which together with $B_8$, $B_9$, $B_{10}$ and $B_{11}$ form a carbocyclic or heterocyclic ring system;

$B_8$, $B_9$ and $B_{10}$ are independently a saturated or unsaturated carbon atom or a saturated nitrogen atom:

$B_{11}$ represents a saturated or unsaturated carbon atom, nitrogen atom or phosphorous atom:

$A_{11}$, $A_{12}$ and $A_{13}$ independently represent a ring-forming chain of atoms which together with $B_{12}$ and $B_{13}$ form a carbocyclic or heterocyclic ring system:

$B_{12}$ and $B_{13}$ are independently a saturated carbon atom or a nitrogen atom: and Z is the same or different and is one or more of hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, $$-X, =X, -X=R_5, =X-R_5,$$

$$-X-R_5, -P\overset{\overset{Y_1}{\|}}{\underset{Y_3R_7}{\diagdown}}Y_2R_6, -Y_4-P\overset{\overset{Y_1}{\|}}{\underset{Y_3R_7}{\diagdown}}Y_2R_6$$

$$\text{or} -\overset{Y_2R_6}{\underset{Y_3R_7}{\diagdown}}$$

wherein $R_5$, $R_6$, $R_7$, $Y_1$, $Y_2$, $Y_3$, $Y_4$ and X are as defined in claim 1.

3. The method of controlling parasites of warm-blooded animals of claim 1 which comprises orally or percutaneously administering to the animal a parasiticidally effective amount of a compound having the formula:

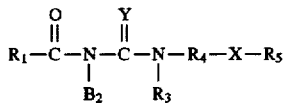

wherein:

R$_1$ and R$_4$ are independently a substituted or unsubstituted, carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

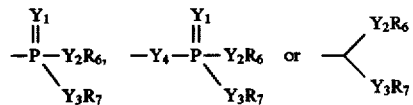

wherein Y$_1$ and Y$_4$ are independently oxygen or sulfur, Y$_2$ and Y$_3$ independently are oxygen, sulfur, amino or a convalent bond, and R$_6$ and R$_7$ are independently hydrogen or substituted or unsubstituted alkyl, polyhaloalkyl, phenyl or benzyl in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethy, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, $$-X, =X, -X=R_5, =X-R_5,$$

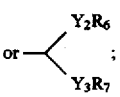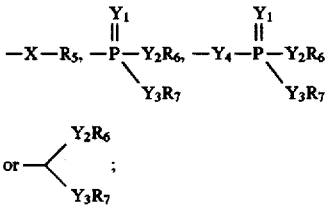

R$_5$ is a substituted or unsubstituted carbocyclic or heterocyclic ring system selected from a monocyclic aromatic or nonaromatic ring system, a bicyclic aromatic or nonaromatic ring system, a polycyclic aromatic or nonaromatic ring system, and a bridged ring system which may be saturated or unsaturated in which the permissible substituents are the same or different and are one or more-hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyimilLomethyl, hydrazonomethyl, unsubstituted or substituted arylhydrazonomethyl, a hydroxy group condensed with a mono-, di- or polysaccharide,

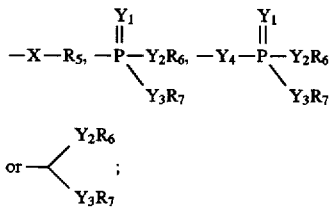

X is a covalent single bond or double bond, a substituted or unsubstituted heteroatom or substituted carbon atom, or a substituted or unsubstituted, branched or straight chain containing two or more carbon atoms or heteroatoms in any combination in which the permissible substituents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, aikynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

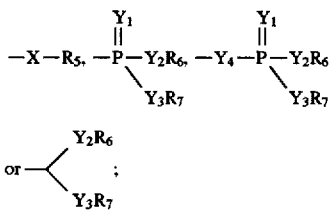

Y is oxygen or sulfur; and $R_2$ and $R_3$ are independently hydrogen, alkyl, substituted alkyl in which the permissible substituents are the same or different and are one or more halogen, alkoxy, alkylthio, or cyano; cycloalkyl, cycloalkenyl, substituted benzyl in which the permissible substituents are the same or different and are one or more halogen, hydroxy, nitro, cyano, alkyl, polyhaloalkyl, alkoxy or polyhaloalkoxy; hydroxy, alkoxy, polyhaloalkoxy, alkylthio, polyhaloalkylthio, acyl, alkoxycarbonyl, alkoxythiocarbonyl, alkylsulfonyl, substituted phenylsulfonyl in which the permissible substituents are the same or different and are one or more halogen, nitro, cyano or polyhaloalkyl; substituted phenylthio in which the permissible substituents are the same or different and are one or more halogen, alkyl, nitro, cyano, polyhaloalkyl, or substituted or unsubstituted alkoxycarbonyl, alkenoxycarbonyl, alkynoxycarbonyl, cycloalkoxycarbonyl, phenoxycarbonyl, hydroxycarbonyl or the alkali metal salt or ammonium salt thereof, alkyl, alkoxy, alkylthso, cycloalkyl, cycloalkyloxy, cycloalkylthio, alkenyl, alkenylthio, alkanoyl, alkylsulfonyl, alkynyl, phenyl, phenoxy, phenylthio or amino; N-(alkylcarbonyl)-N- alkylaminothio, alkoxycarbonylthio, trialkylsilyl, dialkylarylsilyl, thiarylsilyl,

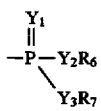

or $R_2$ and $R_3$ may be linked together to form a substituted or unsubstituted, heterocyclic ring system which may be saturated or unsaturated and in which the permissible substitutents are the same or different and are one or more hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide,

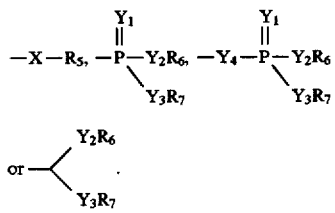

4. The method of claim 3 wherein $R_1$, $R_4$ and $R_5$ are independently a substituted or unsubstituted, carbocyclic or heterocyclic ring system selected from a monocyclic aromatic or nonaromatic ring system having the formula

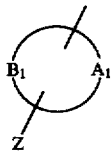

a bicyclic aromatic or nonaromatic ring system having the formula selected from

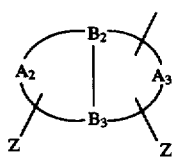

and

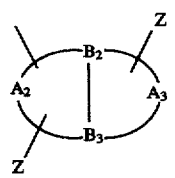

a polycyclic aromatic or nonaromatic ring system having the formula selected from

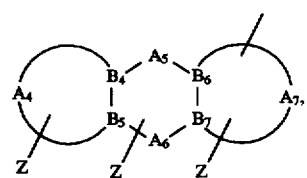

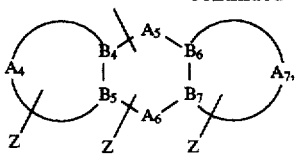

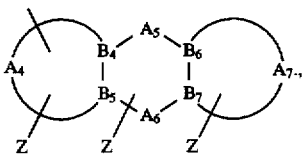

and

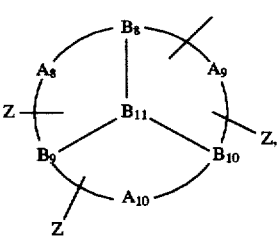

and a bridged ring system which may be saturated or unsaturated having the formula selected from

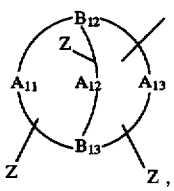

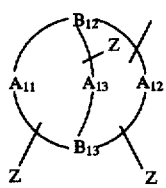

and

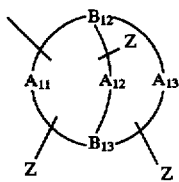

wherein:

$A_1$ represents a ring-forming chain of atoms which together with $B_1$ forms a carbocyclic or heterocyclic ring system containing from 0 to 3 double bonds or from 0 to 2 triple bonds;

$B_1$ represents a saturated or unsaturated carbon atom;

$A_2$ and $A_3$ independently represent a ring-forming chain of atoms which together with $B_2$ and $B_3$ form a carbocyclic or heterocyclic ring system;

$B_2$ and $B_3$ are independently a saturated or unsaturated carbon atom or a saturated nitrogen atom;

$A_4$, $A_5$, $A_6$ and $A_7$ independently represent a ring-forming chain of atoms which together with $B_4$, $B_5$, $B_6$ and $B_7$ form a carbocyclic or heterocyclic ring system;

$B_4$, $B_5$, $B_6$ and $B7$ are independently a saturated or unsaturated carbon atom or a saturated nitrogen atom;

$A_8$, $A_9$ and $A_{10}$ independently represent a ring-forming chain of atoms which together with $B_8$, $B_9$, $B_{10}$ and $B_{11}$ form a carbocyclic or heterocyclic ring system:

$B_8$, $B_9$ and $B_{10}$ are independently a saturated or unsaturated carbon atom or a saturated nitrogen atom;

$B_{11}$ represents a saturated or unsaturated carbon atom, nitrogen atom or phosphorous atom;

$A_{11}$, $A_{12}$ and $A_{13}$ independently represent a ring-forming chain of atoms which together with $B_{12}$ and $B_{13}$ form a carbocyclic or heterocyclic ring system;

$B_{12}$ and $B_{13}$ are independently a saturated carbon atom or a nitrogen atom; and Z is the same or different and is one or more of hydrogen, halogen, alkylcarbonyl, alkylcarbonylalkyl, alkoxycarbonylalkyl, alkoxycarbonylalkylthio, polyhaloalkenylthio, thiocyano, propargylthio, hydroxyimino, alkoxyimino, trialkylsilyloxy, aryldialkylsilyloxy, triarylsilyloxy, foramidino, alkylsulfamido, dialkylsulfamido, alkoxysulfonyl, polyhaloalkoxysulfonyl, hydroxy, amino, aminocarbonyl, alkylaminocarbonyl, dialkylaminocarbonyl, aminothiocarbonyl, alkylaminothiocarbonyl, dialkylaminothiocarbonyl, nitro, cyano, hydroxycarbonyl and derivative salts, formamido, alkyl, alkoxy, polyhaloalkyl, polyhaloalkoxy, alkoxycarbonyl, substituted amino in which the permissible substituents are the same or different and are one or two propargyl, alkoxyalkyl, alkylthioalkyl, alkyl, alkenyl, haloalkenyl or polyhaloalkenyl; alkylthio, polyhaloalkylthio, alkylsulfinyl, polyhaloalkylsulfinyl, alkylsulfonyl, polyhaloalkylsulfonyl, alkylsulfonylamino, alkylcarbonylamino, polyhaloalkylsulfonylamino, polyhaloalkylcarbonylamino, trialkylsilyl, aryldialkylsilyl, triarylsilyl, sulfonic acid and derivative salts, phosphonic acid and derivative salts, alkoxycarbonylamino, alkylaminocarbonyloxy, dialkylaminocarbonyloxy, alkenyl, polyhaloalkenyl, alkenyloxy, alkynyl, alkynyloxy, polyhaloalkenyloxy, polyhaloalkynyl, polyhaloalkynyloxy, polyfluoroalkanol, cyanoalkylamino, semicarbazonomethyl, alkoxycarbonylhydrazonomethyl, alkoxyiminomethyl, unsubstituted or substituted aryloxyiminomethyl, hydrazonomethyl, unsubstituted or substituted arylhydrazonomethyl, a hydroxy group condensed with a mono-, di- or polysaccharide, $-X$, $=X$, $-X=R_5$, $=X-R_5$,

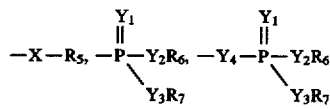

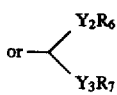

wherein $R_5$, $R_6$, $R_7$, $Y_1$, $Y_2$, $Y_3$, $Y_4$ and X are as defined in claim 3.

5. The method of controlling parasites of warm-blooded animals of claim 1 which comprises orally or percutaneously administering to the animal a parasiticidally effective amount of a compound having the formula:

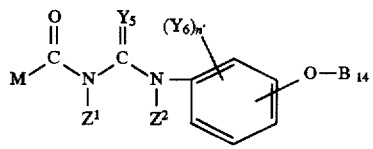

wherein:

M represents a monocyclic aromatic ring system or a monocyclic heterocyclic ring system containing up to 2 nitrogen atoms, and wherein the rings can contain up to 2 nitrogen atoms, and wherein the ring can contain up to four $X_1$ substituents wherein each $X_1$ individually can be halogen, nitro, cyano, or alkyl, polyhaloalkyl, alkoxy or polyhaloalkoxy of from 1 to 3 carbon atoms;

$Z_1$ and $Z_2$ individually are hydrogen or alkyl of from 1 to 8 carbon atoms, or alkyl of from 1 to 8 carbon atoms which is substituted with at least one of halogen, hydroxyl or alkoxy;

$Y_5$ is oxygen or sulfur;

$Y_6$ individually represents halogen, or alkyl, polyhaloalkyl, alkoxy or polyhaloalkoxy of from 1 to 3 carbon atoms, and n' has a value of from 0 to 4; and $B_{14}$ is a bicyclic fused ring system which is attached to the oxygen through a carbocyclic ring and wherein (a) at least one ring is a six-membered, unsaturated carbocyclic ring which can contain up to two $R_{16}$ and $R_{17}$ substituents wherein $R_{16}$ and $R_{17}$ can be halogen, nitro, cyano, amino, formamido, formamidino, phenylsulfenyl, phenylsulfinyl, phenylsulfonyl, phenylsulfamido wherein the phenyl ring optionally may be substituted with one or more halogen, nitro, or alkyl, polyhaloalkyl, alkoxy or polyhaloalkoxy of from 1 to 3 carbon atoms, or $R_{16}$ and $R_{17}$ individually are alkyl, alkoxy, polyhaloalkyl, polyhaloalkoxy, alkenyloxy, polyhaloalkenyloxy, alkynyloxy, polyhaloalkynyloxy, alkylsulfenyl, polyhaloalkylsulfenyl, alkylsulfinyl, polyhaloalkylsulfinyl, alkylsulfonyl, polyhaloalkylsulfonyl, mono- or di-alkylsulfamido, mono or di-alkylamino, alkylcarbonylamino, alkoxycarbonylamino, mono- or di-alkylamino- carbonyloxy of up to 6 carbon atoms, and (b) the second ring, hereinafter also referred to as $A_{14}$, when it is not a five or six-membered carbocyclic can be a five or six-membered saturated or unsaturated heterocyclic ring which can contain in any combination carbonyl or one or two oxygen or sulfur, and up to two $R_{18}$ and $R_{19}$ substituents attached to unsaturated ring carbon atoms wherein $R_{18}$ and $R_{19}$ individually can be halogen, nitro, cyano, or alkyl, polyhaloalkyl, alkoxy, polyhaloalkoxy, alkylthio, arylthio, alkylsulfinyl, arylsulfinyl, alkylsulfonyl, arylsulfonyl, alkylsulfamido, arylsulfamido, alkoxycarbonylamino, or alkylcarbonylamino of from 1 to 6 carbon atoms, or can contain up to two $R_{20}$ and $R_{21}$ substituents attached to saturated carbon atoms of the chain wherein $R_{20}$ and $R_{21}$ individually can be alkyl or polyhaloalkyl of from 1 to 6 carbon atoms.

6. The method of controlling parasites of warm-blooded animals of claim 1 which comprises orally or percutaneously administering to the animal a parasiticidally effective amount of a compound having the formula:

151

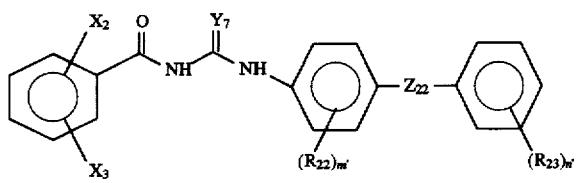

wherein:

$X_2$ and $X_3$ are independently hydrogen, halogen, alkyl, haloalkyl, polyhaloalkyl, alkoxy or polyhaloalkoxy;

$Z_{22}$ represents oxygen, azo, sulfur or sulfone;

$Y_7$ represents oxygen or sulfur;

m' and n' are independently 0–4;

$R_{22}$ independently represents hydrogen, halogen, alkyl, haloalkyl, polyhaloalkyl, alkoxy, nitro, hydroxycarbonyl, alkoxycarbonyl, alkenyl or alkynyl; and $R_{23}$ independently represents hydrogen, halogen, alkyl, polyhaloalkyl, polyhaloalkoxy, alkylsulfonyl, alkoxy, alkylthio, dialkylamino, cyano, nitro, haloalkylthio, trifluoromethylsulphonyl, alkenyl, alkynyl, thiocyano, alkylsulfinyl, arylthio, $CO_2R_{24}$, $CONHR_{24}$, arylsulfinyl or arylsulfonyl, wherein $R_{24}$ represents alkyl.

7. The method of controlling parasites of warm-blooded animals of claim 1 which comprises orally or percutaneously administering to the animal a parasiticidally effective amount of a compound having the formula:

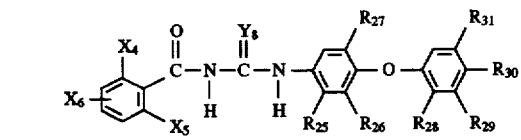

wherein:

$x_4$ represents halogen;

$x_5$ represents hydrogen or halogen;

$x_6$ represents halogen or hydrogen;

$Y_8$ is oxygen or sulfur;

$R_{25}$, $R_{26}$ and $R_{27}$ are independently alkyl, halogen, polyhaloalkyl, alkoxy, nitro, cyano, alkylthio, polyhaloalkylthio or arylthio; and $R_{28}$, $R_{29}$, $R_{30}$ and $R_{31}$ are independently hydrogen, alkyl, halogen, nitro, alkoxy, polyhaloalkyl, polyhaloalkoxy, dialkylamino, or aryl.

8. The method of controlling parasites of warm-blooded animals of claim 1 which comprises orally or percutaneously administering to the animal a parasiticidally effective amount of a compound having the formula:

152

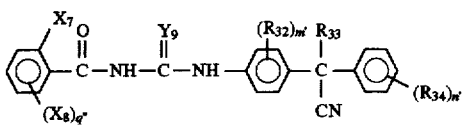

wherein:

$X_7$ and $X_8$ are independently hydrogen, halogen, alkyl, haloalkyl, polyhaloalkyl, alkoxy, haloalkoxy or polyhaloalkoxy:

$R_{32}$ is independently hydrogen, halogen, alkyl, haloalkyl, polyhaloalkyl, alkoxy, haloalkoxy, polyhaloalkoxy, carboxylic acid, carboxylic acid salt or carboxylic acid ester:

$R_{33}$ is hydrogen, alkyl, polyhaloalkyl, hydroxy, amino or dialkylamino:

$R_{34}$ is independently hydrogen, halogen, alkyl, haloalkyl, polyhaloalkyl, alkoxy, haloalkoxy, polyhaloalkoxy, carboxylic acid, carboxylic acid salt, carboxylic acid ester, cyano or nitro;

m' and n' independently have a value of from 0 to 4, and q" has a value from 1 to 4: and $Y_9$ is oxygen or sulfur.

9. The method of controlling parasites of warm-blooded animals of claim 1 which comprises orally or percutaneously administering to the animal a parasiticidally effective amount of a compound having the formula:

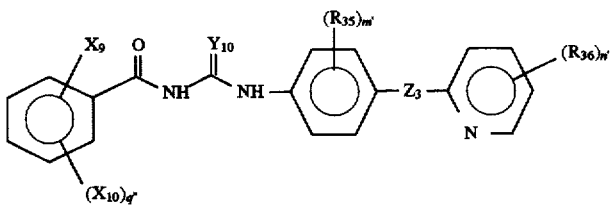

wherein:

$Y_{10}$ represents oxygen or sulfur;

$z_3$ represents oxygen, sulfur, sulfinyl, sulfonyl, unsubstituted or substituted amino in which the permissible substituents are one or more hydrogen, alkyl, acyl or alkenyl;

$X_9$ and $X_{10}$ are independently hydrogen, halogen, trifluoromethyl, alkyl or polyhaloalkyl;

$R_{35}$ independently represents hydrogen, halogen, trifluoromethyl, alkyl, alkoxy, nitro, alkenyl, hydroxycarbonyl, alkoxycarbonyl or alkylcarbonyl;

$R_{36}$ independently represents hydrogen, halogen, alkyl, cyano, nitro, trifluoromethyl, alkoxy, polyhaloalkyl, polyhaloalkoxy, dialkylamino, alkylthio, polyhaloalkylthio, arylthio, or alkenyl optionally substituted with halogen: and m' and n' independently have a value of from 0 to 4, and q" has a value of from 1 to 4.

10. The method of controlling parasites of warm-blooded animals of claim 1 which comprise orally or percutaneously administering to the animal a parasiticidally effective amount of a compound having the formula:

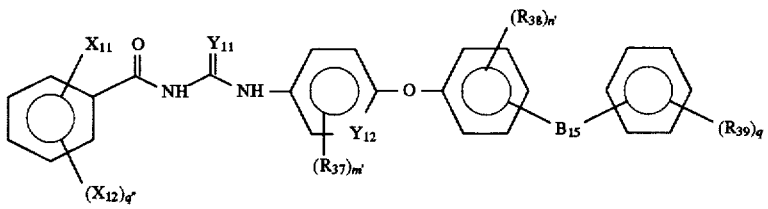

wherein:

- $Y_{11}$ is oxygen or sulfur;
- $Y_{12}$ is $CR_{37}$ or nitrogen;
- $B_{15}$ is oxygen, sulfur, sulfinyl, sulfonyl, oxysulfonyl, sulfonyloxy or carbonyl;
- $X_{11}$ and $X_{12}$ are independently hydrogen, halogen, alkoxy, alkyl, trifluoromethyl or polyhaloalkyl;
- $R_{37}$ and $R_{38}$ are independently alkoxy, hydrogen, halogen, alkyl, trifluoromethyl, polyhaloalkyl or polyhaloalkoxy;
- $R_{39}$ is independently hydrogen, halogen, alkyl, trifluoromethyl, polyhaloalkyl, polyhaloalkoxy, alkoxy, alkylthio, alkylsulfinyl, alkylsulfonyl, or $R_{39}$ can optionally be a substituted arylthio, a substituted arylsulfonyl, or a substituted arylsulfinyl, wherein said optional substituents are alkyl or halogen, and m', n' and q independently have a value of from 0 to 4, and q" has a value of from 1 to 4.

11. The method of controlling parasites of warm-blooded animals of claim 1 which comprises orally or percutaneously administering to the animal a parasiticidally effective amount of a compound having the formula:

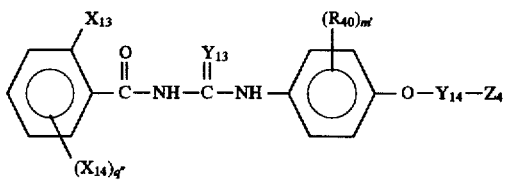

- $X_{13}$ is halogen, alkyl, alkoxy, polyhaloalkyl, polyhaloalkoxy or nitro;
- $X_{14}$ is hydrogen, halogen, alkyl, alkoxy, polyhaloalkyl, polyhaloalkoxy or nitro;
- $R_{40}$ is hydrogen, halogen, alkyl, alkoxy, polyhaloalkyl, polyhaloalkoxy, nitro, cyano, carboxylic acid, carboxylic acid salt or carboxylic acid ester;
- m' has a value of from 0 to 4;
- $Y_{13}$ is oxygen or sulfur;
- $Y_{14}$ is alkylene or a covalent bond;
- $Z_4$ is substituted or unsubstituted

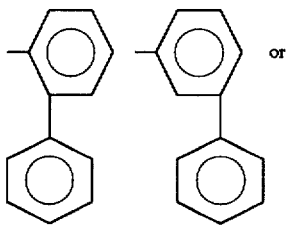

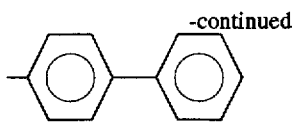

wherein the permissible substituents are one or more halo, alkyl, alkoxy, polyhaloalkyl, polyhaloalkoxy, nitro, cyano, carboxylic acid, carboxylic acid salt or carboxylic acid ester substituents which may be the same or different; and q" has a value of from 1 to 4.

12. The method of controlling parasites of warm-blooded animals of claim 1 which comprises orally or percutaneously administering to the animal a parasiticidally effective amount of a compound having the formula:

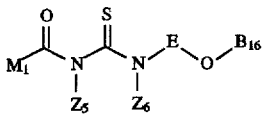

wherein:

- $M_1$ represents a monocyclic aromatic ring system or a monocyclic heterocyclic ring system containing up to two nitrogen atoms and $M_1$ can contain up to four $X_{15}$ substituents, each of which individually can be halogen, nitro, cyano or alkyl, polyhaloalkyl, alkoxy, or polyhaloalkoxy of from one to three carbon atoms;
- $Z_5$ and $Z_6$ individually are hydrogen, alkyl or alkyl which may be substituted by at least one halogen, hydroxy or alkoxy;
- E is a six membered carbocyclic aromatic ring or a five or six membered heterocyclic ring containing up to two oxygen, sulfur or nitrogen atoms or a combination thereof, and wherein this ring may contain up to four $Y_{15}$ substituents wherein each $Y_{15}$ individually can be halogen, cyano or alkyl, polyhaloalkyl, alkoxy, polyhaloalkyoxy, alkylsulfenyl, or polyhaloalkylsulfenyl of from one to six carbon atoms;
- $B_{16}$ is a bicyclic fused ring system which is attached to the oxygen through a carbocyclic ring and wherein (a) at least one ring is six-membered, unsaturated and carbocyclic and which contains the substituents $R_{41}$ and $R_{42}$ (b) the second ring; hereinafter also referred to as a $A_{15}$, when it is not a five or six-membered saturated or unsaturated carbocyclic can be a five or six-membered saturated or unsaturated heterocyclic which can contain in any combination a carbonyl group or one or two oxygen or sulfur atoms and the substituents $R_{43}$ and $R_{44}$ attached to unsaturated ring carbons or the substituents $R_{45}$ and $R_{46}$ attached to saturated ring carbons;
- $R_{41}$ and R42 individually may be hydrogen, halogen, nitro, cyano, amino, formamido, formamidino, phenylsulfenyl, phenylsulfinyl, phenylsulfonyl, phenylsulfamido or phenyloxysulfonyl, wherein the phenyl ring optionally may contain one or more substituents, selected from halogen, nitro, or alkyl, polyhaloalkyl, alkoxy, or polyhaloalkoxy of from one to three carbon atoms, or $R_{41}$ and $R_{42}$ individually may be alkyl, alkoxy, polyhaloalkyl, polyhaloalkoxy, alkenyloxy, polyhaloalkenyloxy, alkynyloxy, polyhaloalkynyloxy, alkylsulfenyl, alkylsulfonyl, polyhaloalkylsulfenyl, alkylsulfinyl, mono- or di-alkylsulfamido, mono- or di-alkylamino, alkylcarbonylamino, alkoxycarbonylamino, mono- or di-alkylaminocarbonyloxy, alkoxysulfonyl, polyhaloalkyloxysulfonyl of up to six carbons in each alkyl chain, morphilinosulfonyl or the group $SO_3Na$;

$R_{43}$ and $R_{44}$ can individually be hydrogen, halogen, nitro, cyano, or alkyl, polyhaloalkyl, alkoxy, polyhaloalkoxy, alkylsulfinyl, alkylsulfenyl, alkylsulfonyl, alkoxycarbonylamino or alkylcarbonylamino of from one to eight carbons: and $R_{45}$ and $R_{46}$ individually can be hydrogen, alkyl or polyhaloalkyl from one to six carbon atoms or phenyl which may be optionally substituted with up to three halogen, cyano, nitro or alkyl, polyhaloalkyl, alkoxy or polyhaloalkoxy of up to three carbon atoms.

13. The method of controlling parasites of warm-blooded animals of claim 1 which comprises orally or percutaneously administering to the animal a parasiticidally effective amount of a compound having the formula:

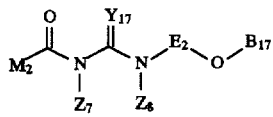

wherein $M_2$ represents a monocyclic aromatic ring system or a monocyclic heterocyclic ring system containing up to four $X_{16}$ substituents, each $X_{16}$ substituent is selected from the group of halogen, nitro, cyano or alkyl, polyhaloalkyl, alkoxy, polyhaloalkoxy, alkylsulfenyl or polyhaloalkylsulfenyl of from one to three carbon atoms;

$Z_7$ and $Z_8$ individually are hydrogen, alkyl, or alkoxy, either or which may be substituted by at least one halogen, hydroxy or alkoxy;

$Y_{17}$ is oxygen or sulfur;

$E_2$ is a five or six member heterocyclic ring containing up to two oxygen, sulfur or nitrogen atoms or a combination thereof, and wherein said ring may contain up to three $Y_{16}$ substitutents, each $Y_{16}$ is selected from the group of halogen, cyano, or alkyl, polyhaloalkyl, alkoxy, polyhaloalkoxy, alkylsulfenyl or polyhaloalkylsulfenyl of from one to three carbon atoms;

$B_{17}$ is a bicyclic fused ring system which is attached to the oxygen through a carbocyclic ring and wherein (a) at least one ring is six-membered, unsaturated and carbocyclic and which contains the substituents $R_{47}$ and $R_{48}$, (b) the second ring, $A_{16}$, when it is not a five or six-membered saturated or unsaturated carbocyclic can be a five or six-membered saturated or unsaturated heterocyclic ring which can contain in any combination carbonyl or one or two oxygen or sulfur atoms and the substituents $R_{49}$ and $R_{50}$ attached to unsaturated ring carbons or the substituents $R_{51}$ and $R_{52}$ attached to the saturated ring carbon atoms, wherein $R_{47}$ and $R_{48}$ are selected from the group of hydrogen, halogen, nitro, cyano, amino, formamido, phenylsulfenyl, phenylsulfinyl, phenylsulfonyl, pheylsulfonate, phenylsulfamido, wherein the phenyl ring optionally may be substituted with one or more halogen, nitro, or alkyl, polyhaloalkyl, alkoxy, or polyhaloalkoxy of from one to three carbon atoms, or $R_{47}$ and $R_{48}$ individually may be alkyl, alkoxy, polyhaloalkyl, polyhaloalkoxy, alkenyloxy, polyhaloalkenyloxy, alkynyloxy, polyhaloalkynyoxy, alkylsulfenyl, polyhaloalkylsulfenyl, alkylsulfinyl, polyhaloalkysulfinyl, alkylsulfonyl, polyhaloalkylsulfonyl, mono- or dialkylsulfamido, mono- or di-alkylaminocarbonyloxy, alkylsulfonate, or polyhaloalkylsulfate of up to six carbon atoms:

$R_{49}$ and $R_{50}$ are selected from the group of hydrogen, halogen, nitro, cyano, or alkyl, polyhaloalkyl, alkoxy, polyhaloalkoxy, alkylthio, arylthio, alkylsulfinyl, arylsulfinyl, alkylsulfonyl, arylsulfonyl, alkylsulfamido, arylsulfamido, alkoxycarbonylamino or alkylcarbonylamino of from one to eight carbon atoms; and $R_{51}$ and $R52$ are selected from the group of alkyl or polyhaloalkyl of from one to six carbon atoms.

14. The method of controlling parasites of warm-blooded animals of claim 1 which comprises orally or percutaneously administering to the animal a parasiticidally effective amount of a compound having the formula:

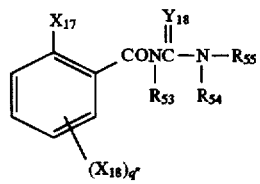

wherein:

q" is a value of from 1 to 4;

$X_{17}$ and $X_{18}$ are independently hydrogen, halogen, trifluoromethyl, alkyl, alkoxy, polyhaloalkyl or polyhaloalkoxy:

$Y_{18}$ is oxygen or sulfur;

$R_{55}$ is a substituted or unsubstituted heterocyclic system selected from

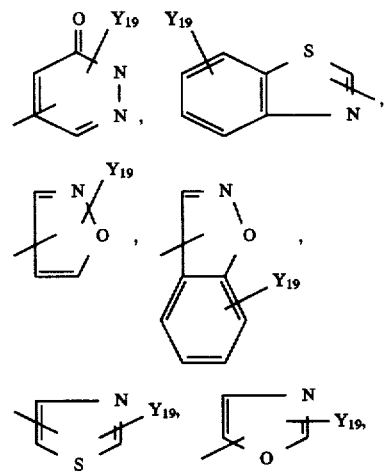

157

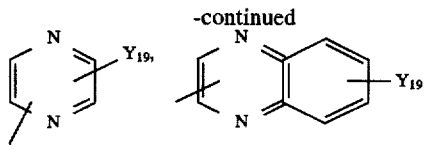

wherein

Y$_{19}$ is the same or different and is one or more hydrogen, halogen, cyano, nitro, alkyl, branched alkyl, polyhaloalkyl, polyhaloalkoxy, alkoxycarbonyl, or an optionally substituted cycloalkyl, phenyle biphenyl, benzylt phenoxy, phenyl thio, phenoxybenzyl, phenoxyphenyl, phenyithiobenzyl, phenylthiophenyl, phenylsulfinylbenzyla phenylsulfinylphenyl, phenylsulfonylbenzyl, phenylsulfonylphenyl, naphthoxy, tetrahydronaphthoxy or naphthyl in which the permissible substituents are the same or different and are one or more halogen, alkoxy, polyhaloalkyl, polyhal[]oalkoxy, alkyl, nitro or cyano; and R$_{53}$ and R$_{54}$ are independently hydrogen, alkyl, acyl, alkoxycarbonyl or, when Y$_{18}$ is oxygen, R$_{53}$ and R$_{54}$ may be linked together to form a ring selected from

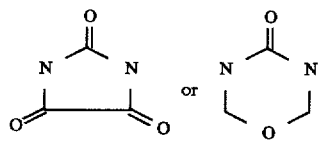

15. The method of controlling parasites of warm-blooded animals of claim 1 which comprises orally or percutaneously administering to the animal a parasiticidally effective amount of a compound having the formula:

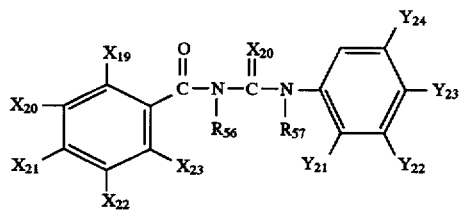

wherein:

x$_{19}$, X$_{20}$, X$_{21}$, X$_{22}$ and X$_{23}$ are independently halogen, hydrogen, alkyl, alkoxy, nitro, cyano or polyhaloalkyl;

Y$_{20}$ is oxygen or sulfur;

Y$_{21}$, Y$_{22}$, Y$_{23}$ and Y$_{24}$ are independently hydrogen, halogen, trialkylsilyl, nitro, cyano, alkyl, alkoxy, polyhaloalkyl, polyhaloalkoxy, alkoxycarbonyl, alkylthio, substituted or unsubstituted cycloalkylalkoxy wherein the permissible substituents are the same or different and are one or more hydrogen, alkyl, aryl, haloaryl, alkylaryl or halogen; alkynyl, alkylcarbonyl, alkoxycarbonylalkyl, alkoxycarbonylalkylthio, polyhaloalkenylthio; a group selected from alkoxy, alkylthio, alkylsulfonyl, alkenyloxy or alkylsulfinyl, each of which may be substituted with one or more halogen atoms which may be the same or different; substituted or unsubstituted cycloalkoxy wherein the permissible substituents are the same or different and are one or more halogen, hydrogen, alkyl or aryl; polyfluoroalkanol, optionally substituted phenyl or —X—R$_5$ wherein X and R$_5$ are as defined in claim 1, or Y$_{21}$, Y$_{22}$, Y$_{23}$ and Y$_{24}$ may form, together with an adjacent group selected from Y$_{21}$, Y$_{22}$, Y$_{23}$ and Y$_{24}$, an alkylenedioxy group which may be substituted with one or more halogen atoms; when Y$_{20}$ is oxygen, R$_{56}$ and R$_{57}$ are independently hydrogen, alkyl, substituted alkyl in which the permissible substituents are the same or different and are one or more halogen, alkoxy, alkylthio or cyano; substituted benzyl in which the permissible substituents are the same or different and are one or more halogen, hydroxy, nitro, cyano, alkyl, polyhaloalkyl, alkoxy or polyhaloalkoxy; hydroxy, alkoxy, polyhaloalkoxy, alkylthio, polyhaloalkylthio, acyl, alkoxycarbonyl, alkylsulfonyl, substituted phenylsulfonyl in which the permissible substituents are the same or different and are one or more halogen, nitro, cyano or alkyl; N-alkylcarbonyl-N-alkylaminothio,

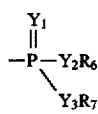

wherein

Y$_1$, Y$_2$, Y$_3$, R$_6$ and R$_7$ are as defined in claim 1; or R$_{56}$ and R$_{57}$ may be linked together to form a heterocycle selected from

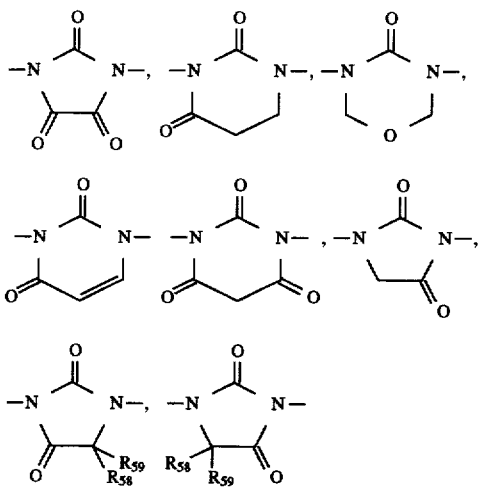

wherein

R$_{58}$ and R$_{59}$ are independently hydrogen, halogen, substituted or unsubstituted alkyl, polyhaloalkyl, phenyl or benzyl; and when Y$_{20}$ is sulfur, R$_{56}$ is hydrogen and R$_{57}$ is hydrogen or alkyl.

16. The method of controlling parasites of warm-blooded animals of claim 1 which comprises orally or percutaneously administering to the animal a parasiticidally effective amount of a compound having the formula:

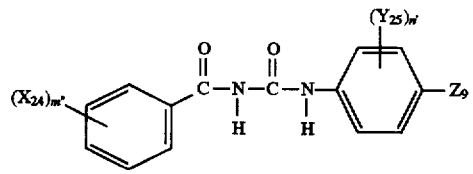

wherein:

X$_{24}$ is halogen, hydrogen, alkyl or alkoxy;

m" is a value of 1 to 5;

$Y_{25}$ is halogen, alkyl or trifluoromethyl;

n' is a value of from 0 to 4;

$Z_9$ is halogen.

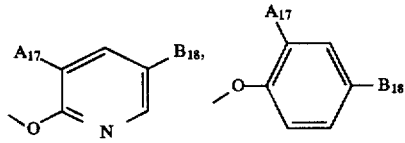

wherein $A_{17}$ and $B_{18}$ are independently hydrogen, halogen, trifluoromethyl, cyano or nitro.

17. The method of controlling parasites of warm-blooded animals of claim 1 which comprises orally or percutaneously administering to the animal a parasiticidally effective amount of a compound having the formula:

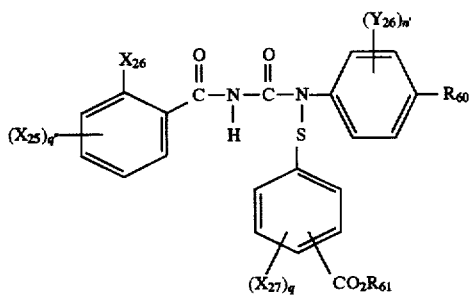

wherein:

$X_{25}$ and $X_{26}$ are independently hydrogen, halogen, alkyl, alkoxy, polyhaloalkyl, nitro or cyano;

q" is a value of from 1 to 4;

$R_{61}$ is substituted or unsubstituted alkyl, alkenyl, alkynyl, cycloalkyl or phenyl; a hydrogen atom or 1 equivalent of an alkali metal or optionally substituted ammonium cation; each $X_{27}$ is independently halogen, cyano, nitro, hydroxycarbonyl or optionally substituted alkyl, alkoxy, alkylthio, cycloalkyl, cycloalkyloxy, cycloalkylthio, alkenyl, alkenylthio, alkanoyl, alkoxycarbonyl, alkylsulphonyl, alkynyl, phenyl, phenoxy, phenylthio or amino;

q is a value of from 0 to 4;

$R_{60}$ is halogen, alkyl, polyhaloalkyl, alkoxy, polyhaloalkoxy, alkenyloxy, polyhaloalkenyloxy, nitro, cyano or —X—$R_5$ wherein X and $R_5$ are as defined in claim 1; each $Y_{26}$ is independently halogen, nitro, cyano, alkyl, or polyhaloalkyl; and n' is a value of from 0 to 4.

18. The method of controlling parasites of warm-blooded animals of claim 1 which comprises orally or percutaneously administering to the animal a parasiticidally effective amount of a compound having the formula:

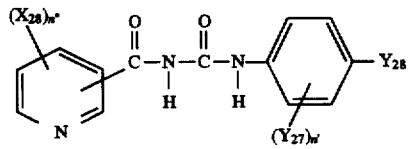

and the acid addition salt thereof, wherein:

$X_{28}$ is independently halogen, hydrogen, alkoxy, alkyl, polyhaloalkoxy, polyhaloalkyl, nitro or cyano;

n" is a value of from 0 to 3, and n' is a value of from 0 to 4; and $Y_{27}$ and $Y_{28}$ are independently hydrogen, halogen, alkoxy, alkyl, polyhaloalkoxy, polyhaloalkyl, nitro, cyano, alkenyl, alkenyloxy, polyhaloalkenyl, or polyhaloalkenyloxy.

19. The method of controlling parasites of warm-blooded animals of claim 1 which comprises orally or percutaneously administering to the animal a parasiticidally effective amount of a compound having the formula:

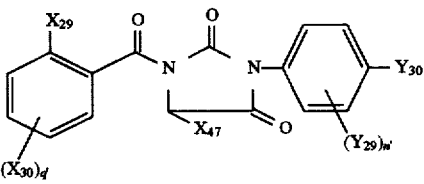

wherein:

$X_{29}$ and $X_{30}$ are independently hydrogen, halogen, alkyl, alkoxy, polyhaloalkyl, nitro, or polyhaloalkoxy;

$X_{47}$ is halogen, hydrogen, hydroxy, alkoxy, or polyhaloalkoxy;

$Y_{30}$ is halogen, alkyl, polyhaloalkyl, alkoxy, polyhaloalkoxy, alkenyloxy, polyhaloalkenyloxy, nitro, cyano, or —X—$R_5$ wherein X and $R_5$ are as defined in claim 1;

$Y_{29}$ is independently halogen, nitro, cyano, alkyl, or polyhaloalkyl; and q" is a value of from 1 to 4 and n' is a value of from 0 to 4.

20. The method of controlling parasites of warm-blooded animals of claim 1 which comprises orally or percutaneously administering to the animal a parasiticidally effective amount of a compound having the formula:

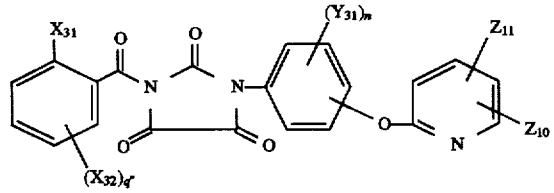

wherein:

$X_{31}$ and $X_{32}$ are independently hydrogen, halogen, alkyl, alkoxy, polyhaloalkyl, nitro or polyhaloalkoxy;

$Y_{31}$ is independently halogen, alkyl, alkoxy, polyhaloalkyl or polyhaloalkoxy;

n is a value of from 0 to 2, and q" is a value of from 1 to 4;

$Z_{11}$ is hydrogen, halogen or alkyl; and $Z_{10}$ is halogen, alkyl optionally substituted with fluorine or chlorine; nitro or cyano; and wherein the pyridyloxy group is linked to the phenyl ring in the 3- or 4-position.

21. The method of controlling parasites of warm-blooded animals of claim 1 which comprises orally or percutaneously administering to the animal a parasiticidally effective amount of a compound having the formula:

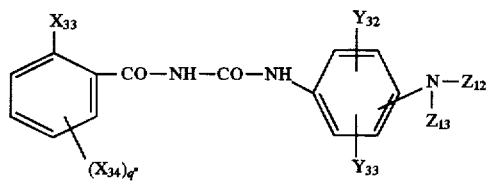

wherein:

q" is a value of from 1 to 4;

$X_{33}$ and $X_{34}$ are independently hydrogen, halogen, alkyl, alkoxy, polyhaloalkyl, nitro or polyhaloalkoxy;

$Y_{32}$ and $Y_{33}$ are independently hydrogen, halogen, alkyl or polyhaloalkyl;

$Z_{12}$ is hydrogen, alkyl, propargyl, alkenyl optionally substituted with chlorine, bromine, cycloalkyl or alkoxyalkyl; phenyl, naphthyl or tetrahydronaphthyl, all of which may be optionally substituted with halogen, alkyl, alkoxy, cyano, nitro, polyhaloalkyl or polyhaloalkoxy;

$z_{13}$ is alkyl, propargyl, alkenyl optionally substituted with halogen, cycloalkyl or alkoxyalkyl; and wherein $Z_{12}$ and $Z_{13}$ can be combined to form a heterocyclic ring selected from pyrrol, piperidine or pyridone.

22. The method of controlling parasites of warm-blooded animals of claim 1 which comprises orally or percutaneously administering to the animal a parasiticidally effective amount of a compound having the formula:

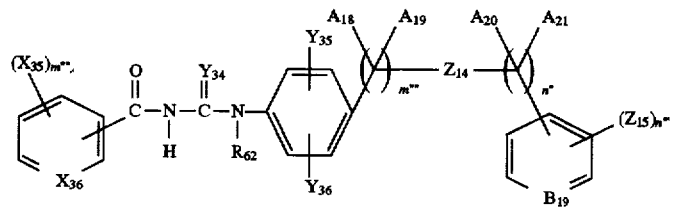

wherein:

$X_{36}$ is CH or nitrogen or oxide derivatives thereof;

$X_{35}$ is independently hydrogen, halogen, alkyl, alkoxy, polyhaloalkyl, nitro or polyhaloalkoxy:

$Y_{34}$ is oxygen or sulfur;

$R_{62}$ is hydrogen, hydroxy or alkyl;

$Y_{35}$ and $Y_{36}$ are independently halogen, alkyl, alkoxy, polyhaloalkyl or polyhaloalkoxy;

$A_{18}$, $A_{19}$, $A_{20}$ and $A_{21}$ are independently hydrogen, alkyl, alkenyl, polyhaloalkyl or halogen;

m"" is a value of from 0 to 3,n'" is a value of from 1 to 3, and n"is a value of from 0 to 3 provided that either of m"" and n" has a value of at least 1;

$B_{19}$ is CH or nitrogen or oxide derivatives thereof;

$Z_{15}$ is hydrogen, halogen, alkyl, haloalkyl, nitro, cyano, trifluoromethyl, polyhaloalkyl or polyhaloalkoxy: and $Z_{14}$ is oxygen, sulfur, sulfoxide, sulfone, substituted or unsubstituted amino or a covalent bond.

23. The method of controlling parasites of warm-blooded animals of claim 1 which comprises orally or percutaneously administering to the animal a parasiticidally effective amount of a compound having the formula:

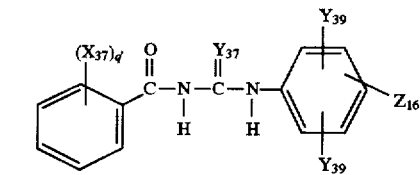

wherein:

$X_{37}$ represents independently hydrogen, halogen, alkyl, polyhaloalkyl, polyhaloalkoxy, alkoxy, nitro or alkylthio:

Q' is a value of from 1 to 5;

$Y_{37}$ is oxygen or sulfur;

$Y_{38}$ and $Y_{39}$ are independently hydrogen, halogen, alkyl, alkoxy, polyhaloalkoxy or polyhaloalkyl; and $Z_{16}$ is a heterocycle-containing moiety having the formula

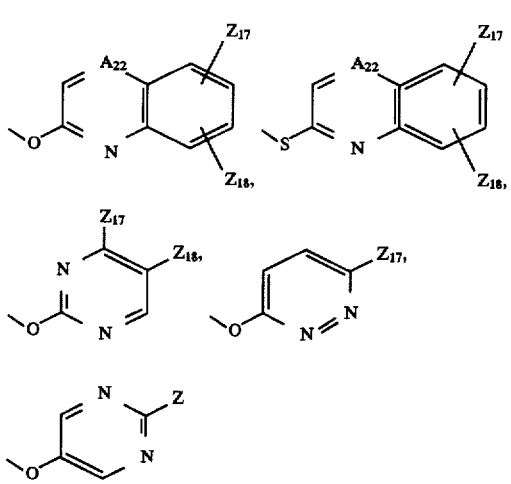

wherein $A_{22}$ is CH or nitrogen, and $Z_{17}$ and $Z_{18}$ are independently hydrogen, halogen, trifluoromethyl, nitro, alkyl, cycloalkyl, alkoxy, polyhaloalkoxy or phenyl optionally substituted with cyano, nitro, halogen, alkyl, alkoxy, polyhaloalkyl or polyhaloalkoxy; provided that $Z_{16}$ is attached at the 3- or 4- position.

24. The method of controlling parasites of warm-blooded animals of claim 1 which comprises orally or percutaneously administering to the animal a parasitically effective amount of a compound having the formula:

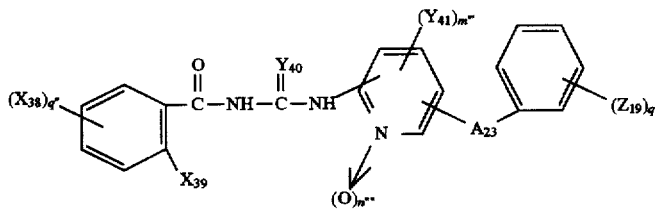

wherein $X_{38}$ and $X_{39}$ are independently hydrogen, halogen, alkyl, alkoxy, polyhaloalkyl, polyhaloalkoxy or nitro;

$Y_{40}$ is oxygen or sulfur;

$Y_{41}$ is halogen, alkyl, cyano, polyhaloalkyl, alkoxy or polyhaloalkoxy;

m'" is a value of from 0 to 2;

n'" is a value of 0 or 1;

$A_{23}$ is a covalent bond, oxygen, sulfoxide, sulfone, oxyalkyl, thioalkylene, sulfinylalkylene, sulfonylakylene, or sulfur:

$Z_{19}$ is halogen, trifluoromethyl, polyhaloalkyl, polyhaloalkoxy, polyhaloalkylthio, alkyl, nitro, cyano, alkoxy or alkylthio; and q is a value of from 0 to 4, and q" is a value of from 1 to 4.

25. The method of controlling parasites of warm-blooded animals of claim 1 which comprises orally or percutaneously administering to the animal a parasiticidally effective amount of a compound having the formula:

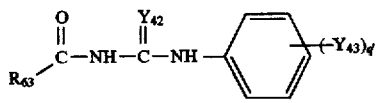

wherein:

q' is a value of from 1 to 5;

$R_{63}$ is an unsubstituted or substituted heterocyclic aromatic ring system selected from

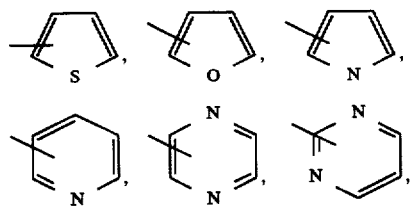

in which the permissible substituents are the same or different and are one or more halogen, hydrogen, polyhaloalkyl, alkoxy, polyhaloalkoxy or alkyl groups;

$Y_{42}$ is oxygen or sulfur;

$Y_{43}$ is independently selected from hydrogen, halogen, alkyl, polyhaloalkyl, phenyl optionally substituted with one or more hydrogen, halogen, alkyl, cyano, nitro or polyhaloalkyl; phenoxy, naphthoxy, pyridyloxy or tetrahydronaphthoxy, all optionally substituted by one or more halogen, alkyl, cyano, nitro, polyhaloalkyl, polyfluoroalkanol, alkoxy or polyhaloalkoxy; polyfluoroalkanol, alkoxy, polyhaloalkoxy, alkylcarbonyl, alkoxycarbonyl, alkylthio or dialkylamino.

26. The method of controlling parasites of warm-blooded animals of claim 1 which comprises orally or percutaneously administering to the animal a parasiticidally effective amount of a compound having the formula:

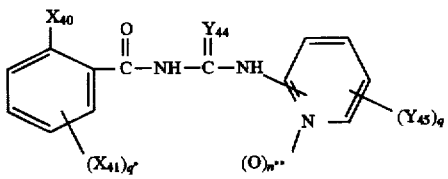

and the acid addition salt thereof, wherein:

q" is a value of from 1 to 4, and q is a value of from 0 to 4;

$X_{40}$ and $X_{41}$ are independently hydrogen, halogen, alkyl, alkoxy, polyhaloalkyl, polyhaloalkoxy or nitro;

$Y_{44}$ is oxygen or sulfur;

$Y_{45}$ is the same or different and is one or more substituents selected from hydrogen, alkynyl, halogen, polyhaloalkyl, polyhaloalkoxy, trifluoromethyl, cyano, nitro, alkyl or alkoxy; and n"" is a value of 0 or 1.

27. The method of controlling parasites of warm-blooded animals of claim 1 which comprises orally or percutaneously administering to the animal a parasiticidally effective amount of a compound having the formula:

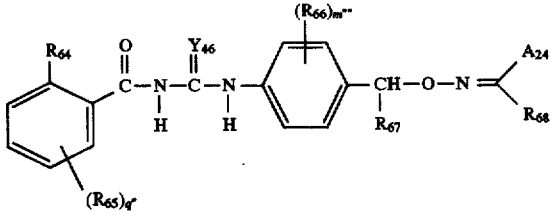

wherein:

$R_{64}$ and $R_{65}$ are independently halogen, hydrogen, alkyl, alkoxy, polyhaloalkyl, polyhaloalkoxy, or nitro;

$Y_{46}$ is oxygen or sulfur;

$R_{66}$ is halogen, alkyl, trifluoromethyl, polyhaloalkyl, polyhaloalkoxy or alkoxy;

m"" is a value of from 0 to 3 and q" is a value of from 1 to 4;

$R_{68}$ is alkyl, cycloalkyl, hydrogen, alkylthio, cyano or alkoxy;

$R_{67}$ is hydrogen or alkyl; and $A_{24}$ is alkyl, alkylthio or substituted alkyl with alkoxy, alkylthio, alkylsulfinyl or alkylsulfonyl or a ring system selected from

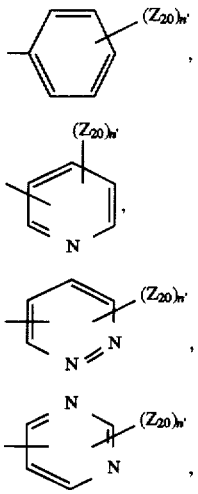

wherein $Z_{20}$ is hydrogen, halogen, alkyl, alkoxy, haloalkyl or haloalkoxy, and n' is a value from 0 to 4; $A_{24}$ and $R_{68}$ can optionally be joined to form a ring system of from 5 to 7 atoms which may contain up to two oxygen, sulfur or nitrogen atoms and which may be optionally substituted with alkyl or halogen.

28. The method of controlling parasites of warm-blooded animals of claim 1 which comprises orally or percutaneously administering to the animal a parasiticidally effective amount of a compound having the formula:

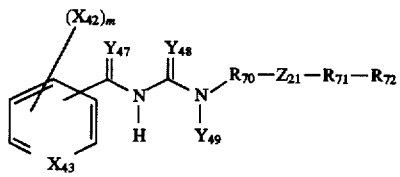

wherein:

$X_{43}$ is CH or nitrogen;

$X_{42}$ is independently halogen, alkyl or nitro;

m"" is a value of from 0 to 3;

$Y_{47}$ and $Y_{48}$ are independently oxygen or sulfur;

$Y_{49}$ is hydrogen, hydroxy or optionally substituted alkyl;

$R_{70}$ is unsubstituted or substituted phenylene or heteroarylene with one or two nitrogen atoms in which the permissible substituents are one or more halogen, optionally halogenated alkyl or alkoxy;

$R_{71}$ is alkylene, alkenylene, alkylidene, cycloalkylene or cycloalkylidene optionally substituted with one or more halogen, alkyl which may be optionally substituted by halogen or hydroxy, phenyl, cyano, alkoxycarbonyl, hydroxyimino, alkoxyimino, alkenyl or alkynyl;

$R_{72}$ is unsubstituted or substituted phenyl or heteroaryl having from 1 to 3 nitrogen, oxygen or sulfur atoms in any combination which may be the same or different in which the permissible substituents are one or more halogen, nitro, cyano, optionally halogen-substituted alkyl, alkenyl, alkoxy, alkenyloxy, alkylthio, or alkylsulfonyl; and $Z_{21}$ is oxygen, sulfur, sulfoxide, sulfone, amino or alkylimino, or $Z_{21}$ and $R_{71}$ are together alkylideneamino.

29. The method of controlling parasites of warm-blooded animals of claim 1 which comprises orally or percutaneously administering to the animal a parasiticidally effective amount of a compound having the formula:

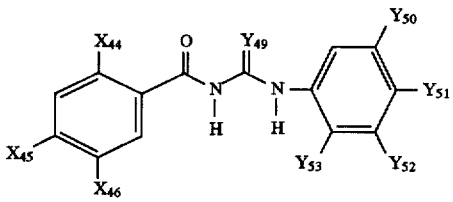

wherein:

$X_{44}$ is halogen;

$X_{45}$ and $X_{46}$ are independently hydrogen or halogen provided that when $X_{45}$ is halogen then $X_{46}$ is hydrogen, and when $X_{46}$ is halogen then X45 is hydrogen;

$Y_{49}$ is oxygen or sulfur;

$Y_{50}$ and $Y_{53}$ are independently hydrogen, halogen, optionally substituted alkyl, alkoxy, or alkylthio;

$Y_{51}$ is hydrogen, halogen, cyano, nitro or optionally substituted alkyl, alkylthio, alkylsulfonyl, alkoxy, naphthoxy, phenoxy, alkylcarbonyl, alkoxycarbonyl, alkoxycarbonylalkyl or alkoxycarbonylalkylthio, or $Y_{50}$ and $Y_{51}$ are together optionally substituted alkylenedioxy; and $Y_{52}$ is hydrogen, halogen or optionally substituted alkyl, alkoxy or aryloxy.

30. The method of claim 1 in which the compound is 1-[4-(2-bromo-4-chlorophenoxy)-2,5- dimethyl-3-chlorophenyl]-3-(2-fluorobenzoyl)urea.

31. The method of claim 1 in which the compound is 1-[4-(2,4-dimethylphenoxy)-2,5-dimethyl-3-chlorophenyl]-3-(2,6-difluorobenzoyl)urea.

32. The method of claim 1 in which the compound is 1-[4-(2,4-dichlorophenoxy)-2,5-dimethyl-3-chlorophenyl]-3-(2,6-difluorobenzoyl)urea.

33. The method of claim 1 in which the compound is 1-[4-(2-methyl-4-t-butylphenoxy)-2,5-dimethyl-3-chlorophenyl]-3-(2,6-difluorobenzoyl)urea.

34. The method of claim 1 in which the compound is 1-[2,5-dichloro-4-(alpha-cyano-4-fluoro-benzyl)phenyl]-3-(2,6-difluorobenzoyl)urea.

35. The method of claim 1 in which the compound is 1-[3-chloro-4-(4-chloro-1-naphthoxy)-2,5-dimethylphenyl]-3-(2-chlorobenzoyl)urea.

36. The method of claim 1 in which the compound is 1-[4-(4-chloro-1-naphthoxy)-2,3,5-tri-chlorophenyl]-3-(2,6-diflubrobenzoyl)urea.

37. The method of claim 1 in which the compound is 1-[4-(4-chloro-1-naphthoxy)-3,5-dimethyl-phenyl]-3-(2,6-difluorobenzoyl)urea.

38. The method of claim 1 in which the compound is 1-[3-chloro-4-(4-chloro-5,6,7,8-tetra-hydro-1-naphthoxy)-2,5-dimethylphenyl]-3- (2,6-difluorobenzoyl)urea.

39. The method of claim 1 in which the compound is 1-[3-chloro-4-(4-chloro-2,5-dimethyl-phenoxy)-2,5-dimethylphenyl]-3-(2,6-difluorobenzoyl) urea.

40. The method of claim 1 in which the compound is 1-(4-(4-nitrophenoxy)-3,5-dichloro-phenyl]-3-(2,6-difluorobenzoyl)urea.

41. The method of claim 1 in which the compound is 1-[4-(4-chlorophenoxy)-3,5-dichloro-phenyl]-3-(2,6-difluorobenzoyl)urea.

42. The method of claim 1 in which the compound is 1-[4-(5-trifluoromethyl-3-chloro-2-pyridyloxy)-3,5-dichlorophenyl]-3-(2,6-difluoro-benzoyl)urea.

43. The method of claim 1 in which the compound is 1-[3-chloro-4-(2,3-diimethyl-4-bromo-phenoxy)-2,5-dimethylphenyl]-3-(2,6-difluorobenzoyl) urea.

44. The method of claim 1 in which the compound is 1-[4-(3,5-dichloro-2-pyridyloxy)-3,5-dichlorophenyl]-3-(2,6-difluorobenzoyl)urea.

45. The method of claim 1 in which from about 0.01 mg/kg body wt. to about 1000 mg/kg body wt. of the compound is administered to the host animal.

46. The method of claim 1 in which from about 1 mg/kg body wt. to about 100 mg/kg body wt. of the compound is administered to the host animal.

47. The method of claim 1 in which the administration is oral.

48. The method of claim 3 in which the administration is as a feed additive.

49. The method of claim 1 in which the administration is percutaneous.

50. The method of claim 49 in which the administration is by injection.

51. The method of claim 49 in which the administration is by pour-on application.

52. The method of claim 49 in which the administration is by implant.

53. The method of claim 49 in which the administration is by-spraying.

54. The method of claim 49 in which the. administration is by dipping or drenching.

55. The method of claim 1 in which the compound is used in combination with one or more biologically active materials.

56. The method of claim 1, wherein the parasite is not directly affected while development of parasite is inhibited.

* * * * *